(12) United States Patent
Peak et al.

(10) Patent No.: US 7,947,291 B2
(45) Date of Patent: May 24, 2011

(54) MODIFIED SURFACE ANTIGEN

(75) Inventors: Ian Richard Anselm Peak, Jindalee (AU); Michael Paul Jennings, Carina (AU)

(73) Assignee: The University of Queensland, St. Lucia, Queensland (AU)

( * ) Notice: Subject to any disclaimer, the term of this patent is extended or adjusted under 35 U.S.C. 154(b) by 0 days.

(21) Appl. No.: 09/771,382

(22) Filed: Jan. 25, 2001

(65) Prior Publication Data

US 2002/0160016 A1     Oct. 31, 2002

Related U.S. Application Data

(60) Provisional application No. 60/177,917, filed on Jan. 25, 2000.

(51) Int. Cl.
*A61K 39/095*   (2006.01)
*A61K 39/00*    (2006.01)
*A61K 38/00*    (2006.01)
*C07K 1/00*     (2006.01)

(52) U.S. Cl. ............... 424/250.1; 424/184.1; 424/249.1; 530/300; 530/324; 530/350

(58) Field of Classification Search ............... 424/184.1, 424/190.1, 234.1, 250.1, 185.1, 164.1; 435/69.3, 435/71.1; 434/71.1; 530/300, 350; 536/23.7
See application file for complete search history.

(56) References Cited

U.S. PATENT DOCUMENTS 6,197,312 B1 * 3/2001 Peak et al. ................. 424/250.1
6,709,660 B1   3/2004 Scarlato

FOREIGN PATENT DOCUMENTS

| EP | 0 273 116 A2 | 4/2007 |
|----|----|----|
| WO | 90/06696 A2 | 6/1990 |
| WO | 97/46582 A1 | 12/1997 |
| WO | WO 99/31132 * | 6/1999 |
| WO | WO 99/31132 A1 | 6/1999 |
| WO | WO 99/36544 * | 7/1999 |
| WO | WO 99/36544 A2 | 7/1999 |
| WO | WO 9936544 * | 7/1999 |
| WO | WO 99/58683 A2 | 11/1999 |
| WO | 00/61165 A1 | 10/2000 |
| WO | 00/66741 A2 | 11/2000 |
| WO | WO 00/66791 A1 | 11/2000 |
| WO | 01/04316 A2 | 1/2001 |

OTHER PUBLICATIONS

Ellis, Vaccines, W.B. Saunders Company, 1988, Chapter 29.*
Boslego et al, Vaccines and Immunotherapy, Pergaman Press, 1991, Chapter 17.*
Zhao et al, Mol Gen Genet, Aug. 1990, 223(1):163-166.*
Gilmore et al, Mol Microbiology, Nov. 1989, 3(11):1579-1586.*
Thomas E. Creighton, in his book "Proteins: Structures and Molecular Properties, 1984", (pp. 314-315).*
Thomas E. Creighton, in his book "Protein Structure: A Practical Approach, 1989; pp. 184-186".*
Nosoh, Y. et al in "Protein Stability and Stabilizations through Protein Engineering, 1991" (chapter 7, p. 197, second paragraph.*
Greenspan et al. (Nature Biotechnology 17: 936-937, 1999).*
Bowie et al (Science, 1990, 257:1306-1310).*
Thomas E. Creighton, in his book, "Proteins: Structures and Molecular Properties, 1984", (pp. 314-315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph).*
Annika Pettersson et al., "Sequence variability of the meningococcal lactoferrin-binding protein LbpB," Gene 231:105-110 (1999).
John E. Heckels et al., "Vaccination against gonorrhoea: the potential protective effect of immunization with a synthetic peptide containing a conserved epitope of gonococcal outer membrane protein IB," Vaccine 8:225-230 (Jun. 1990).
Mariagrazia Pizza et al., (XP-000914964) "Identification of Vaccine Candidates Against Serogroup B Meningococcus by Whole-Genome Sequencing," Science 287:1816-1820 (Mar. 10, 2000) with XP002312283—EBI accession No. UNIPROT:Q9JR18—Database accession No. Q9JR18.
Ian R. A. Peak et al., "Identification and characterisation of a novel conserved outer membrane protein from Neisseria meningitidis," FEMS Immunology and Medical Microbiology 28:329-334 (2000).
J. Parkhill et al., (XP-000918875) "Complete DNA sequence of a serogroup A strain of Neisseria meningitidis Z2491," Nature 404:502-505 (Mar. 30, 2000).
Herve Tettelin et al., (XP-000914963) "Complete Genome Sequence of Neisseria meningitidis Serogroup B Strain MC58," Science 287: 1809-1815 (Mar. 10, 2000).

* cited by examiner

*Primary Examiner* — Vanessa L. Ford
(74) *Attorney, Agent, or Firm* — Panitch Schwarze Belisario & Nadel LLP

(57) ABSTRACT

Novel proteins that constitute modified forms of a *Neisseria meningitidis* surface antigen and encoding nucleic acids are provided. The modified surface proteins are characterized by having deletions of non-conserved amino acids, and thereby being capable of eliciting cross-protective immune responses against *Neisseria meningitidis*. The invention extends to the use of the modified surface antigens in diagnostics, in therapeutic and prophylactic vaccines and in the design and/or screening of medicaments. The modified surface antigens are particularly useful in vaccines which effectively immunize against a broader spectrum of *N. meningitidis* strains than would be expected from a corresponding wild-type surface antigen.

13 Claims, 31 Drawing Sheets

Figure 3A:
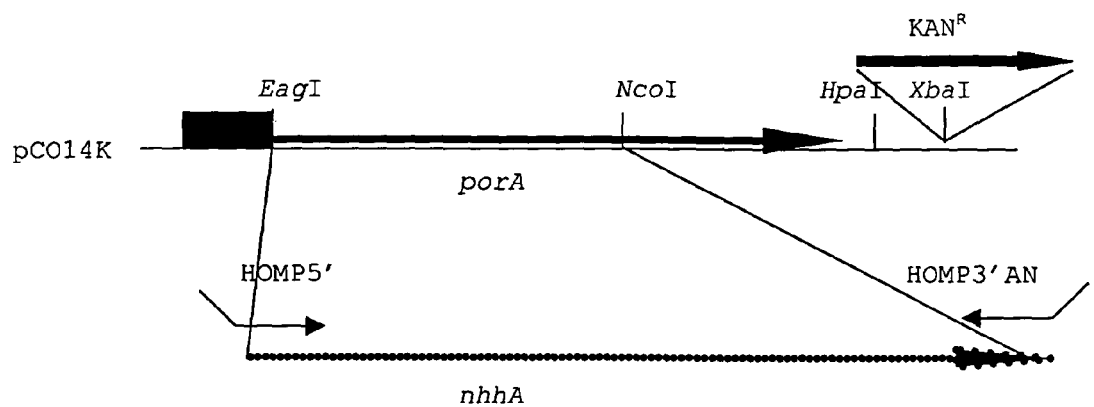

```
            1                                                     50
    EG327   MNKIYRIIWN SALNAWVAVS ELTRNHTKRA SATVATAVLA TLLFATVQAS
    BZ198   MNKIYRIIWN SALNAWVVVS ELTRNHTKRA SATVATAVLA TLLFATVQAN
     BZ10   MNKISRIIWN SALNAWVVVS ELTRNHTKRA SATVATAVLA TLLFATVQAN
      H15   MNKIYRIIWN SALNAWVVVS ELTRNHTKRA SATVATAVLA TLLFATVQAN
    EG329   MNEILRIIWN SALNAWVVVS ELTRNHTKRA SATVKTAVLA TLLFATVQAS
    PMC21   MNKIYRIIWN SALNAWVVVS ELTRNHTKRA SATVKTAVLA TLLFATVQAS
      H38   MNKIYRIIWN SALNAWVAVS ELTRNHTKRA SATVKTAVLA TLLFATVQAN
      P20   MNKIYRIIWN SALNAWVVVS ELTRNHTKRA SATVATAVLA TLLSATVQAN
    Z2491   MNKIYRIIWN SALNAWVAVS ELTRNHTKRA SATVKTAVLA TLLFATVQAN
      H41   MNKIYRIIWN SALNAWVAVS ELTRNHTKRA SATVKTAVLA TLLFATVQAN
Consensus   MN-I-RIIWN SALNAWV-VS ELTRNHTKRA SATV-TAVLA TLL-ATVQA-
                                      C1

51                                                    100
    EG327   TTDDD...DL YLEPVQRTAV VLSFRSDKEG TGEKE.VTED SNWGVYFDKK
    BZ198   ATDDD...DL YLEPVQRTAV VLSFRSDKEG TGEKE.GTED SNWAVYFDEK
     BZ10   ATDDD...DL YLEPVQRTAV VLSFRSDKEG TGEKE.GTED SNWAVYFDEK
      H15   ATDDD...DL YLEPVQRTAV VLSFRSDKEG TGEKE.GTED SNWAVYFDEK
    EG329   ANNEEQEEDL YLDPVLRTVA VLIVNSDKEG TGEKEKVEEN SDWAVYFNEK
    PMC21   ANNEEQEEDL YLDPVQRTVA VLIVNSDKEG TGEKEKVEEN SDWAVYFNEK
      H38   ATDED..EEE ELEPVVRSAL VLQFMIDKEG NGENE.STGN IGWSIYYDNH
      P20   ATDTD..EDE ELESVARSAL VLQFMIDKEG NGEIESTGDI GWSIYYDDHN
    Z2491   ATDED..EEE ELESVQR.SV VGSIQASMEG SGELET...I SLSMTNDSKE
      H41   ATDED..EEE ELESVQR.SV VGSIQASMEG SVELET...I SLSMTNDSKE
Consensus   ---------- -L--V-R--- V-------EG --E-E----- ----------
                                      V1

101                                                   150
    EG327   GVLTAGTITL KAGDNLKIKQ NTNENTNASS ....FTYSLK KDLTDLTSVG
    BZ198   RVLKAGAITL KAGDNLKIKQ NTNENTNDSS ....FTYSLK KDLTDLTSVE
     BZ10   RVLKAGAITL KAGDNLKIKQ NTNENTNENT NDSSFTYSLK KDLTDLTSVE
      H15   RVLKAGAITL KAGDNLKIKQ NTNENTNENT NDSSFTYSLK KDLTDLTSVE
    EG329   GVLTAREITL KAGDNLKIKQ NG...TN... ....FTYSLK KDLTDLTSVG
    PMC21   GVLTAREITL KAGDNLKIKQ NG...TN... ....FTYSLK KDLTDLTSVG
      H38   NTLHGATVTL KAGDNLKIKQ NTNKNTNENT NDSSFTYSLK KDLTDLTSVE
      P20   TLHG.ATVTL KAGDNLKIKQ SGKD...... ....FTYSLK KELKDLTSVE
    Z2491   FVDPYIVVTL KAGDNLKIKQ NTNENTNASS ....FTYSLK KDLTGLINVE
      H41   FVDPYIVVTL KAGDNLKIKQ NTNENTNASS ....FTYSLK KDLTGLINVE
Consensus   --------TL KAGDNLKIKQ ---------- ----FTYSLK K-L--L--V-
                V1         C2         V2              C3
```

*FIG. 1A*

```
              151                                                                         200
    EG327     TEKLSFSANS  NKVNITSDTK  GLNFAKKTAE  TNGDTTVHLN  GIGSTLTDTL
    BZ198     TEKLSFGANG  NKVNITSDTK  GLNFAKETAG  TNGDPTVHLN  GIGSTLTDTL
     BZ10     TEKLSFGANG  NKVNITSDTK  GLNFAKETAG  TNGDPTVHLN  GIGSTLTDTL
      H15     TEKLSFGANG  NKVNITSDTK  GLNFAKETAG  TNGDPTVHLN  GIGSTLTDTL
    EG329     TEKLSFSANG  NKVNITSDTK  GLNFAKETAG  TNGDTTVHLN  GIGSTLTDTL
    PMC21     TEKLSFSANG  NKVNITSDTK  GLNFAKETAG  TNGDTTVHLN  GIGSTLTDTL
      H38     TEKLSFGANG  NKVNITSDTK  GLNFAKETAG  TNGDTTVHLN  GIGSTLTDTL
      P20     TEKLSFGANG  NKVNITSDTK  GLNFAKETAG  TNGDPTVHLN  GIGSTLTDTL
    Z2491     TEKLSFGANG  KKVNIISDTK  GLNFAKETAG  TNGDTTVHLN  GIGSTLTDTL
      H41     TEKLSFGANG  KKVNIISDTK  GLNFAKETAG  TNGDTTVHLN  GIGSTLTDML
Consensus     TEKLSF-AN-  -KVNI-SDTK  GLNFAK-TA-  TNGD-TVHLN  GIGSTLTD-L
                                          C3
```

```
              201                                                                         250
    EG327     LNTGATTNVT  NDNVTDDEKK  RAASVKDVLN  AGWNIKGVKP  GTTAS..DNV
    BZ198     LNTGATTNVT  NDNVTDDEKK  RAASVKDVLN  AGWNIKGVKP  GTTAS..DNV
     BZ10     LNTGATTNVT  NDNVTDDEKK  RAASVKDVLN  AGWNIKGVKP  GTTAS..DNV
      H15     LNTGATTNVT  NDNVTDDEKK  RAASVKDVLN  AGWNIKGVKP  GTTAS..DNV
    EG329     LNTGATTNVT  NDNVTDDEKK  RAASVKDVLN  AGWNIKGVKP  GTTAS..DNV
    PMC21     LNTGATTNVT  NDNVTDDEKK  RAASVKDVLN  AGWNIKGVKP  GTTAS..DNV
      H38     LNTGATTNVT  NDNVTDDKKK  RAASVKDVLN  AGWNIKGVKP  GTTAS..DNV
      P20     AGSSASHVDA  GNQST..HYT  RAASIKDVLN  AGWNIKGVKT  GSTTGQSENV
    Z2491     AGSSASHVDA  GNQST..HYT  RAASIKDVLN  AGWNIKGVKT  GSTTGQSENV
      H41     LNTGATTNVT  NDNVTDDEKK  RAASVKDVLN  AGWNIKGVKP  GTTAS..DNV
Consensus     ----A-----  ----T-----  RAAS-KDVLN  AGWNIKGVK-  G-T----NV
                  V3                       C4                      V4
```

```
              251                                                                         300
    EG327     DFVRTYDTVE  FLSADTKTTT  VNVESKDNGK  RTEVKIGAKT  SVIKEKDGKL
    BZ198     DFVRTYDTVE  FLSADTKTTT  VNVESKDNGK  KTEVKIGAKT  SVIKEKDGKL
     BZ10     DFVRTYDTVE  FLSADTKTTT  VNVESKDNGK  RTEVKIGAKT  SVIKEKDGKL
      H15     DFVRTYDTVE  FLSADTKTTT  VNVESKDNGK  KTEVKIGAKT  SVIKEKDGKL
    EG329     DFVRTYDTVE  FLSADTKTTT  VNVESKDNGK  KTEVKIGAKT  SVIKEKDGKL
    PMC21     DFVRTYDTVE  FLSADTKTTT  VNVESKDNGK  KTEVKIGAKT  SVIKEKDGKL
      H38     DFVHTYDTVE  FLSADTKTTT  VNVESKDNGK  RTEVKIGAKT  SVIKEKDGKL
      P20     DFVRTYDTVE  FLSADTKTTT  VNVESKDNGK  RTEVKIGAKT  SVIKEKDGKL
    Z2491     DFVRTYDTVE  FLSADTKTTT  VNVESKDNGK  RTEVKIGAKT  SVIKEKDGKL
      H41     DFVRTYDTVE  FLSADTKTTT  VNVESKDNGK  KTEVKIGAKT  SVIKEKDGKL
Consensus     DFV-TYDTVE  FLSADTKTTT  VNVESKDNGK  -TEVKIGAKT  SVIKEKDGKL
                                          C5
```

*FIG. 1B*

```
             301                                                      350
    EG327    VTGKDKGEND  SSTDKGEGLV  TAKEVIDAVN  KAGWRMKTTT  ANGQTGQADK
    BZ198    VTGKGKDENG  SSTDEGEGLV  TAKEVIDAVN  KAGWRMKTTT  ANGQTGQADK
     BZ10    VTGKGKGENG  SSTDEGEGLV  TAKEVIDAVN  KAGWRMKTTT  ANGQTGQADK
      H15    VTGKGKDENG  SSTDEGEGLV  TAKEVIDAVN  KAGWRMKTTT  ANGQTGQADK
    EG329    VTGKDKGENG  SSTDEGEGLV  TAKEVIDAVN  KAGWRMKTTT  ANGQTGQADK
    PMC21    VTGKDKGENG  SSTDEGEGLV  TAKEVIDAVN  KAGWRMKTTT  ANGQTGQADK
      H38    VTGKGKGENG  SSTDEGEGLV  TAKEVIDAVN  KAGWRMKTTT  ANGQTGQADK
      P20    VTGKGKGENG  SSTDEGEGLV  TAKEVIDAVN  KAGWRMKTTT  ANGQTGQADK
    Z2491    VTGKGKGENG  SSTDEGEGLV  TAKEVIDAVN  KAGWRMKTTT  ANGQTGQADK
      H41    VTGKGKGENG  SSTDEGEGLV  TAKEVIDAVN  KAGWRMKTTT  ANGQTGQADK
Consensus    VTGK-K-EN-  SSTD-GEGLV  TAKEVIDAVN  KAGWRMKTTT  ANGQTGQADK
                                        C5

351                                                      400
    EG327    FETVTSGTNV  TFASGKGTTA  TVSKDDQGNI  TVMYDVNVGD  ALNVNQLQNS
    BZ198    FETVTSGTNV  TFASGKGTTA  TVSKDDQGNI  TVKYDVNVGD  ALNVNQLQNS
     BZ10    FETVTSGTKV  TFASGNGTTA  TVSKDDQGNI  TVKYDVNVGD  ALNVNQLQNS
      H15    FETVTSGTKV  TFASGNGTTA  TVSKDDQGNI  TVKYDVNVGD  ALNVNQLQNS
    EG329    FETVTSGTNV  TFASGKGTTA  TVSKDDQGNI  TVMYDVNVGD  ALNVNQLQNS
    PMC21    FETVTSGTNV  TFASGKGTTA  TVSKDDQGNI  TVMYDVNVGD  ALNVNQLQNS
      H38    FETVTSGTNV  TFASGKGTTA  TVSKDDQGNI  TVKYDVNVGD  ALNVNQLQNS
      P20    FETVTSGTKV  TFASGNGTTA  TVSKDDQGNI  TVKYDVNVGD  ALNVNQLQNS
    Z2491    FETVTSGTNV  TFASGKGTTA  TVSKDDQGNI  TVMYDVNVGD  ALNVNQLQNS
      H41    FETVTSGTKV  TFASGNGTTA  TVSKDDQGNI  TVKYDVNVGD  ALNVNQLQNS
Consensus    FETVTSGT-V  TFASG-GTTA  TVSKDDQGNI  TV-YDVNVGD  ALNVNQLQNS
                                        C5

401                                                      450
    EG327    GWNLDSKAVA  GSSGKVISGN  VSPSKGKMDE  TVNINAGNNI  EITRNGKNID
    BZ198    GWNLDSKAVA  GSSGKVISGN  VSPSKGKMDE  TVNINAGNNI  EITRNGKNID
     BZ10    GWNLDSKAVA  GSSGKVISGN  VSPSKGKMDE  TVNINAGNNI  EITRNGKNID
      H15    GWNLDSKAVA  GSSGKVISGN  VSPSKGKMDE  TVNINAGNNI  EITRNGKNID
    EG329    GWNLDSKAVA  GSSGKVISGN  VSPSKGKMDE  TVNINAGNNI  EITRNGKNID
    PMC21    GWNLDSKAVA  GSSGKVISGN  VSPSKGKMDE  TVNINAGNNI  EITRNGKNID
      H38    GWNLDSKAVA  GSSGKVISGN  VSPSKGKMDE  TVNINAGNNI  EITRNGKNID
      P20    GWNLDSKAVA  GSSGKVISGN  VSPSKGKMDE  TVNINAGNNI  EITRNGKNID
    Z2491    GWNLDSKAVA  GSSGKVISGN  VSPSKGKMDE  TVNINAGNNI  EISRNGKNID
      H41    GWNLDSKAVA  GSSGKVISGN  VSPSKGKMDE  TVNINAGNNI  EITRNGKNID
Consensus    GWNLDSKAVA  GSSGKVISGN  VSPSKGKMDE  TVNINAGNNI  EI-RNGKNID
                                        C5
```

FIG. 1C

```
              451                                                        500
      EG327   IATSMTPQFS  SVSLGAGADA  PTLSVDDEGA  LNVGSKDANK  PVRITNVAPG
      BZ198   IATSMAPQFS  SVSLGAGADA  PTLSVDDEGA  LNVGSKDTNK  PVRITNVAPG
       BZ10   IATSMTPQFS  SVSLGAGADA  PTLSVDDEGA  LNVGSKDANK  PVRITNVAPG
        H15   IATSMTPQFS  SVSLGAGADA  PTLSVDDEGA  LNVGSKDANK  PVRITNVAPG
      EG329   IATSMTPQFS  SVSLGAGADA  PTLSVDG.DA  LNVGSKKDNK  PVRITNVAPG
      PMC21   IATSMTPQFS  SVSLGAGADA  PTLSVDG.DA  LNVGSKKDNK  PVRITNVAPG
        H38   IATSMTPQFS  SVSLGAGADA  PTLSVDDKGA  LNVGSKDANK  PVRITNVAPG
        P20   IATSMTPQFS  SVSLGAGADA  PTLSVDDEGA  LNVGSKDANK  PVRITNVAPG
      Z2491   IATSMAPQFS  SVSLGAGADA  PTLSVDDEGA  LNVGSKDANK  PVRITNVAPG
        H41   IATSMTPQFS  SVSLGAGADA  PTLSVDDEGA  LNVGSKDANK  PVRITNVAPG
  Consensus   IATSM-PQFS  SVSLGAGADA  PTLSVD---A  LNVGSK--NK  PVRITNVAPG
                                          C5

501                                                        550
      EG327   VKEGDVTNVA  QLKGVAQNLN  NHIDNVDGNA  RAGIAQAIAT  AGLVQAYLPG
      BZ198   VKEGDVTNVA  QLKGVAQNLN  NRIDNVDGNA  RAGIAQAIAT  AGLVQAYLPG
       BZ10   VKEGDVTNVA  QLKGVAQNLN  NRIDNVDGNA  RAGIAQAIAT  AGLAQAYLPG
        H15   VKEGDVTNVA  QLKGVAQNLN  NRIDNVDGNA  RAGIAQAIAT  AGLAQAYLPG
      EG329   VKEGDVTNVA  QLKGVAQNLN  NRIDNVDGNA  RAGIAQAIAT  AGLVQAYLPG
      PMC21   VKEGDVTNVA  QLKGVAQNLN  NRIDNVDGNA  RAGIAQAIAT  AGLVQAYLPG
        H38   VKEGDVTNVA  QLKGVAQNLN  NRIDNVDGNA  RAGIAQAIAT  AGLVQAYLPG
        P20   VKEGDVTNVA  QLKGVAQNLN  NRIDNVNGNA  RAGIAQAIAT  AGLAQAYLPG
      Z2491   VKEGDVTNVA  QLKGVAQNLN  NRIDNVDGNA  RAGIAQAIAT  AGLVQAYLPG
        H41   VKEGDVTNVA  QLKGVAQNLN  NRIDNVNGNA  RAGIAQAIAT  AGLVQAYLPG
  Consensus   VKEGDVTNVA  QLKGVAQNLN  N-IDNV-GNA  RAGIAQAIAT  AGL-QAYLPG
                                          C5

551                                                        600
      EG327   KSMMAIGGGT  YRGEAGYAIG  YSSISDGGNW  IIKGTASGNS  RGHFGASASV
      BZ198   KSMMAIGGDT  YRGEAGYAIG  YSSISDGGNW  IIKGTASGNS  RGHFGASASV
       BZ10   KSMMAIGGGT  YRGEAGYAIG  YSSISDTGNW  VIKGTASGNS  RGHFGTSASV
        H15   KSMMAIGGGT  YRGEAGYAIG  YSSISDTGNW  VIKGTASGNS  RGHFGASASV
      EG329   KSMMAIGGGT  YRGEAGYAIG  YSSISDGGNW  IIKGTASGNS  RGHFGASASV
      PMC21   KSMMAIGGGT  YRGEAGYAIG  YSSISDGGNW  IIKGTASGNS  RGHFGASASV
        H38   KSMMAIGGGT  YRGEAGYAIG  YSSISDGGNW  IIKGTASGNS  RGHFGASASV
        P20   KSMMAIGGGT  YLGEAGYAIG  YSSISDTGNW  VIKGTASGNS  RGHFGTSASV
      Z2491   KSMMAIGGGT  YRGEAGYAIG  YSSISDGGNW  IIKGTASGNS  RGHFGASASV
        H41   KSMMAIGGGT  YLGEAGYAIG  YSSISAGGNW  IIKGTASGNS  RGHFGASASV
  Consensus   KSMMAIGG-T  Y-GEAGYAIG  YSSIS--GNW  -IKGTASGNS  RGHFG-SASV
                                          C5
```

FIG. 1D

```
              601
    EG327   GYQW.
    BZ198   GYQW.
     BZ10   GYQW.
      H15   GYQW.
    EG329   GYQW.
    PMC21   GYQW.
      H38   GYQW.
      P20   GYQW.
    Z2491   GYQW.
      H41   GYQW.
Consensus   GYQW.
             C5
```

FIG. 1E

```
              1                                                                    70
    H15   ATGAACAAAA TATACCGCAT CATTTGGAAT AGTGCCCTCA ATGCCTGGGT CGTCGTATCC GAGCTCACAC
    BZ10  ATGAACAAAA TATCCCGCAT CATTTGGAAT AGTGCCCTCA ATGCCTGGGT CGTCGTATCC GAGCTCACAC
    BZ198 ATGAACAAAA TATACCGCAT CATTTGGAAT AGTGCCCTCA ATGCCTGGGT CGTCGTATCC GAGCTCACAC
    P20   ATGAACAAAA TATACCGCAT CATTTGGAAT AGTGCCCTCA ATGCCTGGGT AGTCGTATCC GAGCTCACAC
    H38   ATGAACAAAA TATACCGCAT CATTTGGAAT AGTGCCCTCA ATGCCTGGGT CGCCGTATCC GAGCTCACAC
    Z2491 ATGAACAAAA TATACCGCAT CATTTGGAAT AGTGCCCTCA ATGCCTGGGT CGCCGTATCC GAGCTCACAC
    H41   ATGAACAAAA TATACCGCAT CATTTGGAAT AGTGCCCTCA ATGCCTGGGT CGCCGTATCC GAGCTCACAC
    EG329 ATGAACGAAA TATTGCGCAT CATTTGGAAT AGCGCCCTCA ATGCCTGGGT CGTTGTATCC GAGCTCACAC
    PMC21 ATGAACAAAA TATACCGCAT CATTTGGAAT AGTGCCCTCA ATGCATGGGT CGTCGTATCC GAGCTCACAC
    EG327 ATGAACAAAA TATACCGCAT·CATTTGGAAT AGTGCCCTCA ATGCCTGGGT CGCCGTATCC GAGCTCACAC
Consensus ATGAAC-AAA TAT--CGCAT CATTTGGAAT AG-GCCCTCA ATGC-TGGGT -G--GTATCC GAGCTCACAC
                                              C1
```

```
              71                                                                   140
    H15   GCAACCACAC CAAACGCGCC TCCGCAACCG TGGCGACCGC CGTATTGGCG ACACTGTTGT TTGCAACGGT
    BZ10  GCAACCACAC CAAACGCGCC TCCGCAACCG TGGCGACCGC CGTATTGGCG ACACTGTTGT TTGCAACGGT
    BZ198 GCAACCACAC CAAACGCGCC TCCGCAACCG TGGCGACCTC CGTATTGGCG ACACTGTTGT TTGCAACGGT
    P20   GCAACCACAC CAAACGCGCC TCCGCAACCG TGGCGACCGC CGTATTGGCG ACACTGCTGT CCGCAACGGT
    H38   GCAACCACAC CAAACGCGCC TCCGCAACCG TGAAGACCGC CGTATTGGCG ACGCTGTTGT TTGCAACGGT
    Z2491 GCAACCACAC CAAACGCGCC TCCGCAACCG TGAAGACCGC CGTATTGGCG ACACTGTTGT TTGCAACGGT
    H41   GCAACCACAC CAAACGCGCC TCCGCAACCG TGAAGACCGC CGTATTGGCG ACACTGTTGT TTGCAACGGT
    EG329 GCAACCACAC CAAACGCGCC TCCGCAACCG TGAAGACCGC CGTATTGGCG ACTCTGTTGT TTGCAACGGT
    PMC21 GCAACCACAC CAAACGCGCC TCCGCAACCG TGAAGACCGC CGTATTGGCG ACTCTGTTGT TTGCAACGGT
    EG327 GCAACCACAC CAAACGCGCC TCCGCAACCG TGGCGACCGC CGTATTGGCG ACACTGTTGT TTGCAACGGT
Consensus GCAACCACAC CAAACGCGCC TCCGCAACCG TG--GACCGC CGTATTGGCG AC-CTG-TGT ---GCAACGGT
                                              C1
```

```
              141                                                                  210
    H15   TCAGGCGAAT GCTACCGATG ACGAC..... .....GATTTA TATTTAGAAC CCGTACAACG CACTGCTGTC
    BZ10  TCAGGCGAAT GCTACCGATG ACGAC..... .....GATTTA TATTTAGAAC CCGTACAACG CACTGCTGTC
    BZ198 TCAGGCGAAT GCTACCGATG ACGAC..... .....GATTTA TATTTAGAAC CCGTACAACG CACTGCTGTC
    P20   TCAGGCGAAT GCTACCGATA CCGAT..... .GAAGATGAA GAGTTAGAAT CCGTAGCACG CTCTGCTCTG
    H38   TCAGGCGAAT GCTACCGATG AAGAT..... .GAAGAAGAA GAGTTAGAAC CCGTAGTACG CTCTGCTCTG
    Z2491 TCAGGCGAAT GCTACCGATG AAGAT..... .GAAGAAGAA GAGTTAGAAT CCGTACAACG CTCTGTCGTA
    H41   TCAGGCGAAT GCTACCGATG AAGAT..... .GAAGAAGAA GAGTTAGAAC CCGTACAACG CTCTG...TC
    EG329 TCAGGCAAGT GCTAACAATG AAGAGCAAGA AGAAGATTTA TATTTAGACC CCGTGCTACG CACTGTTGCC
    PMC21 TCAGGCAAGT GCTAACAATG AAGAGCAAGA AGAAGATTTA TATTTAGACC CCGTACAACG CACTGTTGCC
    EG327 TCAGGCGAGT ACTACCGATG ACGAC..... .....GATTTA TATTTAGAAC CCGTACAACG CACTGCTGTC
Consensus TCAGGC-A-T -CTA-C-AT- --GA------ ----GA---A -A-TTAGA-- CCGT---ACG C-CTG-----
              C1                                      V1
```

FIG. 2A

```
            211                                                              280
      H15   GTGTTGAGCT TCCGTTCCGA TAAAGAAGGC ACGGGAGAAA AAGAAGGTAC AGAAGA...T TCAAATTGGG
      BZ10  GTGTTGAGCT TCCGTTCCGA TAAAGAAGGC ACGGGAGAAA AAGAAGGTAC AGAAGA...T TCAAATTGGG
      BZ198 GTGTTGAGCT TCCGTTCCGA TAAAGAAGGC ACGGGAGAAA AAGAAGGTAC AGAAGA...T TCAAATTGGG
      P20   GTGTTGCAAT TCATGATCGA TAAAGAAGGC AATGGAGAAA TCGAATCTAC AGGAGA...T ATAGGTTGGA
      H38   GTGTTGCAAT TCATGATCGA TAAAGAAGGC AATGGAGAAA ACGAATCTAC AGGAAA...T ATAGGTTGGA
      Z2491 GGG..AGCAT TCAAG.CCAG TATGGAAGGC AGCGGCGAAT TGGAAACGAT ATCAT....T ATCAATGACT
      H41   GTAGGGAGCA TTCAAGCCAG TATGGAAGGC AGCGTCGAAT TGGAAACGAT A......... TCATTATCAA
      EG329 GTGTTGATAG TCAATTCCGA TAAAGAAGGC ACGGGAGAAA AAGAAAAAGT AGAAGAAAAT TCAGATTGGG
      PMC21 GTGTTGATAG TCAATTCCGA TAAAGAAGGC ACGGGAGAAA AAGAAAAAGT AGAAGAAAAT TCAGATTGGG
      EG327 GTGTTGAGCT TCCGTTCCGA TAAAGAAGGC ACGGGAGAAA AAGAAGTTAC AGAAGA...T TCAAATTGGG
  Consensus G--------- T------C-- TA--GAAGGC A--G--GAA- --GAA----- A--------- ----------
                                                V1

281                                                              350
      H15   CAGTATATTT CGACGAGAAA AGAGTACTAA AAGCCGGAGC AATCACCCTC AAAGCCGGCG ACAACCTGAA
      BZ10  CAGTATATTT CGACGAGAAA AGAGTACTAA AAGCCGGAGC AATCACCCTC AAAGCCGGCG ACAACCTGAA
      BZ198 CAGTATATTT CGACGAGAAA AGAGTACTAA AAGCCGGAGC AATCACCCTC AAAGCCGGCG ACAACCTGAA
      P20   GTATATATTA CGACGATCAC AACACTCTAC ACGGCGCAAC CGTTACCCTC AAAGCCGGCG ACAACCTGAA
      H38   GTATATATTA CGACAATCAC AACACTCTAC ACGGCGCAAC CGTTACCCTC AAAGCCGGCG ACAACCTGAA
      Z2491 AACGACAGCA AGGAATTTGT AGACCCATAC ATAGTA.... .GTTACCCTC AAAGCCGGCG ACAACCTGAA
      H41   TGACTAACGA CAGCAAGGAA TTTGTAGACC CATACATAGT AGTTACCCTC AAAGCCGGCG ACAACCTGAA
      EG329 CAGTATATTT CAACGAGAAA GGAGTACTAA CAGCCAGAGA AATCACCCTC AAAGCCGGCG ACAACCTGAA
      PMC21 CAGTATATTT CAACGAGAAA GGAGTACTAA CAGCCAGAGA AATCACCCTC AAAGCCGGCG ACAACCTGAA
      EG327 GAGTATATTT CGACAAGAAA GGAGTACTAA CAGCCGGAAC AATCACCCTC AAAGCCGGCG ACAACCTGAA
  Consensus ------A--- ---------- ---------- ---------- --T-ACCCTC AAAGCCGGCG ACAACCTGAA
                                 V1                                C2

351                                                              420
      H15   AATCAAACAA AACACCAATG AAAACACCAA TGAAAACACC AATGACAGTA GCTTCACCTA CTCCCTGAAA
      BZ10  AATCAAACAA AACACCAATG AAAACACCAA TGAAAACACC AATGACAGTA GCTTCACCTA CTCCCTGAAA
      BZ198 AATCAAACAA AACACCAATG AAAACACC.. .......... AATGACAGTA GCTTCACCTA CTCCCTGAAA
      P20   AATCAAACAA AGCGGCAAAG A......... .......... .CTTCACCTA CTCGCTGAAA
      H38   AATCAAACAA AACACCAATA AAAACACCAA TGAAAACACC AATGACAGTA GCTTCACCTA CTCGCTGAAA
      Z2491 AATCAAACAA AACACCAATG AAAACACC.. .......... AATGCCAGTA GCTTCACCTA CTCGCTGAAA
      H41   AATCAAACAA AACACCAATG AAAACACC.. .......... AATGCCAGTA GCTTCACCTA CTCGCTGAAA
      EG329 AATCAAACAA AAC....... ........G.. .......... ....GCACAA ACTTCACCTA CTCGCTGAAA
      PMC21 AATCAAACAA AAC....... ........G.. .......... ....GCACAA ACTTCACCTA CTCGCTGAAA
      EG327 AATCAAACAA AACACCAATG AAAACACC.. .......... AATGCCAGTA GCTTCACCTA CTCGCTGAAA
  Consensus AATCAAACAA A-C------- ---------- ---------- ---------- -CTTCACCTA CTC-CTGAAA
                  C2                           V2                        C3
```

FIG. 2B

```
            421                                                                       490
     H15  AAAGACCTCA CAGATCTGAC CAGTGTTGAA ACTGAAAAAT TATCGTTTGG CGCAAACGGT AATAAAGTCA
     BZ10 AAAGACCTCA CAGATCTGAC CAGTGTTGAA ACTGAAAAAT TATCGTTTGG CGCAAACGGT AATAAAGTCA
    BZ198 AAAGACCTCA CAGATCTGAC CAGTGTTGAA ACTGAAAAAT TATCGTTTGG CGCAAACGGT AATAAAGTCA
     P20  AAAGAGCTGA AAGACCTGAC CAGTGTTGAA ACTGAAAAAT TATCGTTTGG CGCAAACGGT AATAAAGTCA
     H38  AAAGACCTCA CAGATCTGAC CAGTGTTGAA ACTGAAAAAT TATCGTTTGG CGCAAACGGC AATAAAGTCA
    Z2491 AAAGACCTCA CAGGCCTGAT CAATGTTGAA ACTGAAAAAT TATCGTTTGG CGCAAACGGC AAGAAAGTCA
     H41  AAAGACCTCA CAGGCCTGAT CAATGTTGAA ACTGAAAAAT TATCGTTTGG CGCAAACGGC AAGAAAGTCA
    EG329 AAAGACCTCA CAGATCTGAC CAGTGTTGGA ACTGAAAAAT TATCGTTTAG CGCAAACGGC AATAAAGTCA
    PMC21 AAAGACCTCA CAGATCTGAC CAGTGTTGGA ACTGAAAAAT TATCGTTTAG CGCAAACGGC AATAAAGTCA
    EG327 AAAGACCTCA CAGATCTGAC CAGTGTTGGA ACTGAAAAAT TATCGTTTAG CGCAAACAGC AATAAAGTCA
Consensus AAAGA-CT-A -AG--CTGA- CA-TGTTG-A ACTGAAAAAT TATCGTTT-G CGCAAAC-G- AA-AAAGTCA
                                           C3

491                                                                       560
     H15  ACATCACAAG CGACACCAAA GGCTTGAATT TTGCGAAAGA AACGGCTGGG ACGAACGGCG ACCCCACGGT
     BZ10 ACATCACAAG CGACACCAAA GGCTTGAATT TTGCGAAAGA AACGGCTGGG ACGAACGGCG ACCCCACGGT
    BZ198 ACATCACAAG CGACACCAAA GGCTTGAATT TTGCGAAAGA AACGGCTGGG ACGAACGGCG ACCCCACGGT
     P20  ACATCACAAG CGACACCAAA GGCTTGAATT TTGCGAAAGA AACGGCTGGG ACGAACGGCG ACCCCACGGT
     H38  ACATCACAAG CGACACCAAA GGCTTGAATT TCGCGAAAGA AACGGCTGGG ACGAACGGCG ACACCACGGT
    Z2491 ACATCATAAG CGACACCAAA GGCTTGAATT TCGCGAAAGA AACGGCTGGG ACGAACGGCG ACACCACGGT
     H41  ACATCATAAG CGACACCAAA GGCTTGAATT TCGCGAAAGA AACGGCTGGG ACGAACGGCG ACACCACGGT
    EG329 ACATCACAAG CGACACCAAA GGCTTGAATT TTGCGAAAGA AACGGCTGGG ACGAACGGCG ACACCACGGT
    PMC21 ACATCACAAG CGACACCAAA GGCTTGAATT TTGCGAAAGA AACGGCTGGG ACGAACGGCG ACACCACGGT
    EG327 ACATCACAAG CGACACCAAA GGCTTGAATT TCGCGAAAAA ACGGCTGAG ACCAACGGCG ACACCACGGT
Consensus ACATCA-AAG CGACACCAAA GGCTTGAATT T-GCGAAA-A AACGGCTG-G AC-AACGGCG AC-CCACGGT
                                           C3

561                                                                       630
     H15  TCATCTGAAC GGTATCGGTT CGACTTTGAC CGATACGCTG CTGAATACCG GAGCGACCAC AAACGTAACC
     BZ10 TCATCTGAAC GGTATCGGTT CGACTTTGAC CGATACGCTG CTGAATACCG GAGCGACCAC AAACGTAACC
    BZ198 TCATCTGAAC GGTATCGGTT CGACTTTGAC CGATACGCTG CTGAATACCG GAGCGACCAC AAACGTAACC
     P20  TCATCTGAAC GGTATCGGTT CGACTTTGAC CGATACGCTT GCGGTTCTT CTGCTTCTCA CGTTGATGCG
     H38  TCATCTGAAC GGTATTGGTT CGACTTTGAC CGATACGCTG CTGAATACCG GAGCGACCAC AAACGTAACC
    Z2491 TCATCTGAAC GGTATCGGTT CGACTTTGAC CGATACGCTT GCGGTTCTT CTGCTTCTCA CGTTGATGCG
     H41  TCATCTGAAC GGTATCGGTT CGACTTTGAC CGATATGCTG CTGAATACCG GAGCGACCAC AAACGTAACC
    EG329 TCATCTGAAC GGTATTGGTT CGACTTTGAC CGATACGCTG CTGAATACCG GAGCGACCAC AAACGTAACC
    PMC21 TCATCTGAAC GGTATTGGTT CGACTTTGAC CGATACGCTG CTGAATACCG GAGCGACCAC AAACGTAACC
    EG327 TCATCTGAAC GGTATCGGTT CGACTTTGAC CGATACGCTG CTGAATACCG GAGCGACCAC AAACGTAACC
Consensus TCATCTGAAC GGTAT-GGTT CGACTTTGAC CGATA-GCT- --G--T-C-- --GC--C--- ----G---C-
                    C3                                          V3
```

FIG. 2C

```
             631                                                                              700
      H15    AACGACAACG TTACCGATGA CGAGAAAAAA CGTGCGGCAA GCGTTAAAGA CGTATTAAAC GCAGGCTGGA
      BZ10   AACGACAACG TTACCGATGA CGAGAAAAAA CGTGCGGCAA GCGTTAAAGA CGTATTAAAC GCAGGCTGGA
      BZ198  AACGACAACG TTACCGATGA CGAGAAAAAA CGTGCGGCAA GCGTTAAAGA CGTATTAAAC GCAGGCTGGA
      P20    GGTAACCAAA GTACACATTA C......ACT CGTGCAGCAA GTATTAAGGA TGTGTTGAAT GCGGGTTGGA
      H38    AACGACAACG TTACCGATGA CAAGAAAAAA CGTGCGGCAA GCGTTAAAGA CGTATTAAAC GCAGGCTGGA
      Z2491  GGTAACCAAA GTACACATTA C......ACT CGTGCAGCAA GTATTAAGGA TGTGTTGAAT GCGGGTTGGA
      H41    AACGACAACG TTACCGATGA CGAGAAAAAA CGTGCGGCAA GCGTTAAAGA CGTATTAAAC GCAGGCTGGA
      EG329  AACGACAACG TTACCGATGA CGAGAAAAAA CGTGCGGCAA GCGTTAAAGA CGTATTAAAC GCTGGCTGGA
      PMC21  AACGACAACG TTACCGATGA CGAGAAAAAA CGTGCGGCAA GCGTTAAAGA CGTATTAAAC GCTGGCTGGA
      EG327  AACGACAACG TTACCGATGA CGAGAAAAAA CGTGCGGCAA GCGTTAAAGA CGTATTAAAC GCAGGCTGGA
  Consensus  ----AC-A-- -TAC--AT-A C------A-- CGTGC-GCAA G--TTAA-GA -GT-TT-AA- GC-GG-TGGA
                               V3                                            C4

701                                                                              770
      H15    ACATTAAAGG CGTTAAACCC GGTACAACAG CT......TC CGATAACGTT GATTTCGTCC GCACTTACGA
      BZ10   ACATTAAAGG CGTTAAACCC GGTACAACAG CT......TC CGATAACGTC GATTTCGTCC GCACTTACGA
      BZ198  ACATTAAAGG CGTTAAACCC GGTACAACAG CT......TC CGATAACGTT GATTTCGTCC GCACTTACGA
      P20    ATATTAAGGG TGTTAAAACT GGCTCAACAA CTGGTCAATC AGAAAATGTC GATTTCGTCC GCACTTACGA
      H38    ACATTAAAGG CGTTAAACCC GGTACAACAG CT......TC CGATAACGTT GATTTCGTCC ACACTTACGA
      Z2491  ATATTAAGGG TGTTAAAACT GGCTCAACAA CTGGTCAATC AGAAAATGTC GATTTCGTCC GCACTTACGA
      H41    ACATTAAAGG CGTTAAACCC GGTACAACAG CT......TC CGATAACGTT GATTTCGTCC GCACTTACGA
      EG329  ACATTAAAGG CGTTAAACCC GGTACAACAG CT......TC CGATAACGTT GATTTCGTCC GCACTTACGA
      PMC21  ACATTAAAGG CGTTAAACCC GGTACAACAG CT......TC CGATAACGTT GATTTCGTCC GCACTTACGA
      EG327  ACATTAAAGG CGTTAAACCC GGTACAACAG CT......TC CGATAACGTT GATTTCGTCC GCACTTACGA
  Consensus  A-ATTAA-GG -GTTAAA-C- GG--CAACA- CT------TC -GA-AA-GT- GATTTCGTCC -CACTTACGA
                  C4                             V4                            C5

771                                                                              840
      H15    CACAGTCGAG TTCTTGAGCG CAGATACGAA AACAACGACT GTTAATGTGG AAAGCAAAGA CAACGGCAAG
      BZ10   CACAGTCGAG TTCTTGAGCG CAGATACGAA AACAACGACT GTTAATGTGG AAAGCAAAGA CAACGGCAAG
      BZ198  CACAGTCGAG TTCTTGAGCG CAGATACGAA AACAACGACT GTTAATGTGG AAAGCAAAGA CAACGGCAAG
      P20    CACAGTCGAG TTCTTGAGCG CAGATACGAA AACAACGACT GTTAATGTGG AAAGCAAAGA CAACGGCAAG
      H38    CACAGTCGAG TTCTTGAGCG CAGATACGAA AACAACGACT GTTAATGTGG AAAGCAAAGA CAACGGCAAG
      Z2491  CACAGTCGAG TTCTTGAGCG CAGATACGAA AACAACGACT GTTAATGTGG AAAGCAAAGA CAACGGCAAG
      H41    CACAGTCGAG TTCTTGAGCG CAGATACGAA AACAACGACT GTTAATGTGG AAAGCAAAGA CAACGGCAAG
      EG329  CACAGTCGAG TTCTTGAGCG CAGATACGAA AACAACGACT GTTAATGTGG AAAGCAAAGA CAACGGCAAG
      PMC21  CACAGTCGAG TTCTTGAGCG CAGATACGAA AACAACGACT GTTAATGTGG AAAGCAAAGA CAACGGCAAG
      EG327  CACAGTCGAG TTCTTGAGCG CAGATACGAA AACAACGACT GTTAATGTGG AAAGCAAAGA CAACGGCAAG
  Consensus  CACAGTCGAG TTCTTGAGCG CAGATACGAA AACAACGACT GTTAATGTGG AAAGCAAAGA CAACGGCAAG
                                                C5

841                                                                              910
      H15    AAAACCGAAG TTAAAATCGG TGCGAAGACT TCTGTTATTA AAGAAAAAGA CGGTAAGTTG GTTACTGGTA
      BZ10   AGAACCGAAG TTAAAATCGG TGCGAAGACT TCTGTTATTA AAGAAAAAGA CGGTAAGTTG GTTACTGGTA
      BZ198  AAAACCGAAG TTAAAATCGG TGCGAAGACT TCTGTTATTA AAGAAAAAGA CGGTAAGTTG GTTACTGGTA
      P20    AGAACCGAAG TTAAAATCGG TGCGAAGACT TCTGTTATTA AAGAAAAAGA CGGTAAGTTG GTTACTGGTA
      H38    AGAACCGAAG TTAAAATCGG TGCGAAGACT TCTGTTATTA AAGAAAAAGA CGGTAAGTTG GTTACTGGTA
      Z2491  AGAACCGAAG TTAAAATCGG TGCGAAGACT TCTGTTATTA AAGAAAAAGA CGGTAAGTTG GTTACTGGTA
      H41    AAAACCGAAG TTAAAATCGG TGCGAAGACT TCTGTTATTA AAGAAAAAGA CGGTAAGTTG GTTACTGGTA
      EG329  AAAACCGAAG TTAAAATCGG TGCGAAGACT TCTGTTATTA AAGAAAAAGA CGGTAAGTTG GTTACTGGTA
      PMC21  AAAACCGAAG TTAAAATCGG TGCGAAGACT TCTGTTATTA AAGAAAAAGA CGGTAAGTTG GTTACTGGTA
      EG327  AGAACCGAAG TTAAAATCGG TGCGAAGACT TCTGTTATCA AAGAAAAAGA CGGTAAGTTG GTTACTGGTA
  Consensus  A-AACCGAAG TTAAAATCGG TGCGAAGACT TCTGTTAT-A AAGAAAAAGA CGGTAAGTTG GTTACTGGTA
                                                C5
```

FIG. 2D

```
           911                                                                           980
      H15  AAGGCAAAGA CGAGAATGGT TCTTCTACAG ACGAAGGCGA AGGCTTAGTG ACTGCAAAAG AAGTGATTGA
     BZ10  AAGGCAAAGG CGAGAATGGT TCTTCTACAG ACGAAGGCGA AGGCTTAGTG ACTGCAAAAG AAGTGATTGA
    BZ198  AAGGCAAAGA CGAGAATGGT TCTTCTACAG ACGAAGGCGA AGGCTTAGTG ACTGCAAAAG AAGTGATTGA
      P20  AAGGCAAAGG CGAGAATGGT TCTTCTACAG ACGAAGGCGA AGGCTTAGTG ACTGCAAAAG AAGTGATTGA
      H38  AAGGCAAAGG CGAGAATGGT TCTTCTACAG ACGAAGGCGA AGGCTTAGTG ACTGCAAAAG AAGTGATTGA
    Z2491  AAGGCAAAGG CGAGAATGGT TCTTCTACAG ACGAAGGCGA AGGCTTAGTG ACTGCAAAAG AAGTGATTGA
      H41  AAGGCAAAGG CGAGAATGGT TCTTCTACAG ACGAAGGCGA AGGCTTAGTG ACTGCAAAAG AAGTGATTGA
    EG329  AAGACAAAGG CGAGAATGGT TCTTCTACAG ACGAAGGCGA AGGCTTAGTG ACTGCAAAAG AAGTGATTGA
    PMC21  AAGACAAAGG CGAGAATGGT TCTTCTACAG ACGAAGGCGA AGGCTTAGTG ACTGCAAAAG AAGTGATTGA
    EG327  AAGACAAAGG CGAGAATGAT TCTTCTACAG ACAAAGGCGA AGGCTTAGTG ACTGCAAAAG AAGTGATTGA
Consensus  AAG-CAAAG- CGAGAATG-T TCTTCTACAG AC-AAGGCGA AGGCTTAGTG ACTGCAAAAG AAGTGATTGA
                                              C5

981                                                                          1050
      H15  TGCAGTAAAC AAGGCTGGTT GGAGAATGAA AACAACAACC GCTAATGGTC AAACAGGTCA AGCTGACAAG
     BZ10  TGCAGTAAAC AAGGCTGGTT GGAGAATGAA AACAACAACC GCTAATGGTC AAACAGGTCA AGCTGACAAG
    BZ198  TGCAGTAAAC AAGGCTGGTT GGAGAATGAA AACAACAACC GCTAATGGTC AAACAGGTCA AGCTGACAAG
      P20  TGCAGTAAAC AAGGCTGGTT GGAGAATGAA AACAACAACC GCTAATGGTC AAACAGGTCA AGCTGACAAG
      H38  TGCAGTAAAC AAGGCTGGTT GGAGAATGAA AACAACAACC GCTAATGGTC AAACAGGTCA AGCTGACAAG
    Z2491  TGCAGTAAAC AAGGCTGGTT GGAGAATGAA AACAACAACC GCTAATGGTC AAACAGGTCA AGCTGACAAG
      H41  TGCAGTAAAC AAGGCTGGTT GGAGAATGAA AACAACAACC GCTAATGGTC AAACAGGTCA AGCTGACAAG
    EG329  TGCAGTAAAC AAGGCTGGTT GGAGAATGAA AACAACAACC GCTAATGGTC AAACAGGTCA AGCTGACAAG
    PMC21  TGCAGTAAAC AAGGCTGGTT GGAGAATGAA AACAACAACC GCTAATGGTC AAACAGGTCA AGCTGACAAG
    EG327  TGCAGTAAAC AAGGCTGGTT GGAGAATGAA AACAACAACC GCTAATGGTC AAACAGGTCA AGCTGACAAG
Consensus  TGCAGTAAAC AAGGCTGGTT GGAGAATGAA AACAACAACC GCTAATGGTC AAACAGGTCA AGCTGACAAG
                                              C5

1051                                                                          1120
      H15  TTTGAAACCG TTACATCAGG CACAAAAGTA ACCTTTGCTA GTGGTAATGG TACAACTGCG ACTGTAAGTA
     BZ10  TTTGAAACCG TTACATCAGG CACAAAAGTA ACCTTTGCTA GTGGTAATGG TACAACTGCG ACTGTAAGTA
    BZ198  TTTGAAACCG TTACATCAGG CACAAATGTA ACCTTTGCTA GTGGTAAAGG TACAACTGCG ACTGTAAGTA
      P20  TTTGAAACCG TTACATCAGG CACAAATGTA ACCTTTGCTA GTGGTAATGG TACAACTGCG ACTGTAAGTA
      H38  TTTGAAACCG TTACATCAGG CACAAATGTA ACCTTTGCTA GTGGTAAAGG TACAACTGCG ACTGTAAGTA
    Z2491  TTTGAAACCG TTACATCAGG CACAAATGTA ACCTTTGCTA GTGGTAAAGG TACAACTGCG ACTGTAAGTA
      H41  TTTGAAACCG TTACATCAGG CACAAAAGTA ACCTTTGCTA GTGGTAATGG TACAACTGCG ACTGTAAGTA
    EG329  TTTGAAACCG TTACATCAGG CACAAATGTA ACCTTTGCTA GTGGTAAAGG TACAACTGCG ACTGTAAGTA
    PMC21  TTTGAAACCG TTACATCAGG CACAAAAGTA ACCTTTGCTA GTGGTAATGG TACAACTGCG ACTGTAAGTA
    EG327  TTTGAAACCG TTACATCAGG CACAAATGTA ACCTTTGCTA GTGGTAAAGG TACAACTGCG ACTGTAAGTA
Consensus  TTTGAAACCG TTACATCAGG CACAAA-GTA ACCTTTGCTA GTGGTAA-GG TACAACTGCG ACTGTAAGTA
                                              C5

1121                                                                          1190
      H15  AAGATGATCA AGGCAACATC ACTGTTAAGT ATGATGTAAA TGTCGGCGAT GCCCTAAACG TCAATCAGCT
     BZ10  AAGATGATCA AGGCAACATC ACTGTTAAGT ATGATGTAAA TGTCGGCGAT GCCCTAAACG TCAATCAGCT
    BZ198  AAGATGATCA AGGCAACATC ACTGTTAAGT ATGATGTAAA TGTCGGCGAT GCCCTAAACG TCAATCAGCT
      P20  AAGATGATCA AGGCAACATC ACTGTTAAGT ATGATGTAAA TGTCGGCGAT GCCCTAAACG TCAATCAGCT
      H38  AAGATGATCA AGGCAACATC ACTGTTAAGT ATGATGTAAA TGTCGGCGAT GCCCTAAACG TCAATCAGCT
    Z2491  AAGATGATCA AGGCAACATC ACTGTTATGT ATGATGTAAA TGTCGGCGAT GCCCTAAACG TCAATCAGCT
      H41  AAGATGATCA AGGCAACATC ACTGTTAAGT ATGATGTAAA TGTCGGCGAT GCCCTAAACG TCAATCAGCT
    EG329  AAGATGATCA AGGCAACATC ACTGTTATGT ATGATGTAAA TGTCGGCGAT GCCCTAAACG TCAATCAGCT
    PMC21  AAGATGATCA AGGCAACATC ACTGTTATGT ATGATGTAAA TGTCGGCGAT GCCCTAAACG TCAATCAGCT
    EG327  AAGATGATCA AGGCAACATC ACTGTTATGT ATGATGTAAA TGTCGGCGAT GCCCTAAACG TCAATCAGCT
Consensus  AAGATGATCA AGGCAACATC ACTGTTA-GT ATGATGTAAA TGTCGGCGAT GCCCTAAACG TCAATCAGCT
                                              C5
```

FIG. 2E

```
            1191                                                                        1260
     H15    GCAAAACAGC  GGTTGGAATT  TGGATTCCAA  AGCGGTTGCA  GGTTCTTCGG  GCAAAGTCAT  CAGCCGGCAAT
     BZ10   GCAAAACAGC  GGTTGGAATT  TGGATTCCAA  AGCGGTTGCA  GGTTCTTCGG  GCAAAGTCAT  CAGCGGCAAT
     BZ198  GCAAAACAGC  GGTTGGAATT  TGGATTCCAA  AGCGGTTGCA  GGTTCTTCGG  GCAAAGTCAT  CAGCGGCAAT
     P20    GCAAAACAGC  GGTTGGAATT  TGGATTCCAA  AGCGGTTGCA  GGTTCTTCGG  GCAAAGTCAT  CAGCGGCAAT
     H38    GCAAAACAGC  GGTTGGAATT  TGGATTCCAA  AGCGGTTGCA  GGTTCTTCGG  GCAAAGTCAT  CAGCGGCAAT
     Z2491  GCAAAACAGC  GGTTGGAATT  TGGATTCCAA  AGCGGTTGCA  GGTTCTTCGG  GCAAAGTCAT  CAGCGGCAAT
     H41    GCAAAACAGC  GGTTGGAATT  TGGATTCCAA  AGCGGTTGCA  GGTTCTTCGG  GCAAAGTCAT  CAGCGGCAAT
     EG329  GCAAAACAGC  GGTTGGAATT  TGGATTCCAA  AGCGGTTGCA  GGTTCTTCGG  GCAAAGTCAT  CAGCGGCAAT
     PMC21  GCAAAACAGC  GGTTGGAATT  TGGATTCCAA  AGCGGTTGCA  GGTTCTTCGG  GCAAAGTCAT  CAGCGGCAAT
     EG327  GCAAAACAGC  GGTTGGAATT  TGGATTCCAA  AGCGGTTGCA  GGTTCTTCGG  GCAAAGTCAT  CAGCGGCAAT
  Consensus GCAAAACAGC  GGTTGGAATT  TGGATTCCAA  AGCGGTTGCA  GGTTCTTCGG  GCAAAGTCAT  CAGCGGCAAT
                                                C5

1261                                                                        1330
     H15    GTTTCGCCGA  GCAAGGGAAA  GATGGATGAA  ACCGTCAACA  TTAATGCCGG  CAACAACATC  GAGATTACCC
     BZ10   GTTTCGCCGA  GCAAGGGAAA  GATGGATGAA  ACCGTCAACA  TTAATGCCGG  CAACAACATC  GAGATTACCC
     BZ198  GTTTCGCCGA  GCAAGGGAAA  GATGGATGAA  ACCGTCAACA  TTAATGCCGG  CAACAACATC  GAGATTACCC
     P20    GTTTCGCCGA  GCAAGGGAAA  GATGGATGAA  ACCGTCAACA  TTAATGCCGG  CAACAACATC  GAGATTACCC
     H38    GTTTCGCCGA  GCAAGGGAAA  GATGGATGAA  ACCGTCAACA  TTAATGCCGG  CAACAACATC  GAGATTACCC
     Z2491  GTTTCGCCGA  GCAAGGGAAA  GATGGATGAA  ACCGTCAACA  TTAATGCCGG  CAACAACATC  GAGATTAGCC
     H41    GTTTCGCCGA  GCAAGGGAAA  GATGGATGAA  ACCGTCAACA  TTAATGCCGG  CAACAACATC  GAGATTACCC
     EG329  GTTTCGCCGA  GCAAGGGAAA  GATGGATGAA  ACCGTCAACA  TTAATGCCGG  CAACAACATC  GAGATTACCC
     PMC21  GTTTCGCCGA  GCAAGGGAAA  GATGGATGAA  ACCGTCAACA  TTAATGCCGG  CAACAACATC  GAGATTACCC
     EG327  GTTTCGCCGA  GCAAGGGAAA  GATGGATGAA  ACCGTCAACA  TTAATGCCGG  CAACAACATC  GAGATTACCC
  Consensus GTTTCGCCGA  GCAAGGGAAA  GATGGATGAA  ACCGTCAACA  TTAATGCCGG  CAACAACATC  GAGATTA-CC
                                                C5

1331                                                                        1400
     H15    GCAACGGCAA  AAATATCGAC  ATCGCCACTT  CGATGACCCC  GCAATTTTCC  AGCGTTTCGC  TCGGCGCGGG
     BZ10   GCAACGGCAA  AAATATCGAC  ATCGCCACTT  CGATGACCCC  GCAATTTTCC  AGCGTTTCGC  TCGGCGCGGG
     BZ198  GCAACGGTAA  AAATATCGAC  ATCGCCACTT  CGATGGCGCC  GCAGTTTTCC  AGCGTTTCGC  TCGGTGCGGG
     P20    GCAACGGCAA  AAATATCGAC  ATCGCCACTT  CGATGACCCC  GCAATTTTCC  AGCGTTTCGC  TCGGCGCGGG
     H38    GCAACGGTAA  AAATATCGAC  ATCGCCACTT  CGATGACCCC  GCAGTTTTCC  AGCGTTTCGC  TCGGCGCGGG
     Z2491  GCAACGGTAA  AAATATCGAC  ATCGCCACTT  CGATGGCGCC  GCAGTTTTCC  AGCGTTTCGC  TCGGCGCGGG
     H41    GCAACGGCAA  AAATATCGAC  ATCGCCACTT  CGATGACCCC  GCAATTTTCC  AGCGTTTCGC  TCGGCGCGGG
     EG329  GCAACGGTAA  AAATATCGAC  ATCGCCACTT  CGATGACCCC  GCAGTTTTCC  AGCGTTTCGC  TCGGCGCGGG
     PMC21  GCAACGGTAA  AAATATCGAC  ATCGCCACTT  CGATGACCCC  GCAGTTTTCC  AGCGTTTCGC  TCGGCGCGGG
     EG327  GCAACGGCAA  AAATATCGAC  ATCGCCACTT  CGATGACCCC  GCAATTTTCC  AGCGTTTCGC  TCGGCGCGGG
  Consensus GCAACGG-AA  AAATATCGAC  ATCGCCACTT  CGATG-C-CC  GCA-TTTTCC  AGCGTTTCGC  TCGG-GCGGG
                                                C5

1401                                                                        1470
     H15    GGCGGATGCG  CCCACTTTAA  GCGTGGATGA  CGAGGGCGCG  TTGAATGTCG  GCAGCAAGGA  TGCCAACAAA
     BZ10   GGCGGATGCG  CCCACTTTAA  GCGTGGATGA  CGAGGGCGCG  TTGAATGTCG  GCAGCAAGGA  TGCCAACAAA
     BZ198  GGCGGATGCG  CCCACTTTGA  GCGTGGATCA  CGAGGGCGCG  TTGAATGTCG  GCAGCAAGGA  TACCAACAAA
     P20    GCCGGATGCG  CCCACTTTAA  GCGTGGATGA  CGAGGGCGCG  TTGAATGTCG  GCAGCAAGGA  TGCCAACAAA
     H38    GCCGGATGCG  CCCACTTTGA  GCGTGGATGA  CAAGGGCGCG  TTGAATGTCG  GCAGCAAGGA  TGCCAACAAA
     Z2491  GGCAGATGCG  CCCACTTTAA  GCGTGGATGA  CGAGGGCGCG  TTGAATGTCG  GCAGCAAGGA  TGCCAACAAA
     H41    GGCGGATGCG  CCCACTTTAA  GCGTGGATGA  CGAGGGCGCG  TTGAATGTCG  GCAGCAAGGA  TGCCAACAAA
     EG329  GGCGGATGCG  CCCACTTTGA  GCGTGGAT..  .GGGGACGCA  TTGAATGTCG  GCAGCAAGAA  GGACAACAAA
     PMC21  GGCGGATGCG  CCCACTTTGA  GCGTGGAT..  .GGGGACGCA  TTGAATGTCG  GCAGCAAGAA  GGACAACAAA
     EG327  GGCGGATGCG  CCCACTTTAA  GCGTGGATGA  CGAGGGCGCG  TTGAATGTCG  GCAGCAAGGA  TGCCAACAAA
  Consensus GGC-GATGCG  CCCACTTT-A  GCGTGGAT--  ----GG-CGC-  TTGAATGTCG  GCAGCAAG-A  ---CAACAAA
                                                C5
```

FIG. 2F

```
            1471                                                                                  1540
     H15    CCCGTCCGCA TTACCAATGT CGCCCCGGGC GTTAAAGAGG GGGATGTTAC AAACGTCGCA CAACTTAAAG
     BZ10   CCCGTCCGCA TTACCAATGT CGCCCCGGGC GTTAAAGAGG GGGATGTTAC AAACGTCGCA CAACTTAAAG
     BZ198  CCCGTCCGCA TTACCAATGT CGCCCCGGGC GTTAAAGAGG GGGATGTTAC AAACGTCGCA CAACTTAAAG
     P20    CCCGTCCGCA TTACCAATGT CGCCCCGGGC GTTAAAGAGG GGGATGTTAC AAACGTCGCA CAACTTAAAG
     H38    CCCGTCCGCA TTACCAATGT CGCCCCGGGC GTTAAAGAGG GGGATGTTAC AAACGTCGCA CAACTTAAAG
     Z2491  CCCGTCCGCA TTACCAATGT CGCCCCGGGC GTTAAAGAGG GGGATGTTAC AAACGTCGCA CAACTTAAAG
     H41    CCCGTCCGCA TTACCAATGT CGCCCCGGGC GTTAAAGAGG GGGATGTTAC AAACGTCGCG CAACTTAAAG
     EG329  CCCGTCCGCA TTACCAATGT CGCCCCGGGC GTTAAAGAGG GGGATGTTAC AAACGTCGCA CAACTTAAAG
     PMC21  CCCGTCCGCA TTACCAATGT CGCCCCGGGC GTTAAAGAGG GGGATGTTAC AAACGTCGCA CAACTTAAAG
     EG327  CCCGTCCGCA TTACCAATGT CGCCCCGGGC GTTAAAGAGG GGGATGTTAC AAACGTCGCA CAACTTAAAG
 Consensus  CCCGTCCGCA TTACCAATGT CGCCCCGGGC GTTAAAGAGG GGGATGTTAC AAACGTCGC- CAACTTAAAG
                                                  C5

1541                                                                                  1610
     H15    GTGTGGCGCA AAACTTGAAC AACCGCATCG ACAATGTGGA CGGCAACGCG CGCGCGGGTA TCGCCCAAGC
     BZ10   GTGTGGCGCA AAACTTGAAC AACCGCATCG ACAATGTGGA CGGCAACGCG CGCGCGGGTA TCGCCCAAGC
     BZ198  GCGTGGCGCA AAACTTGAAC AACCGCATCG ACAATGTGGA CGGCAACGCG CGTGCGGGCA TCGCCCAAGC
     P20    GTGTGGCGCA AAACTTGAAC AACCGCATCG ACAATGTGAA CGGCAACGCG CGCGCGGGTA TCGCCCAAGC
     H38    GCGTGGCGCA AAACTTGAAC AACCGCATCG ACAATGTGGA CGGCAACGCG CGTGCGGGCA TCGCCCAAGC
     Z2491  GCGTGGCGCA AAACTTGAAC AACCGCATCG ACAATGTGGA CGGCAACGCG CGTGCGGGCA TCGCCCAAGC
     H41    GTGTGGCGCA AAACTTGAAC AACCGCATCG ACAATGTGAA CGGCAACGCG CGTGCGGGCA TCGCCCAAGC
     EG329  GCGTGGCGCA AAACTTGAAC AACCGCATCG ACAATGTGGA CGGCAACGCG CGTGCGGGCA TCGCCCAAGC
     PMC21  GCGTGGCGCA AAACTTGAAC AACCGCATCG ACAATGTGGA CGGCAACGCG CGTGCGGGCA TCGCCCAAGC
     EG327  GCGTGGCGCA AAACTTGAAC AACCACATCG ACAATGTGGA CGGCAACGCG CGTGCGGGCA TCGCCCAAGC
 Consensus  G-GTGGCGCA AAACTTGAAC AACC-CATCG ACAATGTG-A CGGCAACGCG CG-GCGGG-A TCGCCCAAGC
                                                  C5

1611                                                                                  1680
     H15    GATTGCAACC GCAGGTTTGG CTCAGGCGTA TTTGCCCGGC AAGAGTATGA TGGCGATCGG CGGCGGTACT
     BZ10   GATTGCAACC GCAGGTTTGG CTCAGGCCTA TTTGCCCGGC AAGAGTATGA TGGCGATCGG CGGCGGTACT
     BZ198  GATTGCAACC GCAGGTCTAG TTCAGGCGTA TCTGCCCGGC AAGAGTATGA TGGCGATCGG CGGCGACACT
     P20    GATTGCAACC GCAGGTTTGG CTCAGGCCTA TTTGCCCGGC AAGAGTATGA TGGCGATCGG CGGCGGTACT
     H38    GATTGCAACC GCAGGTCTGG TTCAGGCGTA TCTGCCCGGC AAGAGTATGA TGGCGATCGG CGGCGGCACT
     Z2491  GATTGCAACC GCAGGTCTGG TTCAGGCGTA TCTGCCCGGC AAGAGTATGA TGGCGATCGG CGGCGGCACT
     H41    GATTGCAACC GCAGGTCTGG TTCAGGCGTA TCTGCCCGGC AAGAGTATGA TGGCGATCGG CGGCGGCACT
     EG329  GATTGCAACC GCAGGTCTGG TTCAGGCGTA TTTGCCCGGC AAGAGTATGA TGGCGATCGG CGGCGGCACT
     PMC21  GATTGCAACC GCAGGTCTGG TTCAGGCGTA TTTGCCCGGC AAGAGTATGA TGGCGATCGG CGGCGGCACT
     EG327  GATTGCAACC GCAGGTCTGG TTCAGGCGTA TCTGCCCGGC AAGAGTATGA TGGCGATCGG CGGCGGCACT
 Consensus  GATTGCAACC GCAGGT-T-G -TCAGGC-TA T-TGCCCGGC AAGAGTATGA TGGCGATCGG CGGCG--ACT
                                                  C5
```

FIG. 2G

```
              1681
H15        TATCGCGGCG AAGCCGGTTA CGCCATCGGC TACTCGAGCA TTTCTGACAC TGGGAATTGG GTTATCAAGG
B210       TATCGCGGCG AAGCCGGTTA CGCCATCGGC TACTCGAGCA TTTCTGACAC TGGGAATTGG GTTATCAAGG
B2198      TATCGCGGCG AAGCCGGTTA CGCCATCGGC TACTCGAAGTA TTTCCGACAC TGGAAATTGG ATTATCAAAG
P20        TATCTCGGCG AAGCCGGTTA CGCCATCGGC TACTCCAGTA TTTCTGACAC TGGGAATTGG GTTATCAAGG
H38        TATCGCGGCG AAGCCGGTTA CGCCATCGGC TACTCCAGTA TTTCCGACGG CGGAAATTGG ATTATCAAAG
Z2491      TATCGCGGCG AAGCCGGTTA TGCCATCGGC TACTCAAGCA TTTCCGACGG CGGAAATTGG ATTATCAAAG
H41        TATCTCGGCG AAGCCGGTTA CGCCATCGGC TACTCCAGTA TTTCCGACGG CGGAAATTGG ATTATCAAAG
EG329      TATCGCGGCG AAGCCGGTTA CGCCATCGGC TACTCCAGTA TTTCCGACGG CGGAAATTGG ATTATCAAAG
PMC21      TATCGCGGCG AAGCCGGTTA CGCCATCGGC TACTCCAGTA TTTCCGACGG CGGAAATTGG ATTATCAAAG
EG327      TATCGCGGCG AAGCCGGTTA TGCCATCGGC TACTCAAGCA TTTCCGACGG CGGAAATTGG ATTATCAAAG
Consensus  TATC-CGGCG AAGCCGGTTA -GCCATCGGC TACTC-AG-A TTTC-G-C-- -GG-AATTGG -TTATCAA-G
                                              C5                                   1750

1751
H15        GCACGGCTTC CGGCAATTCG CGCGGCCATT TCGGTGCTTC GGTTATCAGT GGTAA
B210       GCACGGCTTC CGGCAATTCG CGCGGCCATT TCGGTGCTTC GGTTATCAGT GGTAA
B2198      GCACGGCTTC CGGCAATTCG CGCGGTCATT TCGGTACTTC GGTTATCAGT GGTAA
P20        GCACGGCTTC CGGCAATTCG CGCGGTCATT TCGGTGCTTC GGTTATCAAT GGTAA
H38        GCACGGCTTC CGGCAATTCG CGCGGCCATT TCGGTACTTC GGTTATCAGT GGTAA
Z2491      GCACGGCTTC CGGCAATTCG CGCGGCCATT TCGGTGCTTC GGTTATCAGT GGTAA
H41        GCACGGCTTC CGGCAATTCG CGCGGCCATT TCGGTGCTTC GGTTATCAGT GGTAA
EG329      GCACGGCTTC CGGCAATTCG CGCGGCCATT TCGGTGCTTC GGTTATCAGT GGTAA
PMC21      GCACGGCTTC CGGCAATTCG CGCGGCCATT TCGGTGCTTC GGTTATCAGT GGTAA
EG327      GCACGGCTTC CGGCAATTCG CGCGG-CATT TCGGTGCTTC GGTTATCAGT GGTAA
Consensus  GCACGGCTTC CGGCAATTCG CGCG-G-CATT TCGGT-CTTC GGTTATCA-T GGTAA
                                              C5                      1815
```

FIG. 2H

```
  1  MNKIYRIIWN  SALNAWVVVS  ELTRNHTKRA  SATVKTAVLA  TLLFATVQAS
 51  ANNETDLTSV  GTEKLSFSAN  GNKVNITSDT  KGLNFAKETA  GTNGDTTVHL
101  NGIGSTLTDT  LLNTGATTNV  TNDNVTDDEK  KRAASVKDVL  NAGWNIKGVK
151  PGTTASDNVD  FVRTYDTVEF  LSADTKTTTV  NVESKDNGKK  TEVKIGAKTS
201  VIKEKDGKLV  TGKDKGENGS  STDEGEGLVT  AKEVIDAVNK  AGWRMKTTTA
251  NGQTGQADKF  ETVTSGTNVT  FASGKGTTAT  VSKDDQGNIT  VMYDVNVGDA
301  LNVNQLQNSG  WNLDSKAVAG  SSGKVISGNV  SPSKGKMDET  VNINAGNNIE
351  ITRNGKNIDI  ATSMTPQFSS  VSLGAGADAP  TLSVDGDALN  VGSKKDNKPV
401  RITNVAPGVK  EGDVTNVAQL  KGVAQNLNNR  IDNVDGNARA  GIAQAIATAG
451  LVQAYLPGKS  MMAIGGGTYR  GEAGYAIGYS  SISDGGNWII  KGTASGNSRG
501  HFGASASVGY  QW*
```

FIG. 5A

```
   1  ATGAACAAAA  TATACCGCAT  CATTTGGAAT  AGTGCCCTCA  ATGCATGGGT
  51  CGTCGTATCC  GAGCTCACAC  GCAACCACAC  CAAACGCGCC  TCCGCAACCG
 101  TGAAGACCGC  CGTATTGGCG  ACTCTGTTGT  TTGCAACGGT  TCAGGCAAGT
 151  GCTAACAATG  AAACAGATCT  GACCAGTGTT  GGAACTGAAA  AATTATCGTT
 201  TAGCGCAAAC  GGCAATAAAG  TCAACATCAC  AAGCGACACC  AAAGGCTTGA
 251  ATTTTGCGAA  AGAAACGGCT  GGGACGAACG  GCGACACCAC  GGTTCATCTG
 301  AACGGTATTG  GTTCGACTTT  GACCGATACG  CTGCTGAATA  CCGGAGCGAC
 351  CACAAACGTA  ACCAACGACA  ACGTTACCGA  TGACGAGAAA  AAACGTGCGG
 401  CAAGCGTTAA  AGACGTATTA  AACGCTGGCT  GGAACATTAA  AGGCGTTAAA
 451  CCCGGTACAA  CAGCTTCCGA  TAACGTTGAT  TTCGTCCGCA  CTTACGACAC
 501  AGTCGAGTTC  TTGAGCGCAG  ATACGAAAAC  AACGACTGTT  AATGTGGAAA
 551  GCAAAGACAA  CGGCAAGAAA  ACCGAAGTTA  AAATCGGTGC  GAAGACTTCT
 601  GTTATTAAAG  AAAAAGACGG  TAAGTTGGTT  ACTGGTAAAG  ACAAAGGCGA
 651  GAATGGTTCT  TCTACAGACG  AAGGCGAAGG  CTTAGTGACT  GCAAAAGAAG
 701  TGATTGATGC  AGTAAACAAG  GCTGGTTGGA  GAATGAAAAC  AACAACCGCT
 751  AATGGTCAAA  CAGGTCAAGC  TGACAAGTTT  GAAACCGTTA  CATCAGGCAC
 801  AAATGTAACC  TTTGCTAGTG  GTAAAGGTAC  AACTGCGACT  GTAAGTAAAG
 851  ATGATCAAGG  CAACATCACT  GTTATGTATG  ATGTAAATGT  CGGCGATGCC
 901  CTAAACGTCA  ATCAGCTGCA  AAACAGCGGT  TGGAATTTGG  ATTCCAAAGC
 951  GGTTGCAGGT  TCTTCGGGCA  AAGTCATCAG  CGGCAATGTT  TCGCCGAGCA
1001  AGGGAAAGAT  GGATGAAACC  GTCAACATTA  ATGCCGGCAA  CAACATCGAG
1051  ATTACCCGCA  ACGGTAAAAA  TATCGACATC  GCCACTTCGA  TGACCCCGCA
1101  GTTTTCCAGC  GTTTCGCTCG  GCGCGGGGGC  GGATGCGCCC  ACTTTGAGCG
1151  TGGATGGGGA  CGCATTGAAT  GTCGGCAGCA  AGAAGGACAA  CAAACCCGTC
1201  CGCATTACCA  ATGTCGCCCC  GGGCGTTAAA  GAGGGGGATG  TTACAAACGT
1251  CGCACAACTT  AAAGGCGTGG  CGCAAAACTT  GAACAACCGC  ATCGACAATG
1301  TGGACGGCAA  CGCGCGTGCG  GGCATCGCCC  AAGCGATTGC  AACCGCAGGT
1351  CTGGTTCAGG  CGTATTTGCC  CGGCAAGAGT  ATGATGGCGA  TCGGCGGCGG
1401  CACTTATCGC  GGCGAAGCCG  GTTACGCCAT  CGGCTACTCC  AGTATTTCCG
1451  ACGGCGGAAA  TTGGATTATC  AAAGGCACGG  CTTCCGGCAA  TTCGCGCGGC
1501  CATTTCGGTG  CTTCCGCATC  TGTCGGTTAT  CAGTGGTAA
```

FIG. 5B

```
  1  MNKIYRIIWN  SALNAWVAVS  ELTRNHTKRA  SATVKTAVLA  TLLFATVQAN
 51  ATDETGLINV  ETEKLSFGAN  GKKVNIISDT  KGLNFAKETA  GTNGDTTVHL
101  NGIGSTLTDM  LLNTGATTNV  TNDNVTDDEK  KRAASVKDVL  NAGWNIKGVK
151  PGTTASDNVD  FVRTYDTVEF  LSADTKTTTV  NVESKDNGKK  TEVKIGAKTS
201  VIKEKDGKLV  TGKGKGENGS  STDEGEGLVT  AKEVIDAVNK  AGWRMKTTTA
251  NGQTGQADKF  ETVTSGTKVT  FASGNGTTAT  VSKDDQGNIT  VKYDVNVGDA
301  LNVNQLQNSG  WNLDSKAVAG  SSGKVISGNV  SPSKGKMDET  VNINAGNNIE
351  ITRNGKNIDI  ATSMTPQFSS  VSLGAGADAP  TLSVDDEGAL  NVGSKDANKP
401  VRITNVAPGV  KEGDVTNVAQ  LKGVAQNLNN  RIDNVNGNAR  AGIAQAIATA
451  GLVQAYLPGK  SMMAIGGGTY  LGEAGYAIGY  SSISAGGNWI  IKGTASGNSR
501  GHFGASASVG  YQW*
```

FIG. 6A

```
   1  ATGAACAAAA  TATACCGCAT  CATTTGGAAT  AGTGCCCTCA  ATGCCTGGGT
  51  CGCCGTATCC  GAGCTCACAC  GCAACCACAC  CAAACGCGCC  TCCGCAACCG
 101  TGAAGACCGC  CGTATTGGCG  ACACTGTTGT  TTGCAACGGT  TCAGGCGAAT
 151  GCTACCGATG  AAACAGGCCT  GATCAATGTT  GAAACTGAAA  AATTATCGTT
 201  TGGCGCAAAC  GGCAAGAAAG  TCAACATCAT  AAGCGACACC  AAAGGCTTGA
 251  ATTTCGCGAA  AGAAACGGCT  GGGACGAACG  GCGACACCAC  GGTTCATCTG
 301  AACGGTATCG  GTTCGACTTT  GACCGATATG  CTGCTGAATA  CCGGAGCGAC
 351  CACAAACGTA  ACCAACGACA  ACGTTACCGA  TGACGAGAAA  AAACGTGCGG
 401  CAAGCGTTAA  AGACGTATTA  AACGCAGGCT  GGAACATTAA  AGGCGTTAAA
 451  CCCGGTACAA  CAGCTTCCGA  TAACGTTGAT  TTCGTCCGCA  CTTACGACAC
 501  AGTCGAGTTC  TTGAGCGCAG  ATACGAAAAC  AACGACTGTT  AATGTGGAAA
 551  GCAAGACAA   CGGCAAGAAA  ACCGAAGTTA  AAATCGGTGC  GAAGACTTCT
 601  GTTATTAAAG  AAAAAGACGG  TAAGTTGGTT  ACTGGTAAAG  GCAAAGGCGA
 651  GAATGGTTCT  TCTACAGACG  AAGGCGAAGG  CTTAGTGACT  GCAAAAGAAG
 701  TGATTGATGC  AGTAAACAAG  GCTGGTTGGA  GAATGAAAAC  AACAACCGCT
 751  AATGGTCAAA  CAGGTCAAGC  TGACAAGTTT  GAAACCGTTA  CATCAGGCAC
 801  AAAAGTAACC  TTTGCTAGTG  GTAATGGTAC  AACTGCGACT  GTAAGTAAAG
 851  ATGATCAAGG  CAACATCACT  GTTAAGTATG  ATGTAAATGT  CGGCGATGCC
 901  CTAAACGTCA  ATCAGCTGCA  AAACAGCGGT  TGGAATTTGG  ATTCCAAAGC
 951  GGTTGCAGGT  TCTTCGGGCA  AAGTCATCAG  CGGCAATGTT  TCGCCGAGCA
1001  AGGGAAAGAT  GGATGAAACC  GTCAACATTA  ATGCCGGCAA  CAACATCGAG
1051  ATTACCCGCA  ACGGCAAAAA  TATCGACATC  GCCACTTCGA  TGACCCCGCA
1101  ATTTTCCAGC  GTTTCGCTCG  GCGCGGGGGC  GGATGCGCCC  ACTTTAAGCG
1151  TGGATGACGA  GGGCGCGTTG  AATGTCGGCA  GCAAGGATGC  CAACAAACCC
1201  GTCCGCATTA  CCAATGTCGC  CCCGGGCGTT  AAAGAGGGGG  ATGTTACAAA
1251  CGTCGCGCAA  CTTAAAGGTG  TGGCGCAAAA  CTTGAACAAC  CGCATCGACA
1301  ATGTGAACGG  CAACGCGCGT  GCGGGCATCG  CCCAAGCGAT  TGCAACCGCA
1351  GGTCTGGTTC  AGGCGTATCT  GCCCGGCAAG  AGTATGATGG  CGATCGGCGG
1401  CGGCACTTAT  CTCGGCGAAG  CCGGTTATGC  CATCGGCTAC  TCAAGCATTT
1451  CCGCCGGCGG  AAATTGGATT  ATCAAAGGCA  CGGCTTCCGG  CAATTCGCGC
1501  GGCCATTTCG  GTGCTTCCGC  ATCTGTCGGT  TATCAGTGGT  AA
```

FIG. 6B

```
  1  MNKIYRIIWN  SALNAWVVVS  ELTRNHTKRA  SATVKTAVLA  TLLFATVQAS
 51  ANNVDFVRTY  DTVEFLSADT  KTTTVNVESK  DNGKKTEVKI  GAKTSVIKEK
101  DGKLVTGKDK  GENGSSTDEG  EGLVTAKEVI  DAVNKAGWRM  KTTTANGQTG
151  QADKFETVTS  GTNVTFASGK  GTTATVSKDD  QGNITVMYDV  NVGDALNVNQ
201  LQNSGWNLDS  KAVAGSSGKV  ISGNVSPSKG  KMDETVNINA  GNNIEITRNG
251  KNIDIATSMT  PQFSSVSLGA  GADAPTLSVD  GDALNVGSKK  DNKPVRITNV
301  APGVKEGDVT  NVAQLKGVAQ  NLNNRIDNVD  GNARAGIAQA  IATAGLVQAY
351  LPGKSMMAIG  GGTYRGEAGY  AIGYSSISDG  GNWIIKGTAS  GNSRGHFGAS
401  ASVGYQW*
```

FIG. 7A

```
   1  ATGAACAAAA  TATACCGCAT  CATTTGGAAT  AGTGCCCTCA  ATGCATGGGT
  51  CGTCGTATCC  GAGCTCACAC  GCAACCACAC  CAAACGCGCC  TCCGCAACCG
 101  TGAAGACCGC  CGTATTGGCG  ACTCTGTTGT  TTGCAACGGT  TCAGGCAAGT
 151  GCTAACAACG  TTGATTTCGT  CCGCACTTAC  GACACAGTCG  AGTTCTTGAG
 201  CGCAGATACG  AAAACAACGA  CTGTTAATGT  GGAAAGCAAA  GACAACGGCA
 251  AGAAAACCGA  AGTTAAAATC  GGTGCGAAGA  CTTCTGTTAT  TAAAGAAAAA
 301  GACGGTAAGT  TGGTTACTGG  TAAAGACAAA  GGCGAGAATG  GTTCTTCTAC
 351  AGACGAAGGC  GAAGGCTTAG  TGACTGCAAA  AGAAGTGATT  GATGCAGTAA
 401  ACAAGGCTGG  TTGGAGAATG  AAAACAACAA  CCGCTAATGG  TCAAACAGGT
 451  CAAGCTGACA  AGTTTGAAAC  CGTTACATCA  GGCACAAATG  TAACCTTTGC
 501  TAGTGGTAAA  GGTACAACTG  CGACTGTAAG  TAAAGATGAT  CAAGGCAACA
 551  TCACTGTTAT  GTATGATGTA  AATGTCGGCG  ATGCCCTAAA  CGTCAATCAG
 601  CTGCAAAACA  GCGGTTGGAA  TTTGGATTCC  AAAGCGGTTG  CAGGTTCTTC
 651  GGGCAAAGTC  ATCAGCGGCA  ATGTTTCGCC  GAGCAAGGGA  AAGATGGATG
 701  AAACCGTCAA  CATTAATGCC  GGCAACAACA  TCGAGATTAC  CCGCAACGGT
 751  AAAAATATCG  ACATCGCCAC  TTCGATGACC  CCGCAGTTTT  CCAGCGTTTC
 801  GCTCGGCGCG  GGGGCGGATG  CGCCCACTTT  GAGCGTGGAT  GGGGACGCAT
 851  TGAATGTCGG  CAGCAAGAAG  GACAACAAAC  CGTCCGCAT   TACCAATGTC
 901  GCCCCGGGCG  TTAAGAGGG   GGATGTTACA  AACGTCGCAC  AACTTAAAGG
 951  CGTGGCGCAA  AACTTGAACA  ACCGCATCGA  CAATGTGGAC  GGCAACGCGC
1001  GTGCGGGCAT  CGCCCAAGCG  ATTGCAACCG  CAGGTCTGGT  TCAGGCGTAT
1051  TTGCCCGGCA  AGAGTATGAT  GGCGATCGGC  GGCGGCACTT  ATCGCGGCGA
1101  AGCCGGTTAC  GCCATCGGCT  ACTCCAGTAT  TTCCGACGGC  GGAAATTGGA
1151  TTATCAAAGG  CACGGCTTCC  GGCAATTCGC  GCGGCCATTT  CGGTGCTTCC
1201  GCATCTGTCG  GTTATCAGTG  GTAA
```

FIG. 7B

```
  1  MNKIYRIIWN  SALNAWVVVS  ELTRNHTKRA  SATVKTAVLA  TLLFATVQAS
 51  ANRAASVKDV  LNAGWNIKGV  KPGTTASDNV  DFVRTYDTVE  FLSADTKTTT
101  VNVESKDNGK  KTEVKIGAKT  SVIKEKDGKL  VTGKDKGENG  SSTDEGEGLV
151  TAKEVIDAVN  KAGWRMKTTT  ANGQTGQADK  FETVTSGTNV  TFASGKGTTA
201  TVSKDDQGNI  TVMYDVNVGD  ALNVNQLQNS  GWNLDSKAVA  GSSGKVISGN
251  VSPSKGKMDE  TVNINAGNNI  EITRNGKNID  IATSMTPQFS  SVSLGAGADA
301  PTLSVDGDAL  NVGSKKDNKP  VRITNVAPGV  KEGDVTNVAQ  LKGVAQNLNN
351  RIDNVDGNAR  AGIAQAIATA  GLVQAYLPGK  SMMAIGGGTY  RGEAGYAIGY
401  SSISDGGNWI  IKGTASGNSR  GHFGASASVG  YQW*
```

FIG. 8A

```
   1  ATGAACAAAA  TATACCGCAT  CATTTGGAAT  AGTGCCCTCA  ATGCATGGGT
  51  CGTCGTATCC  GAGCTCACAC  GCAACCACAC  CAAACGCGCC  TCCGCAACCG
 101  TGAAGACCGC  CGTATTGGCG  ACTCTGTTGT  TTGCAACGGT  TCAGGCAAGT
 151  GCTAACCGTG  CGGCAAGCGT  TAAAGACGTA  TTAAACGCTG  GCTGGAACAT
 201  TAAAGGCGTT  AAACCCGGTA  CAACAGCTTC  CGATAACGTT  GATTTCGTCC
 251  GCACTTACGA  CACAGTCGAG  TTCTTGAGCG  CAGATACGAA  AACAACGACT
 301  GTTAATGTGG  AAAGCAAAGA  CAACGGCAAG  AAAACCGAAG  TTAAAATCGG
 351  TGCGAAGACT  TCTGTTATTA  AGAAAAAGA   CGGTAAGTTG  GTTACTGGTA
 401  AAGACAAAGG  CGAGAATGGT  TCTTCTACAG  ACGAAGGCGA  AGGCTTAGTG
 451  ACTGCAAAAG  AAGTGATTGA  TGCAGTAAAC  AAGGCTGGTT  GGAGAATGAA
 501  AACAACAACC  GCTAATGGTC  AAACAGGTCA  AGCTGACAAG  TTTGAAACCG
 551  TTACATCAGG  CACAAATGTA  ACCTTTGCTA  GTGGTAAAGG  TACAACTGCG
 601  ACTGTAAGTA  AAGATGATCA  AGGCAACATC  ACTGTTATGT  ATGATGTAAA
 651  TGTCGGCGAT  GCCCTAAACG  TCAATCAGCT  GCAAAACAGC  GGTTGGAATT
 701  TGGATTCCAA  AGCGGTTGCA  GGTTCTTCGG  GCAAAGTCAT  CAGCGGCAAT
 751  GTTTCGCCGA  GCAAGGGAAA  GATGGATGAA  ACCGTCAACA  TTAATGCCGG
 801  CAACAACATC  GAGATTACCC  GCAACGGTAA  AAATATCGAC  ATCGCCACTT
 851  CGATGACCCC  GCAGTTTTCC  AGCGTTTCGC  TCGGCGCGGG  GGCGGATGCG
 901  CCCACTTTGA  GCGTGGATGG  GGACGCATTG  AATGTCGGCA  GCAAGAAGGA
 951  CAACAAACCC  GTCCGCATTA  CCAATGTCGC  CCCGGGCGTT  AAAGAGGGGG
1001  ATGTTACAAA  CGTCGCACAA  CTTAAAGGCG  TGGCGCAAAA  CTTGAACAAC
1051  CGCATCGACA  ATGTGGACGG  CAACGCGCGT  GCGGGCATCG  CCCAAGCGAT
1101  TGCAACCGCA  GGTCTGGTTC  AGGCGTATTT  GCCCGGCAAG  AGTATGATGG
1151  CGATCGGCGG  CGGCACTTAT  CGCGGCGAAG  CCGGTTACGC  CATCGGCTAC
1201  TCCAGTATTT  CCGACGGCGG  AAATTGGATT  ATCAAAGGCA  CGGCTTCCGG
1251  CAATTCGCGC  GGCCATTTCG  GTGCTTCCGC  ATCTGTCGGT  TATCAGTGGT
1301  AA
```

FIG. 8B

```
  1  MNKIYRIIWN  SALNAWVVVS  ELTRNHTKRA  SATVKTAVLA  TLLFATVQAS
 51  ANTLKAGDNL  KIKQFTYSLK  KDLTDLTSVG  TEKLSFSANG  NKVNITSDTK
101  GLNFAKETAG  TNGDTTVHLN  GIGSTLTDRA  ASVKDVLNAG  WNIKGVKNVD
151  FVRTYDTVEF  LSADTKTTTV  NVESKDNGKK  TEVKIGAKTS  VIKEKDGKLV
201  TGKDKGENGS  STDEGEGLVT  AKEVIDAVNK  AGWRMKTTTA  NGQTGQADKF
251  ETVTSGTNVT  FASGKGTTAT  VSKDDQGNIT  VMYDVNVGDA  LNVNQLQNSG
301  WNLDSKAVAG  SSGKVISGNV  SPSKGKMDET  VNINAGNNIE  ITRNGKNIDI
351  ATSMTPQFSS  VSLGAGADAP  TLSVDGDALN  VGSKKDNKPV  RITNVAPGVK
401  EGDVTNVAQL  KGVAQNLNNR  IDNVDGNARA  GIAQAIATAG  LVQAYLPGKS
451  MMAIGGGTYR  GEAGYAIGYS  SISDGGNWII  KGTASGNSRG  HFGASASVGY
501  QW*
```

FIG. 9A

```
   1  ATGAACAAAA  TATACCGCAT  CATTTGGAAT  AGTGCCCTCA  ATGCATGGGT
  51  CGTCGTATCC  GAGCTCACAC  GCAACCACAC  CAAACGCGCC  TCCGCAACCG
 101  TGAAGACCGC  CGTATTGGCG  ACTCTGTTGT  TTGCAACGGT  TCAGGCAAGT
 151  GCTAACACCC  TCAAAGCCGG  CGACAACCTG  AAAATCAAAC  AATTCACCTA
 201  CTCGCTGAAA  AAAGACCTCA  CAGATCTGAC  CAGTGTTGGA  ACTGAAAAAT
 251  TATCGTTTAG  CGCAAACGGC  AATAAAGTCA  ACATCACAAG  CGACACCAAA
 301  GGCTTGAATT  TTGCGAAAGA  AACGGCTGGG  ACGAACGGCG  ACACCACGGT
 351  TCATCTGAAC  GGTATTGGTT  CGACTTTGAC  CGATCGTGCG  GCAAGCGTTA
 401  AAGACGTATT  AAACGCTGGC  TGGAACATTA  AAGGCGTTAA  AAACGTTGAT
 451  TTCGTCCGCA  CTTACGACAC  AGTCGAGTTC  TTGAGCGCAG  ATACGAAAAC
 501  AACGACTGTT  AATGTGGAAA  GCAAAGACAA  CGGCAAGAAA  ACCGAAGTTA
 551  AAATCGGTGC  GAAGACTTCT  GTTATTAAAG  AAAAAGACGG  TAAGTTGGTT
 601  ACTGGTAAAG  ACAAAGGCGA  GAATGGTTCT  TCTACAGACG  AAGGCGAAGG
 651  CTTAGTGACT  GCAAAAGAAG  TGATTGATGC  AGTAAACAAG  GCTGGTTGGA
 701  GAATGAAAAC  AACAACCGCT  AATGGTCAAA  CAGGTCAAGC  TGACAAGTTT
 751  GAAACCGTTA  CATCAGGCAC  AAATGTAACC  TTTGCTAGTG  GTAAAGGTAC
 801  AACTGCGACT  GTAAGTAAAG  ATGATCAAGG  CAACATCACT  GTTATGTATG
 851  ATGTAAATGT  CGGCGATGCC  CTAAACGTCA  ATCAGCTGCA  AAACAGCGGT
 901  TGGAATTTGG  ATTCCAAAGC  GGTTGCAGGT  TCTTCGGGCA  AAGTCATCAG
 951  CGGCAATGTT  TCGCCGAGCA  AGGGAAAGAT GGATGAAACC  GTCAACATTA
1001  ATGCCGGCAA  CAACATCGAG  ATTACCCGCA  ACGGTAAAAA  TATCGACATC
1051  GCCACTTCGA  TGACCCCGCA  GTTTTCCAGC  GTTTCGCTCG  GCGCGGGGGC
1101  GGATGCGCCC  ACTTTGAGCG  TGGATGGGGA  CGCATTGAAT  GTCGGCAGCA
1151  AGAAGGACAA  CAAACCCGTC  CGCATTACCA  ATGTCGCCCC  GGGCGTTAAA
1201  GAGGGGGATG  TTACAAACGT  CGCACAACTT  AAAGGCGTGG  CGCAAAACTT
1251  GAACAACCGC  ATCGACAATG  TGGACGGCAA  CGCGCGTGCG  GGCATCGCCC
1301  AAGCGATTGC  AACCGCAGGT  CTGGTTCAGG  CGTATTTGCC  CGGCAAGAGT
1351  ATGATGGCGA  TCGGCGGCGG  CACTTATCGC  GGCGAAGCCG  GTTACGCCAT
1401  CGGCTACTCC  AGTATTTCCG  ACGGCGGAAA  TTGGATTATC  AAAGGCACGG
1451  CTTCCGGCAA  TTCGCGCGGC  CATTTCGGTG  CTTCCGCATC  TGTCGGTTAT
1501  CAGTGGTAA
```

FIG. 9B

```
              1                                                             50
H41         MNKIYRIIWN SALNAWVAVS ELTRNHTKRA SATVKTAVLA TLLFATVQAN
PMC21       MNKIYRIIWN SALNAWVVVS DLTRNHTKPA SATVNTAVLA TLLFATVQAS
H41Studel   MNKIYRIIWN SALNAWVAVS ELTRNHTKRA SATVKTAVLA TLLFATVQAN
PMC21Bgldel MNKIYRIIWN SALNAWVVVS ELTRNHTKRA SATVKTAVLA TLLFATVQAS
PMC21C1C5   MNKIYRIIWN SALNAWVVVS ELTRNHTKRA SATVKTAVLA TLLFATVQAS
                                        C1

51                                                            100
H41         ATDED..EEE ELESVQRS.V VGSIQASMEG SVELET...I SLSMTNDSKE
PMC21       ANNEEQEEYL YLHPVQRTVA VLIVNSDKEG AGEKEKVEEN SDWAVYFNEK
H41Studel   ATDE...... .......... .......... .......... ..........
PMC21Bgldel ANNE...... .......... .......... .......... ..........
PMC21C1C5   AN........ .......... .......... .......... ..........
                                        V1

101                                                           150
H41         FVDPYIVVTL KAGDNLKIKQ N.TNENTNAS SFTYSLKKDL TGLINVETEK
PMC21       GVLTAREITL KAGDNLKIKQ NGTN...... .FTYSLKKDL TDLTSVGTEK
H41Studel   .......... .......... .......... .......... TGLINVETEK
PMC21Bgldel .......... .......... .......... .......... TDLTSVGTEK
PMC21C1C5   .......... .......... .......... .......... ..........
            V1         C2         V2                   C3

151                                                           200
H41         LSFGANGKKV NIISDTKGLN FAKETAGTNG DTTVHLNGIG STLTDMLLNT
PMC21       LSFSAHGNKV NITSDTKGLN FAKETAGTNG DTTVHLNGIG STLTDTLLNT
H41Studel   LSFGANGKKV NIISDTKGLN FAKETAGTNG DTTVHLNGIG STLTDMLLNT
PMC21Bgldel LSFSANGNKV NITSDTKGLN FAKETAGTNG DTTVHLNGIG STLTDTLLNT
PMC21C1C5   .......... .......... .......... .......... ..........
                       C3                                        V3

201                                                           250
H41         GATTNVTNDN VTDDEKKRAA SVKDVLNAGW NIKGVKPGTT ASDNVDFVRT
PMC21       GATTNVTNDN VTDDEKKRAA SVKDVLNAGW NIKGVKPGTT ASDNVDFVRT
H41Studel   GATTNVTNDN VTDDEKKRAA SVKDVLNAGW NIKGVKPGTT ASDNVDFVRT
PMC21Bgldel GATTNVTNDN VTDDEKKRAA SVKDVLNAGW NIKGVKPGTT ASDNVDFVRT
PMC21C1C5   .......... .......... .......... .......... ...NVDFVRT
                V3               C4              V4        C5

251                                                           300
H41         YDTVEFLSAD TKTTTVNVES KDNGKKTEVK IGAKTSVIKE KDGKLVTGKG
PMC21       YDTVEFLSAD TKTTTVNVES KDNGKKTEVK IGAKTSVIKE KDGKLVTGKD
H41Studel   YDTVEFLSAD TKTTTVNVES KDNGKKTEVK IGAKTSVIKE KDGKLVTGKG
PMC21Bgldel YDTVEFLSAD TKTTTVNVES KDNGKKTEVK IGAKTSVIKE KDGKLVTGKD
PMC21C1C5   YDTVEFLSAD TKTTTVNVES KDNGKKTEVK IGAKTSVIKE KDGKLVTGKD
                                        C5

301                                                           350
H41         KGENGSSTDE GEGLVTAKEV IDAVNKAGWR MKTTTANGQT GQADKFETVT
PMC21       KGENGSSTDE GEGLVTAKEV IDAVNKAGWR MKTTTANGQT GQADKFETVT
H41Studel   KGENGSSTDE GEGLVTAKEV IDAVNKAGWR MKTTTANGQT GQADKFETVT
PMC21Bgldel KGENGSSTDE GEGLVTAKEV IDAVNKAGWR MKTTTANGQT GQADKFETVT
PMC21C1C5   KGENGSSTDE GEGLVTAKEV IDAVNKAGWR MKTTTANGQT GQADKFETVT
                                        C5

351                                                           400
H41         SGTKVTFASG NGTTATVSKD DQGNITVKYD VNVGDALNVN QLQNSGWNLD
PMC21       SGTNVTFASG KGTTATVSKD DQGNITVMYD VNVGDALNVN QLQNSGWNLD
H41Studel   SGTKVTFASG NGTTATVSKD DQGNITVKYD VNVGDALNVN QLQNSGWNLD
PMC21Bgldel SGTNVTFASG KGTTATVSKD DQGNITVMYD VNVGDALNVN QLQNSGWNLD
PMC21C1C5   SGTNVTFASG KGTTATVSKD DQGNITVMYD VNVGDALNVN QLQNSGWNLD
                                        C5
```

*FIG. 10A*

```
                401                                                    450
      H41   SKAVAGSSGK VISGNVSPSK GKMDETVNIN AGNNIEITRN GKNIDIATSM
     PMC21  SKAVAGSSGK VISGNVSPSK GKMDETVNIN AGNNIEITRN GKNIDIATSM
   H41Studel SKAVAGSSGK VISGNVSPSK GKMDETVNIN AGNNIEITRN GKNIDIATSM
 PMC21Bgldel SKAVAGSSGK VISGNVSPSK GKMDETVNIN AGNNIEITRN GKNIDIATSM
   PMC21C1C5 SKAVAGSSGK VISGNVSPSK GKMDETVNIN AGNNIEITRN GKNIDIATSM
                                              C5

451                                                    500
      H41   TPQFSSVSLG AGADAPTLSV DDEGALNVGS KDANKPVRIT NVAPGVKEGD
     PMC21  TPQFSSVSLG AGADAPTLSV DG.DALNVGS KKDNKPVRIT NVAPGVKEGD
   H41Studel TPQFSSVSLG AGADAPTLSV DDEGALNVGS KDANKPVRIT NVAPGVKEGD
 PMC21Bgldel TPQFSSVSLG AGADAPTLSV DG.DALNVGS KKDNKPVRIT NVAPGVKEGD
   PMC21C1C5 TPQFSSVSLG AGADAPTLSV DG.DALNVGS KKDNKPVRIT NVAPGVKEGD
                                              C5

501                                                    550
      H41   VTNVAQLKGV AQNLNNRIDN VNGNARAGIA QAIATAGLVQ AYLPGKSMMA
     PMC21  VTNVAQLKGV AQNLNNRIDN VDGNARAGIA QAIATAGLVQ AYLPGKSMMA
   H41Studel VTNVAQLKGV AQNLNNRIDN VNGNARAGIA QAIATAGLVQ AYLPGKSMMA
 PMC21Bgldel VTNVAQLKGV AQNLNNRIDN VDGNARAGIA QAIATAGLVQ AYLPGKSMMA
   PMC21C1C5 VTNVAQLKGV AQNLNNRIDN VDGNARAGIA QAIATAGLVQ AYLPGKSMMA
                                              C5

551                                                    600
      H41   IGGGTYLGEA GYAIGYSSIS AGGNWIIKGT ASGNSRGHFG ASASVGYQW.
     PMC21  IGGGTYRGEA GYAIGYSSIS DGGNWIIKGT ASGNSRGHFG ASASVGYQW.
   H41Studel IGGGTYLGEA GYAIGYSSIS AGGNWIIKGT ASGNSRGHFG ASASVGYQW.
 PMC21Bgldel IGGGTYRGEA GYAIGYSSIS DGGNWIIKGT ASGNSRGHFG ASASVGYQW.
   PMC21C1C5 IGGGTYRGEA GYAIGYSSIS DGGNWIIKGT ASGNSRGHFG ASASVGYQW.
                                              C5
```

*FIG. 10B*

```
 52   NNEEQEEYL   YLHPVQRTVA  VLIVNSDKEG  AGEKEKVEEN  SDWAVYFNEK
101   GVLTAREITL  KAGDNLKIKQ  NGTNFTYSLK  KDLTDLTSVG  TEKLSFSAHG
151   NKVNITSDTK  GLNFAKETAG  TNGDTTVHLN  GIGSTLTDTL  LNTGATTNVT
201   NDNVTDDEKK  RAASVKDVLN  AGWNIKGVKP  GTTASDNVDF  VRTYDTVEFL
251   SADTKTTTVN  VESKDNGKKT  EVKIGAKTSV  IKEKDGKLVT  GKDKGENGSS
301   TDEGEGLVTA  KEVIDAVNKA  GWRMKTTTAN  GQTGQADKFE  TVTSGTNVTF
351   ASGKGTTATV  SKDDQGNITV  MYDVNVGDAL  NVNQLQNSGW  NLDSKAVAGS
401   SGKVISGNVS  PSKGKMDETV  NINAGNNIEI  TRNGKNIDIA  TSMTPQFSSV
451   SLGAGADAPT  LSVDGDALNV  GSKKDNKPVR  ITNVAPGVKE  GDVTNVAQLK
501   GVAQNLNNRI  DNVDGNARAG  IAQAIATAGL  VQAYLPGKSM  MAIGGGTYRG
551   EAGYAIGYSS  ISDGGNWIIK  GTASGNSRGH  FGASASVGYQ  W*
```

FIG. 14A

```
 52   TDEDEEEEL   ESVQRSVVGS  IQASMEGSVE  LETISLSMTN  DSKEFVDPYI
101   VVTLKAGDNL  KIKQNTNENT  NASSFTYSLK  KDLTGLINVE  TEKLSFGANG
151   KKVNIISDTK  GLNFAKETAG  TNGDTTVHLN  GIGSTLTDML  LNTGATTNVT
201   NDNVTDDEKK  RAASVKDVLN  AGWNIKGVKP  GTTASDNVDF  VRTYDTVEFL
251   SADTKTTTVN  VESKDNGKKT  EVKIGAKTSV  IKEKDGKLVT  GKGKGENGSS
301   TDEGEGLVTA  KEVIDAVNKA  GWRMKTTTAN  GQTGQADKFE  TVTSGTKVTF
351   ASGNGTTATV  SKDDQGNITV  KYDVNVGDAL  NVNQLQNSGW  NLDSKAVAGS
401   SGKVISGNVS  PSKGKMDETV  NINAGNNIEI  TRNGKNIDIA  TSMTPQFSSV
451   SLGAGADAPT  LSVDDEGALN  VGSKDANKPV  RITNVAPGVK  EGDVTNVAQL
501   KGVAQNLNNR  IDNVNGNARA  GIAQAIATAG  LVQAYLPGKS  MMAIGGGTYL
551   GEAGYAIGYS  SISAGGNWII  KGTASGNSRG  HFGASASVGY  QW*
```

FIG. 14B

```
 52   NNETDLTSV  GTEKLSFSAN  GNKVNITSDT  KGLNFAKETA  GTNGDTTVHL
101   NGIGSTLTDT  LLNTGATTNV  TNDNVTDDEK  KRAASVKDVL  NAGWNIKGVK
151   PGTTASDNVD  FVRTYDTVEF  LSADTKTTTV  NVESKDNGKK  TEVKIGAKTS
201   VIKEKDGKLV  TGKDKGENGS  STDEGEGLVT  AKEVIDAVNK  AGWRMKTTTA
251   NGQTGQADKF  ETVTSGTNVT  FASGKGTTAT  VSKDDQGNIT  VMYDVNVGDA
301   LNVNQLQNSG  WNLDSKAVAG  SSGKVISGNV  SPSKGKMDET  VNINAGNNIE
351   ITRNGKNIDI  ATSMTPQFSS  VSLGAGADAP  TLSVDGDALN  VGSKKDNKPV
401   RITNVAPGVK  EGDVTNVAQL  KGVAQNLNNR  IDNVDGNARA  GIAQAIATAG
451   LVQAYLPGKS  MMAIGGGTYR  GEAGYAIGYS  SISDGGNWII  KGTASGNSRG
501   HFGASASVGY  QW*
```

FIG. 14C

```
 52    TDETGLINV  ETEKLSFGAN  GKKVNIISDT  KGLNFAKETA  GTNGDTTVHL
101   NGIGSTLTDM  LLNTGATTNV  TNDNVTDDEK  KRAASVKDVL  NAGWNIKGVK
151   PGTTASDNVD  FVRTYDTVEF  LSADTKTTTV  NVESKDNGKK  TEVKIGAKTS
201   VIKEKDGKLV  TGKGKGENGS  STDEGEGLVT  AKEVIDAVNK  AGWRMKTTTA
251   NGQTGQADKF  ETVTSGTKVT  FASGNGTTAT  VSKDDQGNIT  VKYDVNVGDA
301   LNVNQLQNSG  WNLDSKAVAG  SSGKVISGNV  SPSKGKMDET  VNINAGNNIE
351   ITRNGKNIDI  ATSMTPQFSS  VSLGAGADAP  TLSVDDEGAL  NVGSKDANKP
401   VRITNVAPGV  KEGDVTNVAQ  LKGVAQNLNN  RIDNVNGNAR  AGIAQAIATA
451   GLVQAYLPGK  SMMAIGGGTY  LGEAGYAIGY  SSISAGGNWI  IKGTASGNSR
501    GHFGASASVG  YQW*
```

FIG. 14D

```
 52   NNVDFVRTY  DTVEFLSADT  KTTTVNVESK  DNGKKTEVKI  GAKTSVIKEK
101   DGKLVTGKDK  GENGSSTDEG  EGLVTAKEVI  DAVNKAGWRM  KTTTANGQTG
151   QADKFETVTS  GTNVTFASGK  GTTATVSKDD  QGNITVMYDV  NVGDALNVNQ
201   LQNSGWNLDS  KAVAGSSGKV  ISGNVSPSKG  KMDETVNINA  GNNIEITRNG
251   KNIDIATSMT  PQFSSVSLGA  GADAPTLSVD  GDALNVGSKK  DNKPVRITNV
301   APGVKEGDVT  NVAQLKGVAQ  NLNNRIDNVD  GNARAGIAQA  IATAGLVQAY
351   LPGKSMMAIG  GGTYRGEAGY  AIGYSSISDG  GNWIIKGTAS  GNSRGHFGAS
401   ASVGYQW*
```

FIG. 14E

```
 52   NRAASVKDV   LNAGWNIKGV  KPGTTASDNV  DFVRTYDTVE  FLSADTKTTT
101   VNVESKDNGK  KTEVKIGAKT  SVIKEKDGKL  VTGKDKGENG  SSTDEGEGLV
151   TAKEVIDAVN  KAGWRMKTTT  ANGQTGQADK  FETVTSGTNV  TFASGKGTTA
201   TVSKDDQGNI  TVMYDVNVGD  ALNVNQLQNS  GWNLDSKAVA  GSSGKVISGN
251   VSPSKGKMDE  TVNINAGNNI  EITRNGKNID  IATSMTPQFS  SVSLGAGADA
301   PTLSVDGDAL  NVGSKKDNKP  VRITNVAPGV  KEGDVTNVAQ  LKGVAQNLNN
351   RIDNVDGNAR  AGIAQAIATA  GLVQAYLPGK  SMMAIGGGTY  RGEAGYAIGY
401   SSISDGGNWI  IKGTASGNSR  GHFGASASVG  YQW*
```

FIG. 14F

```
 50  SANTLKAGDNL  KIKQFTYSLK  KDLTDLTSVG  TEKLSFSANG  NKVNITSDTK
101  GLNFAKETAG   TNGDTTVHLN  GIGSTLTDRA  ASVKDVLNAG  WNIKGVKNVD
151  FVRTYDTVEF   LSADTKTTTV  NVESKDNGKK  TEVKIGAKTS  VIKEKDGKLV
201  TGKDKGENGS   STDEGEGLVT  AKEVIDAVNK  AGWRMKTTTA  NGQTGQADKF
251  ETVTSGTNVT   FASGKGTTAT  VSKDDQGNIT  VMYDVNVGDA  LNVNQLQNSG
301  WNLDSKAVAG   SSGKVISGNV  SPSKGKMDET  VNINAGNNIE  ITRNGKNIDI
351  ATSMTPQFSS   VSLGAGADAP  TLSVDGDALN  VGSKKDNKPV  RITNVAPGVK
401  EGDVTNVAQL   KGVAQNLNNR  IDNVDGNARA  GIAQAIATAG  LVQAYLPGKS
451  MMAIGGGTYR   GEAGYAIGYS  SISDGGNWII  KGTASGNSRG  HFGASASVGY
501  QW*
```

FIG. 14G

SEQUENCE LISTING

<160> NUMBER OF SEQ ID NOS: 52

<210> SEQ ID NO 1
<211> LENGTH: 591
<212> TYPE: PRT
<213> ORGANISM: Neisseria meningitidis

<400> SEQUENCE: 1

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser

```
                    115                 120                 125
Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
    530                 535                 540
```

```
Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 2
<211> LENGTH: 592
<212> TYPE: PRT
<213> ORGANISM: Neisseria meningitidis

<400> SEQU

```
Asp Lys Phe Glu Thr Val Thr Ser Gly Thr Lys Val Thr Phe Ala Ser
            340                 345                 350

Gly Asn Gly Thr Thr Ala Thr Val Ser Lys Asp Asp Gln Gly Asn Ile
            355                 360                 365

Thr Val Lys Tyr Asp Val Asn Val Gly Asp Ala Leu Asn Val Asn Gln
            370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
            450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
            485                 490                 495

Val Ala Gln Leu Lys Gly Val Ala Gln Asn Leu Asn Asn Arg Ile Asp
            500                 505                 510

Asn Val Asn Gly Asn Ala Arg Ala Gly Ile Ala Gln Ala Ile Ala Thr
            515                 520                 525

Ala Gly Leu Val Gln Ala Tyr Leu Pro Gly Lys Ser Met Met Ala Ile
            530                 535                 540

Gly Gly Gly Thr Tyr Leu Gly Glu Ala Gly Tyr Ala Ile Gly Tyr Ser
545                 550                 555                 560

Ser Ile Ser Ala Gly Gly Asn Trp Ile Ile Lys Gly Thr Ala Ser Gly
            565                 570                 575

Asn Ser Arg Gly His Phe Gly Ala Ser Ala Ser Val Gly Tyr Gln Trp
            580                 585                 590

<210> SEQ ID NO 3
<211> LENGTH: 589
<212> TYPE: PRT
<213> ORGANISM: Neisseria meningitidis

<400> SEQUENCE: 3

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Ser Ala Thr Val Gln
            35                  40                  45

Ala Asn Ala Thr Asp Thr Asp Glu Asp Glu Leu Glu Ser Val Ala
            50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
            85                  90                  95

His Asn Thr Leu His Gly Ala Thr Val Thr Leu Lys Ala Gly Asp Asn
            100                 105                 110

Leu Lys Ile Lys Gln Ser Gly Lys Asp Phe Thr Tyr Ser Leu Lys Lys
            115                 120                 125
```

```
Glu Leu Lys Asp Leu Thr Ser Val Glu Thr Glu Lys Leu Ser Phe Gly
    130                 135                 140
Ala Asn Gly Asn Lys Val Asn Ile Thr Ser Asp Thr Lys Gly Leu Asn
145                 150                 155                 160
Phe Ala Lys Glu Thr Ala Gly Thr Asn Gly Asp Pro Thr Val His Leu
                165                 170                 175
Asn Gly Ile Gly Ser Thr Leu Thr Asp Thr Leu Ala Gly Ser Ser Ala
                180                 185                 190
Ser His Val Asp Ala Gly Asn Gln Ser Thr His Tyr Thr Arg Ala Ala
        195                 200                 205
Ser Ile Lys Asp Val Leu Asn Ala Gly Trp Asn Ile Lys Gly Val Lys
    210                 215                 220
Thr Gly Ser Thr Thr Gly Gln Ser Glu Asn Val Asp Phe Val Arg Thr
225                 230                 235                 240
Tyr Asp Thr Val Glu Phe Leu Ser Ala Asp Thr Lys Thr Thr Thr Val
                245                 250                 255
Asn Val Glu Ser Lys Asp Asn Gly Lys Arg Thr Glu Val Lys Ile Gly
                260                 265                 270
Ala Lys Thr Ser Val Ile Lys Glu Lys Asp Gly Lys Leu Val Thr Gly
                275                 280                 285
Lys Gly Lys Gly Glu Asn Gly Ser Ser Thr Asp Glu Gly Glu Gly Leu
    290                 295                 300
Val Thr Ala Lys Glu Val Ile Asp Ala Val Asn Lys Ala Gly Trp Arg
305                 310                 315                 320
Met Lys Thr Thr Thr Ala Asn Gly Gln Thr Gly Gln Ala Asp Lys Phe
                325                 330                 335
Glu Thr Val Thr Ser Gly Thr Lys Val Thr Phe Ala Ser Gly Asn Gly
                340                 345                 350
Thr Thr Ala Thr Val Ser Lys Asp Asp Gln Gly Asn Ile Thr Val Lys
        355                 360                 365
Tyr Asp Val Asn Val Gly Asp Ala Leu Asn Val Asn Gln Leu Gln Asn
    370                 375                 380
Ser Gly Trp Asn Leu Asp Ser Lys Ala Val Ala Gly Ser Ser Gly Lys
385                 390                 395                 400
Val Ile Ser Gly Asn Val Ser Pro Ser Lys Gly Lys Met Asp Glu Thr
                405                 410                 415
Val Asn Ile Asn Ala Gly Asn Asn Ile Glu Ile Thr Arg Asn Gly Lys
                420                 425                 430
Asn Ile Asp Ile Ala Thr Ser Met Thr Pro Gln Phe Ser Ser Val Ser
        435                 440                 445
Leu Gly Ala Gly Ala Asp Ala Pro Thr Leu Ser Val Asp Asp Glu Gly
    450                 455                 460
Ala Leu Asn Val Gly Ser Lys Asp Ala Asn Lys Pro Val Arg Ile Thr
465                 470                 475                 480
Asn Val Ala Pro Gly Val Lys Glu Gly Asp Val Thr Asn Val Ala Gln
                485                 490                 495
Leu Lys Gly Val Ala Gln Asn Leu Asn Asn Arg Ile Asp Asn Val Asn
                500                 505                 510
Gly Asn Ala Arg Ala Gly Ile Ala Gln Ala Ile Ala Thr Ala Gly Leu
        515                 520                 525
Ala Gln Ala Tyr Leu Pro Gly Lys Ser Met Met Ala Ile Gly Gly Gly
    530                 535                 540
Thr Tyr Leu Gly Glu Ala Gly Tyr Ala Ile Gly Tyr Ser Ser Ile Ser
545                 550                 555                 560
```

Asp Thr Gly Asn Trp Val Ile Lys Gly Thr Ala Ser Gly Asn Ser Arg
            565                 570                 575

Gly His Phe Gly Thr Ser Ala Ser Val Gly Tyr Gln Trp
            580                 585

<210> SEQ ID NO 4
<211> LENGTH: 594
<212> TYPE: PRT
<213> ORGANISM: Neisseria meningitidis

<400> SEQUENCE: 4

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Phe Ala Thr Val Gln
            35                  40                  45

Ala Ser Thr Thr Asp Asp Asp Leu Tyr Leu Glu Pro Val Gln Arg
    50                  55                  60

Thr Ala Val Val Leu Ser Phe Arg Ser Asp Lys Glu Gly Thr Gly Glu
65                  70                  75                  80

Lys Glu Val Thr Glu Asp Ser Asn Trp Gly Val Tyr Phe Asp Lys Lys
            85                  90                  95

Gly Val Leu Thr Ala Gly Thr Ile Thr Leu Lys Ala Gly Asp Asn Leu
            100                 105                 110

Lys Ile Lys Gln Asn Thr Asn Glu Asn Thr Asn Ala Ser Ser Phe Thr
        115                 120                 125

Tyr Ser Leu Lys Lys Asp Leu Thr Asp Leu Thr Ser Val Gly Thr Glu
    130                 135                 140

Lys Leu Ser Phe Ser Ala Asn Ser Asn Lys Val Asn Ile Thr Ser Asp
145                 150                 155                 160

Thr Lys Gly Leu Asn Phe Ala Lys Lys Thr Ala Glu Thr Asn Gly Asp
            165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
            245                 250                 255

Lys Thr Thr Thr Val Asn Val Glu Ser Lys Asp Asn Gly Lys Arg Thr
            260                 265                 270

Glu Val Lys Ile Gly Ala Lys Thr Ser Val Ile Lys Glu Lys Asp Gly
        275                 280                 285

Lys Leu Val Thr Gly Lys Asp Leu Gly Glu Asn Asp Ser Ser Thr Asp
    290                 295                 300

Lys Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
            325                 330                 335

Gln Ala Asp Lys Phe Glu Thr Val Thr Ser Gly Thr Asn Val Thr Phe
            340                 345                 350

```
Ala Ser Gly Lys Gly Thr Thr Ala Thr Val Ser Lys Asp Asp Gln Gly
        355                 360                 365

Asn Ile Thr Val Met Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 5
<211> LENGTH: 591
<212> TYPE: PRT
<213> ORGANISM: Neisseria meningitidis

<400> SEQUENCE: 5

Met Asn Glu Ile Leu Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
        50                  55                  60

Val Leu Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125
```

```
Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
450                 455                 460

Gly Asp Ala Leu Asn Val Gly Ser Lys Lys Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
530                 535                 540

Gly Gly Thr Tyr Arg Gly Glu Ala Gly Tyr Ala Ile Gly Tyr Ser Ser
545                 550                 555                 560
```

Ile Ser Asp Gly Gly Asn Trp Ile Ile Lys Gly Thr Ala Ser Gly Asn
            565                 570                 575

Ser Arg Gly His Phe Gly Ala Ser Ala Ser Val Gly Tyr Gln Trp
            580                 585                 590

<210> SEQ ID NO 6
<211> LENGTH: 599
<212> TYPE: PRT
<213> ORGANISM: Neisseria meningitidis

<400> SEQUENCE: 6

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Pro Val Val
    50                  55                  60

Arg Ser Ala Leu Val Leu Gln Phe Met Ile Asp Lys Glu Gly Asn Gly
65                  70                  75                  80

Glu Asn Glu Ser Thr Gly Asn Ile Gly Trp Ser Ile Tyr Tyr Asp Asn
                85                  90                  95

His Asn Thr Leu His Gly Ala Thr Val Thr Leu Lys Ala Gly Asp Asn
            100                 105                 110

Leu Lys Ile Lys Gln Asn Thr Asn Lys Asn Thr Asn Glu Asn Thr Asn
        115                 120                 125

Asp Ser Ser Phe Thr Tyr Ser Leu Lys Lys Asp Leu Thr Asp Leu Thr
    130                 135                 140

Ser Val Glu Thr Glu Lys Leu Ser Phe Gly Ala Asn Gly Asn Lys Val
145                 150                 155                 160

Asn Ile Thr Ser Asp Thr Lys Gly Leu Asn Phe Ala Lys Glu Thr Ala
                165                 170                 175

Gly Thr Asn Gly Asp Thr Thr Val His Leu Asn Gly Ile Gly Ser Thr
            180                 185                 190

Leu Thr Asp Thr Leu Leu Asn Thr Gly Ala Thr Thr Asn Val Thr Asn
        195                 200                 205

Asp Asn Val Thr Asp Asp Lys Lys Lys Arg Ala Ala Ser Val Lys Asp
    210                 215                 220

Val Leu Asn Ala Gly Trp Asn Ile Lys Gly Val Lys Pro Gly Thr Thr
225                 230                 235                 240

Ala Ser Asp Asn Val Asp Phe Val His Thr Tyr Asp Thr Val Glu Phe
                245                 250                 255

Leu Ser Ala Asp Thr Lys Thr Thr Val Asn Val Glu Ser Lys Asp
            260                 265                 270

Asn Gly Lys Arg Thr Glu Val Lys Ile Gly Ala Lys Thr Ser Val Ile
        275                 280                 285

Lys Glu Lys Asp Gly Lys Leu Val Thr Gly Lys Gly Lys Gly Glu Asn
    290                 295                 300

Gly Ser Ser Thr Asp Glu Gly Gly Leu Val Thr Ala Lys Glu Val
305                 310                 315                 320

Ile Asp Ala Val Asn Lys Ala Gly Trp Arg Met Lys Thr Thr Thr Ala
                325                 330                 335

Asn Gly Gln Thr Gly Gln Ala Asp Lys Phe Glu Thr Val Thr Ser Gly
            340                 345                 350

```
Thr Asn Val Thr Phe Ala Ser Gly Lys Gly Thr Thr Ala Thr Val Ser
            355                 360                 365

Lys Asp Asp Gln Gly Asn Ile Thr Val Lys Tyr Asp Val Asn Val Gly
            370                 375                 380

Asp Ala Leu Asn Val Asn Gln Leu Gln Asn Ser Gly Trp Asn Leu Asp
385                 390                 395                 400

Ser Lys Ala Val Ala Gly Ser Ser Gly Lys Val Ile Ser Gly Asn Val
            405                 410                 415

Ser Pro Ser Lys Gly Lys Met Asp Glu Thr Val Asn Ile Asn Ala Gly
            420                 425                 430

Asn Asn Ile Glu Ile Thr Arg Asn Gly Lys Asn Ile Asp Ile Ala Thr
            435                 440                 445

Ser Met Thr Pro Gln Phe Ser Ser Val Ser Leu Gly Ala Gly Ala Asp
            450                 455                 460

Ala Pro Thr Leu Ser Val Asp Asp Lys Gly Ala Leu Asn Val Gly Ser
465                 470                 475                 480

Lys Asp Ala Asn Lys Pro Val Arg Ile Thr Asn Val Ala Pro Gly Val
            485                 490                 495

Lys Glu Gly Asp Val Thr Asn Val Ala Gln Leu Lys Gly Val Ala Gln
            500                 505                 510

Asn Leu Asn Asn Arg Ile Asp Asn Val Asp Gly Asn Ala Arg Ala Gly
            515                 520                 525

Ile Ala Gln Ala Ile Ala Thr Ala Gly Leu Val Gln Ala Tyr Leu Pro
            530                 535                 540

Gly Lys Ser Met Met Ala Ile Gly Gly Gly Thr Tyr Arg Gly Glu Ala
545                 550                 555                 560

Gly Tyr Ala Ile Gly Tyr Ser Ser Ile Ser Asp Gly Gly Asn Trp Ile
            565                 570                 575

Ile Lys Gly Thr Ala Ser Gly Asn Ser Arg Gly His Phe Gly Ala Ser
            580                 585                 590

Ala Ser Val Gly Tyr Gln Trp
            595

<210> SEQ ID NO 7
<211> LENGTH: 598
<212> TYPE: PRT
<213> ORGANISM: Neisseria meningitidis

<400> SEQUENCE: 7

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
            35                  40                  45

Ala Asn Ala Thr Asp Asp Asp Leu Tyr Leu Glu Pro Val Gln Arg
            50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
            85                  90                  95

Arg Val Leu Lys Ala Gly Ala Ile Thr Leu Lys Ala Gly Asp Asn Leu
            100                 105                 110

Lys Ile Lys Gln Asn Thr Asn Glu Asn Thr Asn Glu Asn Thr Asn Asp
            115                 120                 125
```

```
Ser Ser Phe Thr Tyr Ser Leu Lys Lys Asp Leu Thr Asp Leu Thr Ser
    130                 135                 140

Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
                165                 170                 175

Thr Asn Gly Asp Pro Thr Val His Leu Asn Gly Ile Gly Ser Thr Leu
            180                 185                 190

Thr Asp Thr Leu Leu Asn Thr Gly Ala Thr Thr Asn Val Thr Asn Asp
        195                 200                 205

Asn Val Thr Asp Asp Glu Lys Lys Arg Ala Ala Ser Val Lys Asp Val
210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
                245                 250                 255

Ser Ala Asp Thr Lys Thr Thr Thr Val Asn Val Glu Ser Lys Asp Asn
            260                 265                 270

Gly Lys Lys Thr Glu Val Lys Ile Gly Ala Lys Thr Ser Val Ile Lys
        275                 280                 285

Glu Lys Asp Gly Lys Leu Val Thr Gly Lys Lys Asp Glu Asn Gly
290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Thr Ala Asn
                325                 330                 335

Gly Gln Thr Gly Gln Ala Asp Lys Phe Glu Thr Val Thr Ser Gly Thr
            340                 345                 350

Lys Val Thr Phe Ala Ser Gly Asn Gly Thr Thr Ala Thr Val Ser Lys
        355                 360                 365

Asp Asp Gln Gly Asn Ile Thr Val Lys Tyr Asp Val Asn Val Gly Asp
370                 375                 380

Ala Leu Asn Val Asn Gln Leu Gln Asn Ser Gly Trp Asn Leu Asp Ser
385                 390                 395                 400

Lys Ala Val Ala Gly Ser Ser Gly Lys Val Ile Ser Gly Asn Val Ser
                405                 410                 415

Pro Ser Lys Gly Lys Met Asp Glu Thr Val Asn Ile Asn Ala Gly Asn
            420                 425                 430

Asn Ile Glu Ile Thr Arg Asn Gly Lys Asn Ile Asp Ile Ala Thr Ser
        435                 440                 445

Met Thr Pro Gln Phe Ser Ser Val Ser Leu Gly Ala Gly Ala Asp Ala
450                 455                 460

Pro Thr Leu Ser Val Asp Asp Glu Gly Ala Leu Asn Val Gly Ser Lys
465                 470                 475                 480

Asp Ala Asn Lys Pro Val Arg Ile Thr Asn Val Ala Pro Gly Val Lys
                485                 490                 495

Glu Gly Asp Val Thr Asn Val Ala Gln Leu Lys Gly Val Ala Gln Asn
            500                 505                 510

Leu Asn Asn Arg Ile Asp Asn Val Asp Gly Asn Ala Arg Ala Gly Ile
        515                 520                 525

Ala Gln Ala Ile Ala Thr Ala Gly Leu Ala Gln Ala Tyr Leu Pro Gly
530                 535                 540

Lys Ser Met Met Ala Ile Gly Gly Gly Thr Tyr Arg Gly Glu Ala Gly
```

-continued

```
                545                 550                 555                 560
Tyr Ala Ile Gly Tyr Ser Ser Ile Ser Asp Thr Gly Asn Trp Val Ile
                565                 570                 575
Lys Gly Thr Ala Ser Gly Asn Ser Arg Gly His Phe Gly Ala Ser Ala
                580                 585                 590
Ser Val Gly Tyr Gln Trp
                595

<210> SEQ ID NO 8
<211> LENGTH: 598
<212> TYPE: PRT
<213> ORGANISM: Neisseria meningitidis

<400> SEQUENCE: 8

Met Asn Lys Ile Ser Arg Ile Ile Trp Asn Ser Ala Leu Asn Ala Trp
1               5                   10                  15
Val Val Val Ser Glu Leu Thr Arg Asn His Thr Lys Arg Ala Ser Ala
                20                  25                  30
Thr Val Ala Thr Ala Val Leu Ala Thr Leu Leu Phe Ala Thr Val Gln
                35                  40                  45
Ala Asn Ala Thr Asp Asp Asp Leu Tyr Leu Glu Pro Val Gln Arg
        50                  55                  60
Thr Ala Val Val Leu Ser Phe Arg Ser Asp Lys Glu Gly Thr Gly Glu
65                  70                  75                  80
Lys Glu Gly Thr Glu Asp Ser Asn Trp Ala Val Tyr Phe Asp Glu Lys
                85                  90                  95
Arg Val Leu Lys Ala Gly Ala Ile Thr Leu Lys Ala Gly Asp Asn Leu
                100                 105                 110
Lys Ile Lys Gln Asn Thr Asn Glu Asn Thr Asn Glu Asn Thr Asn Asp
                115                 120                 125
Ser Ser Phe Thr Tyr Ser Leu Lys Lys Asp Leu Thr Asp Leu Thr Ser
        130                 135                 140
Val Glu Thr Glu Lys Leu Ser Phe Gly Ala Asn Gly Asn Lys Val Asn
145                 150                 155                 160
Ile Thr Ser Asp Thr Lys Gly Leu Asn Phe Ala Lys Glu Thr Ala Gly
                165                 170                 175
Thr Asn Gly Asp Pro Thr Val His Leu Asn Gly Ile Gly Ser Thr Leu
                180                 185                 190
Thr Asp Thr Leu Leu Asn Thr Gly Ala Thr Thr Asn Val Thr Asn Asp
                195                 200                 205
Asn Val Thr Asp Asp Glu Lys Lys Arg Ala Ala Ser Val Lys Asp Val
        210                 215                 220
Leu Asn Ala Gly Trp Asn Ile Lys Gly Val Lys Pro Gly Thr Thr Ala
225                 230                 235                 240
Ser Asp Asn Val Asp Phe Val Arg Thr Tyr Asp Thr Val Glu Phe Leu
                245                 250                 255
Ser Ala Asp Thr Lys Thr Thr Thr Val Asn Val Glu Ser Lys Asp Asn
                260                 265                 270
Gly Lys Arg Thr Glu Val Lys Ile Gly Ala Lys Thr Ser Val Ile Lys
                275                 280                 285
Glu Lys Asp Gly Lys Leu Val Thr Gly Lys Gly Lys Gly Glu Asn Gly
        290                 295                 300
Ser Ser Thr Asp Glu Gly Glu Gly Leu Val Thr Ala Lys Glu Val Ile
305                 310                 315                 320
Asp Ala Val Asn Lys Ala Gly Trp Arg Met Lys Thr Thr Thr Ala Asn
```

```
                     325                 330                 335
Gly Gln Thr Gly Gln Ala Asp Lys Phe Glu Thr Val Thr Ser Gly Thr
            340                 345                 350
Lys Val Thr Phe Ala Ser Gly Asn Gly Thr Thr Ala Thr Val Ser Lys
                355                 360                 365
Asp Asp Gln Gly Asn Ile Thr Val Lys Tyr Asp Val Asn Val Gly Asp
        370                 375                 380
Ala Leu Asn Val Asn Gln Leu Gln Asn Ser Gly Trp Asn Leu Asp Ser
385                 390                 395                 400
Lys Ala Val Ala Gly Ser Ser Gly Lys Val Ile Ser Gly Asn Val Ser
                405                 410                 415
Pro Ser Lys Gly Lys Met Asp Glu Thr Val Asn Ile Asn Ala Gly Asn
            420                 425                 430
Asn Ile Glu Ile Thr Arg Asn Gly Lys Asn Ile Asp Ile Ala Thr Ser
                435                 440                 445
Met Thr Pro Gln Phe Ser Ser Val Ser Leu Gly Ala Gly Ala Asp Ala
            450                 455                 460
Pro Thr Leu Ser Val Asp Asp Glu Gly Ala Leu Asn Val Gly Ser Lys
465                 470                 475                 480
Asp Ala Asn Lys Pro Val Arg Ile Thr Asn Val Ala Pro Gly Val Lys
                485                 490                 495
Glu Gly Asp Val Thr Asn Val Ala Gln Leu Lys Gly Val Ala Gln Asn
                500                 505                 510
Leu Asn Asn Arg Ile Asp Asn Val Asp Gly Asn Ala Arg Ala Gly Ile
            515                 520                 525
Ala Gln Ala Ile Ala Thr Ala Gly Leu Ala Gln Ala Tyr Leu Pro Gly
        530                 535                 540
Lys Ser Met Met Ala Ile Gly Gly Gly Thr Tyr Arg Gly Glu Ala Gly
545                 550                 555                 560
Tyr Ala Ile Gly Tyr Ser Ser Ile Ser Asp Thr Gly Asn Trp Val Ile
                565                 570                 575
Lys Gly Thr Ala Ser Gly Asn Ser Arg Gly His Phe Gly Thr Ser Ala
            580                 585                 590
Ser Val Gly Tyr Gln Trp
            595

<210> SEQ ID NO 9
<211> LENGTH: 594
<212> TYPE: PRT
<213> ORGANISM: Neisseria meningitidis

<400> SEQUENCE: 9

Met Asn Lys Ile Tyr Arg Ile Ile Trp Asn Ser Ala Leu Asn Ala Trp
1               5                   10                  15
Val Val Ser Glu Leu Thr Arg Asn His Thr Lys Arg Ala Ser Ala
            20                  25                  30
Thr Val Ala Thr Ala Val Leu Ala Thr Leu Leu Phe Ala Thr Val Gln
        35                  40                  45
Ala Asn Ala Thr Asp Asp Asp Leu Tyr Leu Glu Pro Val Gln Arg
    50                  55                  60
Thr Ala Val Val Leu Ser Phe Arg Ser Asp Lys Glu Gly Thr Gly Glu
65                  70                  75                  80
Lys Glu Gly Thr Glu Asp Ser Asn Trp Ala Val Tyr Phe Asp Glu Lys
                85                  90                  95
Arg Val Leu Lys Ala Gly Ala Ile Thr Leu Lys Ala Gly Asp Asn Leu
```

```
                 100                 105                 110
Lys Ile Lys Gln Asn Thr Asn Glu Asn Thr Asn Asp Ser Ser Phe Thr
             115                 120                 125
Tyr Ser Leu Lys Lys Asp Leu Thr Asp Leu Thr Ser Val Glu Thr Glu
         130                 135                 140
Lys Leu Ser Phe Gly Ala Asn Gly Asn Lys Val Asn Ile Thr Ser Asp
145                 150                 155                 160
Thr Lys Gly Leu Asn Phe Ala Lys Glu Thr Ala Gly Thr Asn Gly Asp
                 165                 170                 175
Pro Thr Val His Leu Asn Gly Ile Gly Ser Thr Leu Thr Asp Thr Leu
             180                 185                 190
Leu Asn Thr Gly Ala Thr Thr Asn Val Thr Asn Asp Asn Val Thr Asp
         195                 200                 205
Asp Glu Lys Lys Arg Ala Ala Ser Val Lys Asp Val Leu Asn Ala Gly
    210                 215                 220
Trp Asn Ile Lys Gly Val Lys Pro Gly Thr Thr Ala Ser Asp Asn Val
225                 230                 235                 240
Asp Phe Val Arg Thr Tyr Asp Thr Val Glu Phe Leu Ser Ala Asp Thr
                 245                 250                 255
Lys Thr Thr Thr Val Asn Val Glu Ser Lys Asp Asn Gly Lys Lys Thr
             260                 265                 270
Glu Val Lys Ile Gly Ala Lys Thr Ser Val Ile Lys Glu Lys Asp Gly
         275                 280                 285
Lys Leu Val Thr Gly Lys Gly Lys Asp Glu Asn Gly Ser Ser Thr Asp
    290                 295                 300
Glu Gly Glu Gly Leu Val Thr Ala Lys Glu Val Ile Asp Ala Val Asn
305                 310                 315                 320
Lys Ala Gly Trp Arg Met Lys Thr Thr Thr Ala Asn Gly Gln Thr Gly
                 325                 330                 335
Gln Ala Asp Lys Phe Glu Thr Val Thr Ser Gly Thr Asn Val Thr Phe
             340                 345                 350
Ala Ser Gly Lys Gly Thr Thr Ala Thr Val Ser Lys Asp Asp Gln Gly
         355                 360                 365
Asn Ile Thr Val Lys Tyr Asp Val Asn Val Gly Asp Ala Leu Asn Val
    370                 375                 380
Asn Gln Leu Gln Asn Ser Gly Trp Asn Leu Asp Ser Lys Ala Val Ala
385                 390                 395                 400
Gly Ser Ser Gly Lys Val Ile Ser Gly Asn Val Ser Pro Ser Lys Gly
             405                 410                 415
Lys Met Asp Glu Thr Val Asn Ile Asn Ala Gly Asn Asn Ile Glu Ile
         420                 425                 430
Thr Arg Asn Gly Lys Asn Ile Asp Ile Ala Thr Ser Met Ala Pro Gln
    435                 440                 445
Phe Ser Ser Val Ser Leu Gly Ala Gly Ala Asp Ala Pro Thr Leu Ser
    450                 455                 460
Val Asp Asp Glu Gly Ala Leu Asn Val Gly Ser Lys Asp Thr Asn Lys
465                 470                 475                 480
Pro Val Arg Ile Thr Asn Val Ala Pro Gly Val Lys Glu Gly Asp Val
             485                 490                 495
Thr Asn Val Ala Gln Leu Lys Gly Val Ala Gln Asn Leu Asn Asn Arg
         500                 505                 510
Ile Asp Asn Val Asp Gly Asn Ala Arg Ala Gly Ile Ala Gln Ala Ile
    515                 520                 525
```

```
Ala Thr Ala Gly Leu Val Gln Ala Tyr Leu Pro Gly Lys Ser Met Met
        530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 10
<211> LENGTH: 592
<212> TYPE: PRT
<213> ORGANISM: Neisseria meningitidis

<400> SEQUENCE: 10

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Ser Val Gln
50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Lys Asp Gly Lys Leu
        275                 280                 285

Val Thr Gly Lys Gly Lys Gly Glu Asn Gly Ser Ser Thr Asp Glu Gly
290                 295                 300

Glu Gly Leu Val Thr Ala Lys Glu Val Ile Asp Ala Val Asn Lys Ala
```

-continued

```
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Ser Arg
            420                 425                 430

Asn Gly Lys Asn Ile Asp Ile Ala Thr Ser Met Ala Pro Gln Phe Ser
        435                 440                 445

Ser Val Ser Leu Gly Ala Gly Ala Asp Ala Pro Thr Leu Ser Val Asp
    450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
            500                 505                 510

Asn Val Asp Gly Asn Ala Arg Ala Gly Ile Ala Gln Ala Ile Ala Thr
        515                 520                 525

Ala Gly Leu Val Gln Ala Tyr Leu Pro Gly Lys Ser Met Met Ala Ile
    530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
            580                 585                 590

<210> SEQ ID NO 11
<211> LENGTH: 604
<212> TYPE: PRT
<213> ORGANISM: Neisseria meningitidis
<220> FEATURE:
<221> NAME/KEY: misc_feature
<223> OTHER INFORMATION: "X" is any or absent amino acid at a
      corresponding position in any one of SEQ ID NOS 1-10 or a
      conservative substitution thereo

<400> SEQUENCE: 11

Met Asn Xaa Ile Xaa Arg Ile Ile Trp Asn Ser Ala Leu Asn Ala Trp
1               5                   10                  15

Val Xaa Val Ser Glu Leu Thr Arg Asn His Thr Lys Arg Ala Ser Ala
            20                  25                  30

Thr Val Xaa Thr Ala Val Leu Ala Thr Leu Leu Xaa Ala Thr Val Gln
        35                  40                  45

Ala Xaa Xaa Xaa Xaa Xaa Xaa Xaa Xaa Xaa Xaa Xaa Xaa Leu Xaa Xaa
    50                  55                  60

Val Xaa Arg Xaa Xaa Xaa Val Xaa Xaa Xaa Xaa Xaa Xaa Xaa Glu Gly
65                  70                  75                  80
```

```
Xaa Xaa Glu Xaa Glu Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Thr Leu Lys Ala
            100                 105                 110

Gly Asp Asn Leu Lys Ile Lys Gln Xaa Xaa Xaa Xaa Xaa Xaa
            115                 120                 125

Xaa Xaa Xaa Xaa Xaa Xaa Phe Thr Tyr Ser Leu Lys Lys Xaa Leu Xaa
130                 135                 140

Xaa Leu Xaa Xaa Val Xaa Thr Glu Lys Leu Ser Phe Xaa Ala Asn Xaa
145                 150                 155                 160

Xaa Lys Val Asn Ile Xaa Ser Asp Thr Lys Gly Leu Asn Phe Ala Lys
                165                 170                 175

Xaa Thr Ala Xaa Thr Asn Gly Asp Xaa Thr Val His Leu Asn Gly Ile
                180                 185                 190

Gly Ser Thr Leu Thr Asp Xaa Leu Xaa Xaa Xaa Ala Xaa Xaa Xaa
            195                 200                 205

Xaa Xaa Xaa Xaa Xaa Xaa Thr Xaa Xaa Xaa Xaa Arg Ala Ala Ser
210                 215                 220

Xaa Lys Asp Val Leu Asn Ala Gly Trp Asn Ile Lys Gly Val Lys Xaa
225                 230                 235                 240

Gly Xaa Thr Xaa Xaa Xaa Xaa Asn Val Asp Phe Val Xaa Thr Tyr
            245                 250                 255

Asp Thr Val Glu Phe Leu Ser Ala Asp Thr Lys Thr Thr Val Asn
            260                 265                 270

Val Glu Ser Lys Asp Asn Gly Lys Xaa Thr Glu Val Lys Ile Gly Ala
            275                 280                 285

Lys Thr Ser Val Ile Lys Glu Lys Asp Gly Lys Leu Val Thr Gly Lys
            290                 295                 300

Xaa Lys Xaa Glu Asn Xaa Ser Ser Thr Asp Xaa Gly Glu Gly Leu Val
305                 310                 315                 320

Thr Ala Lys Glu Val Ile Asp Ala Val Asn Lys Ala Gly Trp Arg Met
                325                 330                 335

Lys Thr Thr Thr Ala Asn Gly Gln Thr Gly Gln Ala Asp Lys Phe Glu
                340                 345                 350

Thr Val Thr Ser Gly Thr Xaa Val Thr Phe Ala Ser Gly Xaa Gly Thr
                355                 360                 365

Thr Ala Thr Val Ser Lys Asp Asp Gln Gly Asn Ile Thr Val Xaa Tyr
370                 375                 380

Asp Val Asn Val Gly Asp Ala Leu Asn Val Asn Gln Leu Gln Asn Ser
385                 390                 395                 400

Gly Trp Asn Leu Asp Ser Lys Ala Val Ala Gly Ser Ser Gly Lys Val
                405                 410                 415

Ile Ser Gly Asn Val Ser Pro Ser Lys Gly Lys Met Asp Glu Thr Val
                420                 425                 430

Asn Ile Asn Ala Gly Asn Asn Ile Glu Ile Xaa Arg Asn Gly Lys Asn
                435                 440                 445

Ile Asp Ile Ala Thr Ser Met Xaa Pro Gln Phe Ser Ser Val Ser Leu
450                 455                 460

Gly Ala Gly Ala Asp Ala Pro Thr Leu Ser Val Asp Xaa Xaa Xaa Ala
465                 470                 475                 480

Leu Asn Val Gly Ser Lys Xaa Xaa Asn Lys Pro Val Arg Ile Thr Asn
                485                 490                 495

Val Ala Pro Gly Val Lys Glu Gly Asp Val Thr Asn Val Ala Gln Leu
```

```
                  500             505              510
Lys Gly Val Ala Gln Asn Leu Asn Asn Xaa Ile Asp Asn Val Xaa Gly
            515                 520                 525

Asn Ala Arg Ala Gly Ile Ala Gln Ala Ile Ala Thr Ala Gly Leu Xaa
            530                 535                 540

Gln Ala Tyr Leu Pro Gly Lys Ser Met Met Ala Ile Gly Xaa Thr
545                 550                 555                 560

Tyr Xaa Gly Glu Ala Gly Tyr Ala Ile Gly Tyr Ser Ser Ile Ser Xaa
            565                 570                 575

Xaa Gly Asn Trp Xaa Ile Lys Gly Thr Ala Ser Gly Asn Ser Arg Gly
            580                 585                 590

His Phe Gly Xaa Ser Ala Ser Val Gly Tyr Gln Trp
            595                 600
```

<210> SEQ ID NO 12
<211> LENGTH: 1776
<212> TYPE: DNA
<213> ORGANISM: Neisseria meningitidis

<400> SEQUENCE: 12

```
atgaacaaaa tataccgcat catttggaat agtgccctca atgcatgggt cgtcgtatcc      60
gagctcacac gcaaccacac caaacgcgcc tccgcaaccg tgaagaccgc cgtattggcg     120
actctgttgt ttgcaacggt tcaggcaagt gctaacaatg aagagcaaga agaagattta     180
tatttagacc ccgtacaacg cactgttgcc gtgttgatag tcaattccga taaagaaggc     240
acgggagaaa agaaaaagt agaagaaaat tcagattggg cagtatattt caacgagaaa     300
ggagtactaa cagccagaga aatcaccctc aaagccggcg acaacctgaa atcaaacaa     360
aacggcacaa acttcaccta ctcgctgaaa aaagacctca cagatctgac cagtgttgga     420
actgaaaaat tatcgtttag cgcaaacggc aataaagtca acatcacaag cgacaccaaa     480
ggcttgaatt ttgcgaaaga aacggctggg acgaacggcg acaccacggt tcatctgaac     540
ggtattggtt cgactttgac cgatacgctg ctgaataccg agcgaccac aaacgtaacc     600
aacgacaacg ttaccgatga cgagaaaaaa cgtgcggcaa gcgttaaaga cgtattaaac     660
gctggctgga acattaaagg cgttaaaccc ggtacaacag cttccgataa cgttgatttc     720
gtccgcactt acgacacagt cgagttcttg agcgcagata cgaaaacaac gactgttaat     780
gtggaaagca agacaacgg caagaaaacc gaagttaaaa tcggtgcgaa gacttctgtt     840
attaagaaa aagacggtaa gttggttact ggtaaagaca aggcgagaa tggttcttct     900
acagacgaag gcgaaggctt agtgactgca aagaagtga ttgatgcagt aaacaaggct     960
ggttggagaa tgaaaacaac aaccgctaat ggtcaaacag gtcaagctga caagtttgaa    1020
accgttacat caggcacaaa tgtaaccttt gctagtggta aggtacaac tgcgactgta    1080
agtaaagatg atcaaggcaa catcactgtt atgtatgatg taaatgtcgg cgatgcccta    1140
aacgtcaatc agctgcaaaa cagcggttgg aatttggatt ccaaagcggt tgcaggttct    1200
tcgggcaaag tcatcagcgg caatgtttcg ccgagcaagg gaaagatgga tgaaaccgtc    1260
aacattaatg ccggcaacaa catcgagatt acccgcaacg gtaaaaatat cgacatcgcc    1320
acttcgatga ccccgcagtt ttccagcgtt tcgctcggcg cggggggcgga tgcgcccact    1380
ttgagcgtgg atggggacgc attgaatgtc ggcagcaaga aggacaacaa accgtccgc    1440
attaccaatg tcgccccggg cgttaaagag ggggatgtta caaacgtcgc acaacttaaa    1500
ggcgtggcgc aaaacttgaa caaccgcatc gacaatgtgg acggcaacgc gcgtgcgggc    1560
```

| atcgcccaag cgattgcaac cgcaggtctg gttcaggcgt atttgcccgg caagagtatg | 1620 |
| atggcgatcg gcggcggcac ttatcgcggc gaagccggtt acgccatcgg ctactccagt | 1680 |
| atttccgacg gcggaaattg gattatcaaa ggcacggctt ccggcaattc gcgcggccat | 1740 |
| ttcggtgctt ccgcatctgt cggttatcag tggtaa | 1776 |

<210> SEQ ID NO 13
<211> LENGTH: 1779
<212> TYPE: DNA
<213> ORGANISM: Neisseria meningitidis

<400> SEQUENCE: 13

| atgaacaaaa tataccgcat catttggaat agtgccctca atgcctgggt cgccgtatcc | 60 |
| gagctcacac gcaaccacac caaacgcgcc tccgcaaccg tgaagaccgc cgtattggcg | 120 |
| acactgttgt ttgcaacggt tcaggcgaat gctaccgatg aagatgaaga agaagagtta | 180 |
| gaatccgtac aacgctctgt cgtagggagc attcaagcca gtatggaagg cagcgtcgaa | 240 |
| ttggaaacga tatcattatc aatgactaac gacagcaagg aatttgtaga cccatacata | 300 |
| gtagttaccc tcaaagccgg cgacaacctg aaaatcaaac aaaacaccaa tgaaaacacc | 360 |
| aatgccagta gcttcaccta ctcgctgaaa aaagacctca caggcctgat caatgttgaa | 420 |
| actgaaaaat tatcgtttgg cgcaaacggc aagaaagtca acatcataag cgacaccaaa | 480 |
| ggcttgaatt tcgcgaaaga aacggctggg acgaacggcg acaccacggt tcatctgaac | 540 |
| ggtatcggtt cgactttgac cgatatgctg ctgaataccg gagcgaccac aaacgtaacc | 600 |
| aacgacaacg ttaccgatga cgagaaaaaa cgtgcggcaa gcgttaaaga cgtattaaac | 660 |
| gcaggctgga acattaaagg cgttaaaccc ggtacaacag cttccgataa cgttgatttc | 720 |
| gtccgcactt acgacacagt cgagttcttg agcgcagata cgaaaacaac gactgttaat | 780 |
| gtggaaagca agacaacgg caagaaaacc gaagttaaaa tcggtgcgaa gacttctgtt | 840 |
| attaagaaa aagacggtaa gttggttact ggtaaaggca aggcgagaa tggttcttct | 900 |
| acagacgaag cgaaggctt agtgactgca aaagaagtga ttgatgcagt aaacaaggct | 960 |
| ggttggagaa tgaaaacaac aaccgctaat ggtcaaacag gtcaagctga caagtttgaa | 1020 |
| accgttacat caggcacaaa agtaaccttt gctagtggta atggtacaac tgcgactgta | 1080 |
| agtaaagatg atcaaggcaa catcactgtt aagtatgatg taaatgtcgg cgatgcccta | 1140 |
| aacgtcaatc agctgcaaaa cagcggttgg aatttggatt ccaaagcggt tgcaggttct | 1200 |
| tcgggcaaag tcatcagcgg caatgtttcg ccgagcaagg gaaagatgga tgaaaccgtc | 1260 |
| aacattaatg ccggcaacaa catcgagatt acccgcaacg gcaaaaatat cgacatcgcc | 1320 |
| acttcgatga ccccgcaatt ttccagcgtt tcgctcggcg cggggggcgga tgcgcccact | 1380 |
| ttaagcgtgg atgacgaggg cgcgttgaat gtcggcagca aggatgccaa caaacccgtc | 1440 |
| cgcattacca atgtcgcccc gggcgttaaa gaggggggatt ttacaaacgt cgcgcaactt | 1500 |
| aaaggtgtgg cgcaaaactt gaacaaccgc atcgacaatg tgaacggcaa cgcgcgtgcg | 1560 |
| ggcatcgccc aagcgattgc aaccgcaggt ctggttcagg cgtatctgcc cggcaagagt | 1620 |
| atgatggcga tcggcggcgg cacttatctc ggcgaagccg ttatgccat cggctactca | 1680 |
| agcatttccg ccgcggaaa ttggattatc aaaggcacgg cttccggcaa ttcgcgcggc | 1740 |
| catttcggtg cttccgcatc tgtcggttat cagtggtaa | 1779 |

<210> SEQ ID NO 14
<211> LENGTH: 1770
<212> TYPE: DNA

<213> ORGANISM: Neisseria meningitidis

<400> SEQUENCE: 14

| | | | | | |
|---|---|---|---|---|---|
| atgaacaaaa | tataccgcat | catttggaat | agtgccctca | atgcctgggt | agtcgtatcc | 60 |
| gagctcacac | gcaaccacac | caaacgcgcc | tccgcaaccg | tggcgaccgc | cgtattggcg | 120 |
| acactgctgt | ccgcaacggt | tcaggcgaat | gctaccgata | ccgatgaaga | tgaagagtta | 180 |
| gaatccgtag | cacgctctgc | tctggtgttg | caattcatga | tcgataaaga | aggcaatgga | 240 |
| gaaatcgaat | ctacaggaga | tataggttgg | agtatatatt | acgacgatca | caacactcta | 300 |
| cacggcgcaa | ccgttaccct | caaagccggc | gacaacctga | aaatcaaaca | aagcggcaaa | 360 |
| gacttcaccct | actcgctgaa | aaagagctg | aaagacctga | ccagtgttga | aactgaaaaa | 420 |
| ttatcgtttg | gcgcaaacgg | taataaagtc | aacatcacaa | gcgacaccaa | aggcttgaat | 480 |
| tttgcgaaag | aaacggctgg | gacgaacggc | gaccccacgg | ttcatctgaa | cggtatcggt | 540 |
| tcgactttga | ccgatacgct | tgcgggttct | tctgcttctc | acgttgatgc | gggtaaccaa | 600 |
| agtacacatt | acactcgtgc | agcaagtatt | aaggatgtgt | tgaatgcggg | ttggaatatt | 660 |
| aagggtgtta | aaactggctc | aacaactggt | caatcagaaa | atgtcgattt | cgtccgcact | 720 |
| tacgacacag | tcgagttctt | gagcgcagat | acgaaaacaa | cgactgttaa | tgtggaaagc | 780 |
| aaagacaacg | gcaagagaac | cgaagttaaa | atcggtgcga | agacttctgt | tattaaagaa | 840 |
| aaagacggta | agttggttac | tggtaaaggc | aaaggcgaga | atggttcttc | tacagacgaa | 900 |
| ggcgaaggct | tagtgactgc | aaaagaagtg | attgatgcag | taaacaaggc | tggttggaga | 960 |
| atgaaaacaa | caaccgctaa | tggtcaaaca | ggtcaagctg | acaagtttga | aaccgttaca | 1020 |
| tcaggcacaa | aagtaacctt | tgctagtggt | aatggtacaa | ctgcgactgt | aagtaaagat | 1080 |
| gatcaaggca | acatcactgt | taagtatgat | gtaaatgtcg | gcgatgccct | aaacgtcaat | 1140 |
| cagctgcaaa | acagcggttg | gaatttggat | tccaaagcgg | ttgcaggttc | ttcgggcaaa | 1200 |
| gtcatcagcg | gcaatgtttc | gccgagcaag | ggaaagatgg | atgaaaccgt | caacattaat | 1260 |
| gccggcaaca | catcgagat | acccgcaac | ggcaaaaata | tcgacatcgc | cacttcgatg | 1320 |
| accccgcaat | tttccagcgt | ttcgctcggc | gcggggcgg | atgcgcccac | tttaagcgtg | 1380 |
| gatgacgagg | gcgcgttgaa | tgtcggcagc | aaggatgcca | acaaacccgt | ccgcattacc | 1440 |
| aatgtcgccc | cgggcgttaa | agaggggat | gttacaaacg | tcgcacaact | taaggtgtg | 1500 |
| gcgcaaaact | tgaacaaccg | catcgacaat | gtgaacggca | acgcgcgcgc | gggtatcgcc | 1560 |
| caagcgattg | caaccgcagg | tttggctcag | gcctatttgc | ccggcaagag | tatgatggcg | 1620 |
| atcggcggcg | gtacttatct | cggcgaagcc | ggttacgcca | tcggctactc | gagcatttct | 1680 |
| gacactggga | attgggttat | caagggcacg | gcttccggca | attcgcgcgg | tcatttcggt | 1740 |
| acttccgcat | ctgtcggtta | tcagtggtaa | | | | 1770 |

<210> SEQ ID NO 15
<211> LENGTH: 1785
<212> TYPE: DNA
<213> ORGANISM: Neisseria meningitidis

<400> SEQUENCE: 15

| | | | | | |
|---|---|---|---|---|---|
| atgaacaaaa | tataccgcat | catttggaat | agtgccctca | atgcctgggt | cgccgtatcc | 60 |
| gagctcacac | gcaaccacac | caaacgcgcc | tccgcaaccg | tggcgaccgc | cgtattggcg | 120 |
| acactgttgt | tgcaacggt | tcaggcgagt | actaccgatg | acgacgattt | atatttagaa | 180 |
| cccgtacaac | gcactgctgt | cgtgttgagc | ttccgttccg | ataaagaagg | cacgggagaa | 240 |

```
aaagaagtta cagaagattc aaattgggga gtatatttcg acaagaaagg agtactaaca    300
gccggaacaa tcaccctcaa agccggcgac aacctgaaaa tcaaacaaaa caccaatgaa    360
aacaccaatg ccagtagctt cacctactcg ctgaaaaaag acctcacaga tctgaccagt    420
gttggaactg aaaaattatc gtttagcgca aacagcaata aagtcaacat cacaagcgac    480
accaaaggct tgaatttcgc gaaaaaacg gctgagacca acggcgacac cacggttcat    540
ctgaacggta tcggttcgac tttgaccgat acgctgctga ataccggagc gaccacaaac    600
gtaaccaacg acaacgttac cgatgacgag aaaaaacgtg cggcaagcgt taaagacgta    660
ttaaacgcag gctggaacat taaaggcgtt aaacccggta caacagcttc cgataacgtt    720
gatttcgtcc gcacttacga cacagtcgag ttcttgagcg cagatacgaa aacaacgact    780
gttaatgtgg aaagcaaaga caacggcaag agaaccgaag ttaaaatcgg tgcgaagact    840
tctgttatca agaaaaaga cggtaagttg gttactggta aagacaaagg cgagaatgat    900
tcttctacag acaaaggcga aggcttagtg actgcaaaag aagtgattga tgcagtaaac    960
aaggctggtt ggagaatgaa acaacaacc gctaatggtc aaacaggtca agctgacaag   1020
tttgaaaccg ttacatcagg cacaaatgta acctttgcta gtggtaaagg tacaactgcg   1080
actgtaagta aagatgatca aggcaacatc actgttatgt atgatgtaaa tgtcggcgat   1140
gccctaaacg tcaatcagct gcaaaacagc ggttggaatt tggattccaa agcggttgca   1200
ggttcttcgg gcaaagtcat cagcggcaat gtttcgccga gcaagggaaa gatggatgaa   1260
accgtcaaca ttaatgccgg caacaacatc gagattaccc gcaacggcaa aaatatcgac   1320
atcgccactt cgatgacccc gcaatttttcc agcgtttcgc tcggcgcggg ggcggatgcg   1380
cccactttaa gcgtggatga cgagggcgcg ttgaatgtcg gcagcaagga tgccaacaaa   1440
cccgtccgca ttaccaatgt cgccccgggc gttaaagagg gggatgttac aaacgtcgca   1500
caacttaaag gcgtggcgca aaacttgaac aaccacatcg acaatgtgga cggcaacgcg   1560
cgtgcgggca tcgcccaagc gattgcaacc gcaggtctgg ttcaggcgta tctgcccggc   1620
aagagtatga tggcgatcgg cggcggcact tatcgcggcg aagccggtta tgccatcggc   1680
tactcaagca tttccgacgg cggaaattgg attatcaaag gcacggcttc cggcaattcg   1740
cgcggccatt tcggtgcttc cgcatctgtc ggttatcagt ggtaa                   1785

<210> SEQ ID NO 16
<211> LENGTH: 1776
<212> TYPE: DNA
<213> ORGANISM: Neisseria meningitidis

<400> SEQUENCE: 16
atgaacgaaa tattgcgcat catttggaat agcgccctca atgcctgggt cgttgtatcc     60
gagctcacac gcaaccacac caaacgcgcc tccgcaaccg tgaagaccgc cgtattggcg    120
actctgttgt ttgcaacggt tcaggcaagt gctaacaatg aagagcaaga agaagattta    180
tatttagacc ccgtgctacg cactgttgcc gtgttgatag tcaattccga taaagaaggc    240
acggagaaaa agaaaaagt agaagaaaat tcagattggg cagtatattt caacgagaaa    300
ggagtactaa cagccagaga atcaccctc aaagccggcg acaacctgaa atcaaacaa     360 aacggcacaa acttcaccta ctcgctgaaa aaagacctca cagatctgac cagtgttgga    420
actgaaaaat atcgtttag cgcaaacggc aataaagtca acatcacaag cgacaccaaa    480
ggcttgaatt ttgcgaaaga aacgctggga cgaacggcg acaccacggt tcatctgaac    540
ggtattggtt cgactttgac cgatacgctg ctgaataccg gagcgaccac aaacgtaacc    600
```

```
aacgacaacg ttaccgatga cgagaaaaaa cgtgcggcaa gcgttaaaga cgtattaaac      660
gctggctgga acattaaagg cgttaaaccc ggtacaacag cttccgataa cgttgatttc      720
gtccgcactt acgacacagt cgagttcttg agcgcagata cgaaaacaac gactgttaat      780
gtggaaagca agacaacgg caagaaaacc gaagttaaaa tcggtgcgaa gacttctgtt       840
attaaagaaa aagacggtaa gttggttact ggtaaagaca aggcgagaa tggttcttct       900 acagacgaag gcgaaggctt agtgactgca aagaagtga ttgatgcagt aaacaaggct       960
ggttggagaa tgaaaacaac aaccgctaat ggtcaaacag gtcaagctga caagtttgaa      1020
accgttacat caggcacaaa tgtaaccttt gctagtggta aggtacaac tgcgactgta       1080 agtaaagatg atcaaggcaa catcactgtt atgtatgatg taaatgtcgg cgatgcccta      1140
aacgtcaatc agctgcaaaa cagcggttgg aatttggatt ccaaagcggt tgcaggttct      1200
tcgggcaaag tcatcagcgg caatgtttcg ccgagcaagg gaaagatgga tgaaaccgtc      1260
aacattaatg ccggcaacaa catcgagatt acccgcaacg gtaaaaatat cgacatcgcc      1320
acttcgatga ccccgcagtt ttccagcgtt tcgctcggcg cggggcgga tgcgcccact       1380 ttgagcgtgg atggggacgc attgaatgtc ggcagcaaga aggacaacaa acccgtccgc      1440
attaccaatg tcgccccggg cgttaaagag ggggatgtta caaacgtcgc acaacttaaa      1500
ggcgtggcgc aaaacttgaa caaccgcatc gacaatgtgg acggcaacgc gcgtgcgggc      1560
atcgcccaag cgattgcaac cgcaggtctg gttcaggcgt atttgcccgg caagagtatg      1620
atggcgatcg gcgccggcac ttatcgcggc gaagccggtt acgccatcgg ctactccagt      1680
atttccgacg gcggaaattg gattatcaaa ggcacggctt ccggcaattc gcgcggccat      1740
ttcggtgctt ccgcatctgt cggttatcag tggtaa                               1776

<210> SEQ ID NO 17
<211> LENGTH: 1800
<212> TYPE: DNA
<213> ORGANISM: Neisseria meningitidis

<400> SEQUENCE: 17
atgaacaaaa tataccgcat catttggaat agtgccctca atgcctgggt cgccgtatcc       60
gagctcacac gcaaccacac caaacgcgcc tccgcaaccg tgaagaccgc cgtattggcg      120
acgctgttgt ttgcaacggt tcaggcgaat gctaccgatg aagatgaaga agaagagtta      180
gaacccgtag tacgctctgc tctggtgttg caattcatga tcgataaaga aggcaatgga      240
gaaaacgaat ctacaggaaa tataggttgg agtatatatt acgacaatca caacactcta      300
cacggcgcaa ccgttaccct caaagccggc gacaacctga aaatcaaaca aaacaccaat      360
aaaaacacca atgaaaacac caatgacagt agcttcacct actcgctgaa aaagacctc      420 acagatctga ccagtgttga aactgaaaaa ttatcgtttg gcgcaaacgg caataaagtc      480
aacatcacaa gcgacaccaa aggcttgaat ttcgcgaaag aaacggctgg gacgaacggc      540
gacaccacgg ttcatctgaa cggtattggt tcgactttga ccgatacgct gctgaatacc      600
ggagcgacca caaacgtaac caacgacaac gttaccgatg acaagaaaaa acgtgcggca      660
agcgttaaag acgtattaaa cgcaggctgg aacattaaag gcgttaaacc cggtacaaca      720
gcttccgata acgttgattt cgtccacact tacgacacag tcgagttctt gagcgcagat      780
acgaaaacaa cgactgttaa tgtggaaagc aaagacaacg gcaagagaac cgaagttaaa      840
atcggtgcga agacttctgt tattaaagaa aagacggta agttggttac tggtaaaggc       900
aaaggcgaga atggttcttc tacagacgaa ggcgaaggct tagtgactgc aaaagaagtg      960
```

-continued

```
attgatgcag taaacaaggc tggttggaga atgaaaacaa caaccgctaa tggtcaaaca   1020
ggtcaagctg acaagtttga aaccgttaca tcaggcacaa atgtaaccct tgctagtggt   1080
aaaggtacaa ctgcgactgt aagtaaagat gatcaaggca acatcactgt aagtatgat    1140 gtaaatgtcg gcgatgccct aaacgtcaat cagctgcaaa acagcggttg gaatttggat   1200
tccaaagcgg ttgcaggttc ttcgggcaaa gtcatcagcg gcaatgtttc gccgagcaag   1260
ggaaagatga tgaaaccgt caacattaat gccggcaaca catcgagat acccgcaac     1320 ggtaaaaata tcgacatcgc cacttcgatg accccgcagt tttccagcgt ttcgctcggc   1380 gcggggggcgg atgcgcccac tttgagcgtg atgacaagg gcgcgttgaa tgtcggcagc   1440
aaggatgcca acaaacccgt ccgcattacc aatgtcgccc cgggcgttaa agagggggat   1500
gttacaaacg tcgcacaact taaaggcgtg cgcaaaaact tgaacaaccg catcgacaat   1560
gtggacggca acgcgcgtgc gggcatcgcc caagcgattg caaccgcagg tctggttcag   1620
gcgtatctgc ccggcaagag tatgatggcg atcggcggcg gcacttatcg cggcgaagcc   1680
ggttacgcca tcggctactc cagtatttcc gacggcggaa attggattat caaaggcacg   1740
gcttccggca attcgcgcgg tcatttcggt gcttccgcat ctgtcggtta tcagtggtaa   1800
```

<210> SEQ ID NO 18
<211> LENGTH: 1797
<212> TYPE: DNA
<213> ORGANISM: Neisseria meningitidis

<400> SEQUENCE: 18

```
atgaacaaaa tataccgcat catttggaat agtgccctca atgcctgggt cgtcgtatcc     60
gagctcacac gcaaccacac caaacgcgcc tccgcaaccg tggcgaccgc cgtattggcg    120
acactgttgt ttgcaacggt tcaggcgaat gctaccgatg acgacgattt atatttagaa    180
cccgtacaac gcactgctgt cgtgttgagc ttccgttccg ataaagaagg cacgggagaa    240
aaagaaggta cagaagattc aaattgggca gtatatttcg acgagaaaag agtactaaaa    300
gccggagcaa tcaccctcaa agccggcgac aacctgaaaa tcaaacaaaa caccaatgaa    360
aacaccaatg aaaacaccaa tgacagtagc ttcacctact ccctgaaaaa agacctcaca    420
gatctgacca gtgttgaaac tgaaaaatta tcgtttggcg caaacggtaa taaagtcaac    480
atcacaagcg acaccaaagg cttgaatttt gcgaaagaaa cggctgggac gaacggcgac    540
cccacggttc atctgaacgg tatcggttcg actttgaccg atacgctgct gaataccgga    600
gcgaccacaa acgtaaccaa cgacaacgtt accgatgacg agaaaaaacg tgcggcaagc    660
gttaaagacg tattaaacgc aggctggaac attaaaggcg ttaaacccgg tacaacagct    720
tccgataacg ttgatttcgt ccgcacttac gacacagtcg agttcttgag cgcagatacg    780
aaaacaacga ctgttaatgt ggaaagcaaa gacaacggca agaaaaccga agttaaaatc    840
ggtgcgaaga cttctgttat taagaaaaaa gacggtaagt tggttactgg taaaggcaaa    900
gacgagaatg gttcttctac agacgaaggc gaaggcttag tgactgcaaa agaagtgatt    960
gatgcagtaa acaaggctgg ttggagaatg aaaacaacaa ccgctaatgg tcaaacaggt   1020
caagctgaca gtttgaaac cgttacatca ggcacaaaag taacctttgc tagtggtaat    1080
ggtacaactg cgactgtaag taaagatgat caaggcaaca tcactgttaa gtatgatgta   1140
aatgtcggcg atgccctaaa cgtcaatcag ctgcaaaaca gcggttggaa tttggattcc   1200
aaagcggttg caggttcttc gggcaaagtc atcagcggca atgtttcgcc gagcaaggga   1260
aagatggatg aaaccgtcaa cattaatgcc ggcaacaaca tcgagattac cgcaacggc    1320
```

-continued

```
aaaaatatcg acatcgccac ttcgatgacc ccgcaatttt ccagcgtttc gctcggcgcg    1380
ggggcggatg cgcccacttt aagcgtggat gacgagggcg cgttgaatgt cggcagcaag    1440
gatgccaaca aacccgtccg cattaccaat gtcgccccgg gcgttaaaga gggggatgtt    1500
acaaacgtcg cacaacttaa aggtgtggcg caaaacttga acaaccgcat cgacaatgtg    1560
gacggcaacg cgcgcgcggg tatcgcccaa gcgattgcaa ccgcaggttt ggctcaggcg    1620
tatttgcccg gcaagagtat gatggcgatc ggcggcggta cttatcgcgg cgaagccggt    1680
tacgccatcg gctactcgag catttctgac actgggaatt gggttatcaa gggcacggct    1740
tccggcaatt cgcgcggcca tttcggtgct ccgcatctg tcggttatca gtggtaa      1797
```

<210> SEQ ID NO 19
<211> LENGTH: 1797
<212> TYPE: DNA
<213> ORGANISM: Neisseria meningitidis

<400> SEQUENCE: 19

```
atgaacaaaa tatcccgcat catttggaat agtgccctca atgcctgggt cgtcgtatcc      60
gagctcacac gcaaccacac caaacgcgcc tccgcaaccg tggcgaccgc cgtattggcg     120
acactgttgt ttgcaacggt tcaggcgaat gctaccgatg acgacgattt atatttagaa     180
cccgtacaac gcactgctgt cgtgttgagc ttccgttccg ataaagaagg cacgggagaa     240
aaagaaggta cagaagattc aaattgggca gtatatttcg acgagaaaag agtactaaaa     300
gccggagcaa tcaccctcaa agccggcgac aacctgaaaa tcaaacaaaa caccaatgaa     360
aacaccaatg aaaacaccaa tgacagtagc ttcacctact ccctgaaaaa agacctcaca     420
gatctgacca gtgttgaaac tgaaaaatta tcgtttggcg caaacggtaa taaagtcaac     480
atcacaagcg acaccaaagg cttgaatttt gcgaaagaaa cggctgggac gaacggcgac     540
cccacggttc atctgaacgg tatcggttcg actttgaccg atacgctgct gaataccgga     600
gcgaccacaa acgtaaccaa cgacaacgtt accgatgacg agaaaaaacg tgcggcaagc     660
gttaaagacg tattaaacgc aggctggaac attaaaggcg ttaaacccgg tacaacagct     720
tccgataacg tcgatttcgt ccgcacttac gacacagtcg agttcttgag cgcagatacg     780
aaaacaacga ctgttaatgt ggaaagcaaa gacaacggca agagaaccga gttaaaatc      840 ggtgcgaaga cttctgttat taaagaaaaa gacggtaagt tggttactgg taaaggcaaa     900
ggcgagaatg gttcttctac agacgaaggc gaaggcttag tgactgcaaa agaagtgatt     960
gatgcagtaa acaaggctgg ttggagaatg aaaacaacaa ccgctaatgg tcaaacaggt    1020
caagctgaca gtttgaaaac cgttacatca ggcacaaaag taacctttgc tagtggtaat    1080
ggtacaactg cgactgtaag taaagatgat caaggcaaca tcactgttaa gtatgatgta    1140
aatgtcggcg atgccctaaa cgtcaatcag ctgcaaaaca gcggttggaa tttggattcc    1200
aaagcggttg caggttcttc gggcaaagtc atcagcggca atgtttcgcc gagcaaggga    1260
aagatggatg aaaccgtcaa cattaatgcc ggcaacaaca tcgagattac ccgcaacggc    1320
aaaaatatcg acatcgccac ttcgatgacc ccgcaatttt ccagcgtttc gctcggcgcg    1380
ggggcggatg cgcccacttt aagcgtggat gacgagggcg cgttgaatgt cggcagcaag    1440
gatgccaaca aacccgtccg cattaccaat gtcgccccgg gcgttaaaga gggggatgtt    1500
acaaacgtcg cacaacttaa aggtgtggcg caaaacttga acaaccgcat cgacaatgtg    1560
gacggcaacg cgcgcgcggg tatcgcccaa gcgattgcaa ccgcaggttt ggctcaggcc    1620
tatttgcccg gcaagagtat gatggcgatc ggcggcggta cttatcgcgg cgaagccggt    1680
```

| | |
|---|---|
| tacgccatcg gctactcgag catttctgac actgggaatt gggttatcaa gggcacggct | 1740 |
| tccggcaatt cgcgcggtca tttcggtact tccgcatctg tcggttatca gtggtaa | 1797 |

<210> SEQ ID NO 20
<211> LENGTH: 1785
<212> TYPE: DNA
<213> ORGANISM: Neisseria meningitidis

<400> SEQUENCE: 20

| | |
|---|---|
| atgaacaaaa tataccgcat catttggaat agtgccctca atgcctgggt cgtcgtatcc | 60 |
| gagctcacac gcaaccacac caaacgcgcc tccgcaaccg tggcgaccgc cgtattggcg | 120 |
| acactgttgt ttgcaacggt tcaggcgaat gctaccgatg acgacgattt atatttagaa | 180 |
| cccgtacaac gcactgctgt cgtgttgagc ttccgttccg ataaagaagg cacgggagaa | 240 |
| aaagaaggta cagaagattc aaattgggca gtatatttcg acgagaaaag agtactaaaa | 300 |
| gccggagcaa tcaccctcaa agccggcgac aacctgaaaa tcaaacaaaa caccaatgaa | 360 |
| aacaccaatg acagtagctt cacctactcc ctgaaaaaag acctcacaga tctgaccagt | 420 |
| gttgaaactg aaaaattatc gtttggcgca aacggtaata agtcaacat cacaagcgac | 480 |
| accaaaggct tgaattttgc gaaagaaacg gctgggacga acggcgaccc cacggttcat | 540 |
| ctgaacggta tcggttcgac tttgaccgat acgctgctga ataccggagc gaccacaaac | 600 |
| gtaaccaacg acaacgttac cgatgacgag aaaaaacgtg cggcaagcgt taaagacgta | 660 |
| ttaaacgcag gctggaacat taaaggcgtt aaacccggta caacagcttc cgataacgtt | 720 |
| gatttcgtcc gcacttacga cacagtcgag ttcttgagcg cagatacgaa aacaacgact | 780 |
| gttaatgtgg aaagcaaaga caacggcaag aaaaccgaag ttaaaatcgg tgcgaagact | 840 |
| tctgttatta agaaaaaga cggtaagttg gttactggta aaggcaaaga cgagaatggt | 900 |
| tcttctacag acgaaggcga aggcttagtg actgcaaaag aagtgattga tgcagtaaac | 960 |
| aaggctggtt ggagaatgaa aacaacaacc gctaatggtc aaacaggtca agctgacaag | 1020 |
| tttgaaaccg ttacatcagg cacaaatgta acctttgcta gtggtaaagg tacaactgcg | 1080 |
| actgtaagta aagatgatca aggcaacatc actgttaagt atgatgtaaa tgtcggcgat | 1140 |
| gccctaaacg tcaatcagct gcaaaacagc ggttggaatt tggattccaa agcggttgca | 1200 |
| ggttcttcgg gcaaagtcat cagcggcaat gtttcgccga gcaagggaaa gatggatgaa | 1260 |
| accgtcaaca ttaatgccgg caacaacatc gagattaccc gcaacggtaa aaatatcgac | 1320 |
| atcgccactt cgatggcgcc gcagtttccc agcgtttcgc tcggtgcggg gcggatgcgc | 1380 |
| cccactttga gcgtggatga cgagggcgcg ttgaatgtcg gcagcaagga taccaacaaa | 1440 |
| cccgtccgca ttaccaatgt cgccccgggc gttaaagagg gggatgttac aaacgtcgca | 1500 |
| caacttaaag gcgtggcgca aaacttgaac aaccgcatcg acaatgtgga cggcaacgcg | 1560 |
| cgtgcgggca tcgcccaagc gattgcaacc gcaggtctag ttcaggcgta tctgcccggc | 1620 |
| aagagtatga tggcgatcgg cggcgacact tatcgcggcg aagccggtta cgccatcggc | 1680 |
| tactcaagta tttccgacgg cggaaattgg attatcaaag gcacggcttc cggcaattcg | 1740 |
| cgcggccatt tcggtgcttc cgcatctgtc ggttatcaat ggtaa | 1785 |

<210> SEQ ID NO 21
<211> LENGTH: 1779
<212> TYPE: DNA
<213> ORGANISM: Neisseria meningitidis

<400> SEQUENCE: 21

| | |
|---|---|
| atgaacaaaa tataccgcat catttggaat agtgccctca atgcctgggt cgccgtatcc | 60 |
| gagctcacac gcaaccacac caaacgcgcc tccgcaaccg tgaagaccgc cgtattggcg | 120 |
| acactgttgt ttgcaacggt tcaggcgaat gctaccgatg aagatgaaga agaagagtta | 180 |
| gaatccgtac aacgctctgt cgtagggagc attcaagcca gtatggaagg cagcggcgaa | 240 |
| ttggaaacga tatcattatc aatgactaac gacagcaagg aatttgtaga cccatacata | 300 |
| gtagttaccc tcaaagccgg cgacaacctg aaaatcaaac aaaacaccaa tgaaaacacc | 360 |
| aatgccagta gcttcaccta ctcgctgaaa aaagacctca caggcctgat caatgttgaa | 420 |
| actgaaaaat tatcgtttgg cgcaaacggc aagaaagtca acatcataag cgacaccaaa | 480 |
| ggcttgaatt tcgcgaaaga aacggctggg acgaacggcg acaccacggt tcatctgaac | 540 |
| ggtatcggtt cgactttgac cgatacgctt gcgggttctt ctgcttctca cgttgatgcg | 600 |
| ggtaaccaaa gtacacatta cactcgtgca gcaagtatta aggatgtgtt gaatgcgggt | 660 |
| tggaatatta agggtgttaa aactggctca acaactggtc aatcagaaaa tgtcgatttc | 720 |
| gtccgcactt acgacacagt cgagttcttg agcgcagata cgaaaacaac gactgttaat | 780 |
| gtggaaagca aagacaacgg caagagaacc gaagttaaaa tcggtgcgaa gacttctgtt | 840 |
| attaaagaaa agacggtaa gttggttact ggtaaaggca aaggcgagaa tggttcttct | 900 |
| acagacgaag gcgaaggctt agtgactgca aaagaagtga ttgatgcagt aaacaaggct | 960 |
| ggttggagaa tgaaaacaac aaccgctaat ggtcaaacag gtcaagctga caagtttgaa | 1020 |
| accgttacat caggcacaaa tgtaaccttt gctagtggta aggtacaac tgcgactgta | 1080 |
| agtaaagatg atcaaggcaa catcactgtt atgtatgatg taaatgtcgg cgatgcccta | 1140 |
| aacgtcaatc agctgcaaaa cagcggttgg aatttggatt ccaaagcggt tgcaggttct | 1200 |
| tcgggcaaag tcatcagcgg caatgtttcg ccgagcaagg gaaagatgga tgaaaccgtc | 1260 |
| aacattaatg ccggcaacaa catcgagatt agccgcaacg gtaaaaatat cgacatcgcc | 1320 |
| acttcgatgg cgccgcagtt ttccagcgtt tcgctcggcg cggggggcaga tgcgcccact | 1380 |
| ttaagcgtgg atgacgaggg cgcgttgaat gtcggcagca aggatgccaa caaacccgtc | 1440 |
| cgcattacca atgtcgcccc gggcgttaaa gaggggatg ttacaaacgt cgcacaactt | 1500 |
| aaaggcgtgg cgcaaaactt gaacaaccgc atcgacaatg tggacggcaa cgcgcgtgcg | 1560 |
| ggcatcgccc aagcgattgc aaccgcaggt ctggttcagg cgtatctgcc cggcaagagt | 1620 |
| atgatggcga tcggcggcgg cacttatcgc ggcgaagccg gttacgccat cggctactcc | 1680 |
| agtatttccg acgcggaaa ttggattatc aaaggcacgg cttccggcaa ttcgcgcggc | 1740 |
| catttcggtg cttccgcatc tgtcggttat cagtggtaa | 1779 |

<210> SEQ ID NO 22
<211> LENGTH: 1815
<212> TYPE: DNA
<213> ORGANISM: Neisseria meningitidis
<220> FEATURE:
<221> NAME/KEY: misc_feature
<223> OTHER INFORMATION: “n” is any nucleotide, synonymous nucleotide or absent nucleotide at a corresponding position in any one of SEQ ID NOS:12-2

<400> SEQUENCE: 22
atgaacnaaa tatnncgcat catttggaat agngccctca atgcntgggt ngnngtatcc 60
gagctcacac gcaaccacac caaacgcgcc tccgcaaccg tgnngaccgc cgtattggcg 120
acnctgntgt nngcaacggt tcaggcnant nctancnatn nngannnnnn nnnngannna 180
nanttagann ccgtnnnacg cnctgnnnnn gnnnnnnnnn tnnnnnncnn tanngaaggc 240

-continued

```
anngnngaan nngaannnnn annnnnnnnn nnnnnnnnnn nnnnnnannn nnnnnnnnnn    300
nnnnnnnnnn nnnnnnnnnn nntnaccctc aaagccggcg acaacctgaa atcaaacaa     360
ancnnnnnnn nnnnnnnnnn nnnnnnnnnn nnnnnnnnnn ncttcaccta ctcnctgaaa    420
aaaganctna nagnnctgan cantgttgna actgaaaaat tatcgtttng cgcaaacngn    480
aanaaagtca acatcanaag cgacaccaaa ggcttgaatt tngcgaaana acggctgng     540
acnaacggcg acnccacggt tcatctgaac ggtatnggtt cgactttgac cgatangctn    600
nngnntncnn nngcnncnnn nnnngnnncn nnnnacnann ntacnnatna cnnnnnnann    660
cgtgcngcaa gnnttaanga ngtnttnaan gcnggntgga anattaangg ngttaaancn    720
ggnncaacan ctnnnnnntc nganaangtn gatttcgtcc ncacttacga cacagtcgag    780
ttcttgagcg cagatacgaa acaacgact gttaatgtgg aaagcaaaga caacggcaag    840
anaaccgaag ttaaaatcgg tgcgaagact tctgttatna aagaaaaaga cggtaagttg    900
gttactggta aagncaaagn cgagaatgnt tcttctacag acnaaggcga aggcttagtg    960
actgcaaaag aagtgattga tgcagtaaac aaggctggtt ggagaatgaa acaacaacc    1020
gctaatggtc aaacaggtca agctgacaag tttgaaaccg ttacatcagg cacaaangta    1080
accttttgcta gtggtaangg tacaactgcg actgtaagta aagatgatca aggcaacatc    1140
actgttangt atgatgtaaa tgtcggcgat gccctaaacg tcaatcagct gcaaaacagc    1200
ggttggaatt tggattccaa agcggttgca ggttcttcgg gcaaagtcat cagcggcaat    1260
gtttcgccga gcaagggaaa gatggatgaa accgtcaaca ttaatgccgg caacaacatc    1320
gagattancc gcaacggnaa aaatatcgac atcgccactt cgatgncncc gcanttttcc    1380
agcgtttcgc tcggngcggg ggcngatgcg cccactttna gcgtggatnn nnnggncgcn    1440
ttgaatgtcg gcagcaagna nnncaacaaa cccgtccgca ttaccaatgt cgccccgggc    1500
gttaaagagg gggatgttac aaacgtcgcn caacttaaag gngtggcgca aaacttgaac    1560
aaccncatcg acaatgtgna cggcaacgcg cgngcgggna tcgcccaagc gattgcaacc    1620
gcaggtntng ntcaggcnta tntgcccggc aagagtatga tggcgatcgg cggcgnnact    1680
tatcncggcg aagccggtta ngccatcggc tactcnagna tttcngncnn nggnaattgg    1740
nttatcaang gcacggcttc cggcaattcg cgcggncatt tcggtncttc cgcatctgtc    1800
ggttatcant ggtaa                                                    1815
```

<210> SEQ ID NO 23
<211> LENGTH: 512
<212> TYPE: PRT
<213> ORGANISM: Neisseria meningitidis

<400> SEQUENCE: 23

```
Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Thr Asp Leu Thr Ser Val Gly Thr Glu Lys
    50                  55                  60

Leu Ser Phe Ser Ala Asn Gly Asn Lys Val Asn Ile Thr Ser Asp Thr
65                  70                  75                  80

Lys Gly Leu Asn Phe Ala Lys Glu Thr Ala Gly Thr Asn Gly Asp Thr
                85                  90                  95
```

```
Thr Val His Leu Asn Gly Ile Gly Ser Thr Leu Thr Asp Thr Leu Leu
            100                 105                 110

Asn Thr Gly Ala Thr Thr Asn Val Thr Asn Asp Asn Val Thr Asp Asp
            115                 120                 125

Glu Lys Lys Arg Ala Ala Ser Val Lys Asp Val Leu Asn Ala Gly Trp
130                 135                 140

Asn Ile Lys Gly Val Lys Pro Gly Thr Thr Ala Ser Asp Asn Val Asp
145                 150                 155                 160

Phe Val Arg Thr Tyr Asp Thr Val Glu Phe Leu Ser Ala Asp Thr Lys
                165                 170                 175

Thr Thr Thr Val Asn Val Glu Ser Lys Asp Asn Gly Lys Lys Thr Glu
            180                 185                 190

Val Lys Ile Gly Ala Lys Thr Ser Val Ile Lys Glu Lys Asp Gly Lys
            195                 200                 205

Leu Val Thr Gly Lys Asp Lys Gly Glu Asn Gly Ser Ser Thr Asp Glu
            210                 215                 220

Gly Glu Gly Leu Val Thr Ala Lys Glu Val Ile Asp Ala Val Asn Lys
225                 230                 235                 240

Ala Gly Trp Arg Met Lys Thr Thr Thr Ala Asn Gly Gln Thr Gly Gln
                245                 250                 255

Ala Asp Lys Phe Glu Thr Val Thr Ser Gly Thr Asn Val Thr Phe Ala
            260                 265                 270

Ser Gly Lys Gly Thr Thr Ala Thr Val Ser Lys Asp Asp Gln Gly Asn
            275                 280                 285

Ile Thr Val Met Tyr Asp Val Asn Val Gly Asp Ala Leu Asn Val Asn
            290                 295                 300

Gln Leu Gln Asn Ser Gly Trp Asn Leu Asp Ser Lys Ala Val Ala Gly
305                 310                 315                 320

Ser Ser Gly Lys Val Ile Ser Gly Asn Val Ser Pro Ser Lys Gly Lys
                325                 330                 335

Met Asp Glu Thr Val Asn Ile Asn Ala Gly Asn Asn Ile Glu Ile Thr
            340                 345                 350

Arg Asn Gly Lys Asn Ile Asp Ile Ala Thr Ser Met Thr Pro Gln Phe
            355                 360                 365

Ser Ser Val Ser Leu Gly Ala Gly Ala Asp Ala Pro Thr Leu Ser Val
            370                 375                 380

Asp Gly Asp Ala Leu Asn Val Gly Ser Lys Lys Asp Asn Lys Pro Val
385                 390                 395                 400

Arg Ile Thr Asn Val Ala Pro Gly Val Lys Glu Gly Asp Val Thr Asn
                405                 410                 415

Val Ala Gln Leu Lys Gly Val Ala Gln Asn Leu Asn Asn Arg Ile Asp
            420                 425                 430

Asn Val Asp Gly Asn Ala Arg Ala Gly Ile Ala Gln Ala Ile Ala Thr
            435                 440                 445

Ala Gly Leu Val Gln Ala Tyr Leu Pro Gly Lys Ser Met Met Ala Ile
            450                 455                 460

Gly Gly Gly Thr Tyr Arg Gly Glu Ala Gly Tyr Ala Ile Gly Tyr Ser
465                 470                 475                 480

Ser Ile Ser Asp Gly Gly Asn Trp Ile Ile Lys Gly Thr Ala Ser Gly
                485                 490                 495

Asn Ser Arg Gly His Phe Gly Ala Ser Ala Ser Val Gly Tyr Gln Trp
            500                 505                 510
```

<210> SEQ ID NO 24
<211> LENGTH: 513
<212> TYPE: PRT
<213> ORGANISM: Neisseria meningitidis

<400> SEQUENCE: 24

```
Met Asn Lys Ile Tyr Arg Ile Ile Trp Asn Ser Ala Leu Asn Ala Trp
1               5                   10                  15
Val Ala Val Ser Glu Leu Thr Arg Asn His Thr Lys Arg Ala Ser Ala
            20                  25                  30
Thr Val Lys Thr Ala Val Leu Ala Thr Leu Leu Phe Ala Thr Val Gln
        35                  40                  45
Ala Asn Ala Thr Asp Glu Thr Gly Leu Ile Asn Val Glu Thr Glu Lys
    50                  55                  60
Leu Ser Phe Gly Ala Asn Gly Lys Lys Val Asn Ile Ile Ser Asp Thr
65                  70                  75                  80
Lys Gly Leu Asn Phe Ala Lys Glu Thr Ala Gly Thr Asn Gly Asp Thr
                85                  90                  95
Thr Val His Leu Asn Gly Ile Gly Ser Thr Leu Thr Asp Met Leu Leu
            100                 105                 110
Asn Thr Gly Ala Thr Thr Asn Val Thr Asn Asp Asn Val Thr Asp Asp
        115                 120                 125
Glu Lys Lys Arg Ala Ala Ser Val Lys Asp Val Leu Asn Ala Gly Trp
    130                 135                 140
Asn Ile Lys Gly Val Lys Pro Gly Thr Ala Ser Asp Asn Val Asp
145                 150                 155                 160
Phe Val Arg Thr Tyr Asp Thr Val Glu Phe Leu Ser Ala Asp Thr Lys
                165                 170                 175
Thr Thr Thr Val Asn Val Glu Ser Lys Asp Asn Gly Lys Lys Thr Glu
            180                 185                 190
Val Lys Ile Gly Ala Lys Thr Ser Val Ile Lys Glu Lys Asp Gly Lys
        195                 200                 205
Leu Val Thr Gly Lys Gly Lys Gly Glu Asn Gly Ser Ser Thr Asp Glu
    210                 215                 220
Gly Glu Gly Leu Val Thr Ala Lys Glu Val Ile Asp Ala Val Asn Lys
225                 230                 235                 240
Ala Gly Trp Arg Met Lys Thr Thr Thr Ala Asn Gly Gln Thr Gly Gln
                245                 250                 255
Ala Asp Lys Phe Glu Thr Val Thr Ser Gly Thr Lys Val Thr Phe Ala
            260                 265                 270
Ser Gly Asn Gly Thr Thr Ala Thr Val Ser Lys Asp Gln Gly Asn
        275                 280                 285
Ile Thr Val Lys Tyr Asp Val Asn Val Gly Asp Ala Leu Asn Val Asn
    290                 295                 300
Gln Leu Gln Asn Ser Gly Trp Asn Leu Asp Ser Lys Ala Val Ala Gly
305                 310                 315                 320
Ser Ser Gly Lys Val Ile Ser Gly Asn Val Ser Pro Ser Lys Gly Lys
                325                 330                 335
Met Asp Glu Thr Val Asn Ile Asn Ala Gly Asn Asn Ile Glu Ile Thr
            340                 345                 350
Arg Asn Gly Lys Asn Ile Asp Ile Ala Thr Ser Met Thr Pro Gln Phe
        355                 360                 365
Ser Ser Val Ser Leu Gly Ala Gly Ala Asp Ala Pro Thr Leu Ser Val
    370                 375                 380
Asp Asp Glu Gly Ala Leu Asn Val Gly Ser Lys Asp Ala Asn Lys Pro
```

```
                385                 390                 395                 400
Val Arg Ile Thr Asn Val Ala Pro Gly Val Lys Glu Gly Asp Val Thr
                    405                 410                 415

Asn Val Ala Gln Leu Lys Gly Val Ala Gln Asn Leu Asn Asn Arg Ile
                420                 425                 430

Asp Asn Val Asn Gly Asn Ala Arg Ala Gly Ile Ala Gln Ala Ile Ala
            435                 440                 445

Thr Ala Gly Leu Val Gln Ala Tyr Leu Pro Gly Lys Ser Met Met Ala
        450                 455                 460

Ile Gly Gly Gly Thr Tyr Leu Gly Glu Ala Gly Tyr Ala Ile Gly Tyr
465                 470                 475                 480

Ser Ser Ile Ser Ala Gly Gly Asn Trp Ile Ile Lys Gly Thr Ala Ser
                485                 490                 495

Gly Asn Ser Arg Gly His Phe Gly Ala Ser Ala Ser Val Gly Tyr Gln
                500                 505                 510

Trp

<210> SEQ ID NO 25
<211> LENGTH: 407
<212> TYPE: PRT
<213> ORGANISM: Neisseria meningitidis

<400> SEQUENCE: 25

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Val Asp Phe Val Arg Tyr Asp Thr Val Glu
        50                  55                  60

Phe Leu Ser Ala Asp Thr Lys Thr Thr Thr Val Asn Val Glu Ser Lys
65                  70                  75                  80

Asp Asn Gly Lys Lys Thr Glu Val Lys Ile Gly Ala Lys Thr Ser Val
                85                  90                  95

Ile Lys Glu Lys Asp Gly Lys Leu Val Thr Gly Lys Asp Lys Gly Glu
                100                 105                 110

Asn Gly Ser Ser Thr Asp Glu Gly Glu Gly Leu Val Thr Ala Lys Glu
            115                 120                 125

Val Ile Asp Ala Val Asn Lys Ala Gly Trp Arg Met Lys Thr Thr Thr
        130                 135                 140

Ala Asn Gly Gln Thr Gly Gln Ala Asp Lys Phe Glu Thr Val Thr Ser
145                 150                 155                 160

Gly Thr Asn Val Thr Phe Ala Ser Gly Lys Gly Thr Thr Ala Thr Val
                165                 170                 175

Ser Lys Asp Asp Gln Gly Asn Ile Thr Val Met Tyr Asp Val Asn Val
                180                 185                 190

Gly Asp Ala Leu Asn Val Asn Gln Leu Gln Asn Ser Gly Trp Asn Leu
            195                 200                 205

Asp Ser Lys Ala Val Ala Gly Ser Ser Lys Val Ile Ser Gly Asn
        210                 215                 220

Val Ser Pro Ser Lys Gly Lys Met Asp Glu Thr Val Asn Ile Asn Ala
225                 230                 235                 240

Gly Asn Asn Ile Glu Ile Thr Arg Asn Gly Lys Asn Ile Asp Ile Ala
                245                 250                 255
```

Thr Ser Met Thr Pro Gln Phe Ser Ser Val Ser Leu Gly Ala Gly Ala
            260                 265                 270

Asp Ala Pro Thr Leu Ser Val Asp Gly Asp Ala Leu Asn Val Gly Ser
        275                 280                 285

Lys Lys Asp Asn Lys Pro Val Arg Ile Thr Asn Val Ala Pro Gly Val
290                 295                 300

Lys Glu Gly Asp Val Thr Asn Val Ala Gln Leu Lys Gly Val Ala Gln
305                 310                 315                 320

Asn Leu Asn Asn Arg Ile Asp Asn Val Asp Gly Asn Ala Arg Ala Gly
                325                 330                 335

Ile Ala Gln Ala Ile Ala Thr Ala Gly Leu Val Gln Ala Tyr Leu Pro
                340                 345                 350

Gly Lys Ser Met Met Ala Ile Gly Gly Gly Thr Tyr Arg Gly Glu Ala
            355                 360                 365

Gly Tyr Ala Ile Gly Tyr Ser Ser Ile Ser Asp Gly Gly Asn Trp Ile
        370                 375                 380

Ile Lys Gly Thr Ala Ser Gly Asn Ser Arg Gly His Phe Gly Ala Ser
385                 390                 395                 400

Ala Ser Val Gly Tyr Gln Trp
                405

<210> SEQ ID NO 26
<211> LENGTH: 433
<212> TYPE: PRT
<213> ORGANISM: Neisseria meningitidis

<400> SEQUENCE: 26

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Arg Ala Ala Ser Val Lys Asp Val Leu Asn Ala Gly
    50                  55                  60

Trp Asn Ile Lys Gly Val Lys Pro Gly Thr Thr Ala Ser Asp Asn Val
65                  70                  75                  80

Asp Phe Val Arg Thr Tyr Asp Thr Val Glu Phe Leu Ser Ala Asp Thr
                85                  90                  95

Lys Thr Thr Thr Val Asn Val Glu Ser Lys Asp Asn Gly Lys Lys Thr
            100                 105                 110

Glu Val Lys Ile Gly Ala Lys Thr Ser Val Ile Lys Glu Lys Asp Gly
        115                 120                 125

Lys Leu Val Thr Gly Lys Asp Lys Gly Glu Asn Gly Ser Ser Thr Asp
    130                 135                 140

Glu Gly Glu Gly Leu Val Thr Ala Lys Glu Val Ile Asp Ala Val Asn
145                 150                 155                 160

Lys Ala Gly Trp Arg Met Lys Thr Thr Thr Ala Asn Gly Gln Thr Gly
                165                 170                 175

Gln Ala Asp Lys Phe Glu Thr Val Thr Ser Gly Thr Asn Val Thr Phe
            180                 185                 190

Ala Ser Gly Lys Gly Thr Thr Ala Thr Val Ser Lys Asp Asp Gln Gly
        195                 200                 205

Asn Ile Thr Val Met Tyr Asp Val Asn Val Gly Asp Ala Leu Asn Val
    210                 215                 220

```
Asn Gln Leu Gln Asn Ser Gly Trp Asn Leu Asp Ser Lys Ala Val Ala
225                 230                 235                 240

Gly Ser Ser Gly Lys Val Ile Ser Gly Asn Val Ser Pro Ser Lys Gly
            245                 250                 255

Lys Met Asp Glu Thr Val Asn Ile Ala Gly Asn Asn Ile Glu Ile
        260                 265                 270

Thr Arg Asn Gly Lys Asn Ile Asp Ile Ala Thr Ser Met Thr Pro Gln
            275                 280                 285

Phe Ser Ser Val Ser Leu Gly Ala Gly Ala Asp Ala Pro Thr Leu Ser
        290                 295                 300

Val Asp Gly Asp Ala Leu Asn Val Gly Ser Lys Asp Asn Lys Pro
305                 310                 315                 320

Val Arg Ile Thr Asn Val Ala Pro Gly Val Lys Glu Gly Asp Val Thr
                325                 330                 335

Asn Val Ala Gln Leu Lys Gly Val Ala Gln Asn Leu Asn Asn Arg Ile
            340                 345                 350

Asp Asn Val Asp Gly Asn Ala Arg Ala Gly Ile Ala Gln Ala Ile Ala
            355                 360                 365

Thr Ala Gly Leu Val Gln Ala Tyr Leu Pro Gly Lys Ser Met Met Ala
370                 375                 380

Ile Gly Gly Gly Thr Tyr Arg Gly Glu Ala Gly Tyr Ala Ile Gly Tyr
385                 390                 395                 400

Ser Ser Ile Ser Asp Gly Gly Asn Trp Ile Ile Lys Gly Thr Ala Ser
            405                 410                 415

Gly Asn Ser Arg Gly His Phe Gly Ala Ser Ala Ser Val Gly Tyr Gln
            420                 425                 430

Trp

<210> SEQ ID NO 27
<211> LENGTH: 502
<212> TYPE: PRT
<213> ORGANISM: Neisseria meningitidis

<400> SEQUENCE: 27

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Thr Leu Lys Ala Gly Asp Asn Leu Lys Ile Lys Gln
        50                  55                  60

Phe Thr Tyr Ser Leu Lys Lys Asp Leu Thr Asp Leu Thr Ser Val Gly
65                  70                  75                  80

Thr Glu Lys Leu Ser Phe Ser Ala Asn Gly Asn Lys Val Asn Ile Thr
                85                  90                  95

Ser Asp Thr Lys Gly Leu Asn Phe Ala Lys Glu Thr Ala Gly Thr Asn
            100                 105                 110

Gly Asp Thr Thr Val His Leu Asn Gly Ile Gly Ser Thr Leu Thr Asp
        115                 120                 125

Arg Ala Ala Ser Val Lys Asp Val Leu Asn Ala Gly Trp Asn Ile Lys
    130                 135                 140

Gly Val Lys Asn Val Asp Phe Val Arg Thr Tyr Asp Thr Val Glu Phe
145                 150                 155                 160
```

Leu Ser Ala Asp Thr Lys Thr Thr Val Asn Val Glu Ser Lys Asp
                165                 170                 175
Asn Gly Lys Lys Thr Glu Val Lys Ile Gly Ala Lys Thr Ser Val Ile
            180                 185                 190
Lys Glu Lys Asp Gly Lys Leu Val Thr Gly Lys Asp Lys Gly Glu Asn
            195                 200                 205
Gly Ser Ser Thr Asp Glu Gly Glu Gly Leu Val Thr Ala Lys Glu Val
            210                 215                 220
Ile Asp Ala Val Asn Lys Ala Gly Trp Arg Met Lys Thr Thr Thr Ala
225                 230                 235                 240
Asn Gly Gln Thr Gly Gln Ala Asp Lys Phe Glu Thr Val Thr Ser Gly
                245                 250                 255
Thr Asn Val Thr Phe Ala Ser Gly Lys Gly Thr Thr Ala Thr Val Ser
            260                 265                 270
Lys Asp Asp Gln Gly Asn Ile Thr Val Met Tyr Asp Val Asn Val Gly
            275                 280                 285
Asp Ala Leu Asn Val Asn Gln Leu Gln Asn Ser Gly Trp Asn Leu Asp
            290                 295                 300
Ser Lys Ala Val Ala Gly Ser Ser Gly Lys Val Ile Ser Gly Asn Val
305                 310                 315                 320
Ser Pro Ser Lys Gly Lys Met Asp Glu Thr Val Asn Ile Asn Ala Gly
                325                 330                 335
Asn Asn Ile Glu Ile Thr Arg Asn Gly Lys Asn Ile Asp Ile Ala Thr
            340                 345                 350
Ser Met Thr Pro Gln Phe Ser Ser Val Ser Leu Gly Ala Gly Ala Asp
            355                 360                 365
Ala Pro Thr Leu Ser Val Asp Gly Asp Ala Leu Asn Val Gly Ser Lys
            370                 375                 380
Lys Asp Asn Lys Pro Val Arg Ile Thr Asn Val Ala Pro Gly Val Lys
385                 390                 395                 400
Glu Gly Asp Val Thr Asn Val Ala Gln Leu Lys Gly Val Ala Gln Asn
                405                 410                 415
Leu Asn Asn Arg Ile Asp Asn Val Asp Gly Asn Ala Arg Ala Gly Ile
            420                 425                 430
Ala Gln Ala Ile Ala Thr Ala Gly Leu Val Gln Ala Tyr Leu Pro Gly
            435                 440                 445
Lys Ser Met Met Ala Ile Gly Gly Gly Thr Tyr Arg Gly Glu Ala Gly
            450                 455                 460
Tyr Ala Ile Gly Tyr Ser Ser Ile Ser Asp Gly Gly Asn Trp Ile Ile
465                 470                 475                 480
Lys Gly Thr Ala Ser Gly Asn Ser Arg Gly His Phe Gly Ala Ser Ala
                485                 490                 495
Ser Val Gly Tyr Gln Trp
            500

<210> SEQ ID NO 28
<211> LENGTH: 1539
<212> TYPE: DNA
<213> ORGANISM: Neisseria meningitidis

<400> SEQUENCE: 28
atgaacaaaa ataccgcat catttggaat agtgccctca atgcatgggt cgtcgtatcc      60
gagctcacac gcaaccacac caaacgcgcc tccgcaaccg tgaagaccgc cgtattggcg    120
actctgttgt ttgcaacggt tcaggcaagt gctaacaatg aaacagatct gaccagtgtt    180

| | |
|---|---|
| ggaactgaaa aattatcgtt tagcgcaaac ggcaataaag tcaacatcac aagcgacacc | 240 |
| aaaggcttga attttgcgaa agaaacggct gggacgaacg gcgacaccac ggttcatctg | 300 |
| aacggtattg gttcgacttt gaccgatacg ctgctgaata ccggagcgac cacaaacgta | 360 |
| accaacgaca acgttaccga tgacgagaaa aaacgtgcgg caagcgttaa agacgtatta | 420 |
| aacgctggct ggaacattaa aggcgttaaa cccggtacaa cagcttccga taacgttgat | 480 |
| ttcgtccgca cttacgacac agtcgagttc ttgagcgcag atacgaaaac aacgactgtt | 540 |
| aatgtggaaa gcaaagacaa cggcaagaaa accgaagtta aaatcggtgc gaagacttct | 600 |
| gttattaaag aaaagacgg taagttggtt actggtaaag acaaaggcga gaatggttct | 660 |
| tctacagacg aaggcgaagg cttagtgact gcaaagaag tgattgatgc agtaaacaag | 720 |
| gctggttgga gaatgaaaac aacaaccgct aatggtcaaa caggtcaagc tgacaagttt | 780 |
| gaaaccgtta catcaggcac aaatgtaacc tttgctagtg gtaaaggtac aactgcgact | 840 |
| gtaagtaaag atgatcaagg caacatcact gttatgtatg atgtaaatgt cggcgatgcc | 900 |
| ctaaacgtca atcagctgca aaacagcggt tggaatttgg attccaaagc ggttgcaggt | 960 |
| tcttcgggca aagtcatcag cggcaatgtt tcgccgagca agggaaagat ggatgaaacc | 1020 |
| gtcaacatta atgccggcaa caacatcgag attacccgca acggtaaaaa tatcgacatc | 1080 |
| gccacttcga tgaccccgca gttttccagc gtttcgctcg gcgcgggggc ggatgcgccc | 1140 |
| actttgagcg tggatgggga cgcattgaat gtcggcagca agaaggacaa caaacccgtc | 1200 |
| cgcattacca atgtcgcccc gggcgttaaa gagggggatg ttacaaacgt cgcacaactt | 1260 |
| aaaggcgtgg cgcaaaactt gaacaaccgc atcgacaatg tggacggcaa cgcgcgtgcg | 1320 |
| ggcatcgccc aagcgattgc aaccgcaggt ctggttcagg cgtatttgcc cggcaagagt | 1380 |
| atgatggcga tcggcggcgg cacttatcgc ggcgaagccg ttacgccat cggctactcc | 1440 |
| agtatttccg acggcggaaa ttggattatc aaaggcacgg cttccggcaa ttcgcgcggc | 1500 |
| catttcggtg cttccgcatc tgtcggttat cagtggtaa | 1539 |

<210> SEQ ID NO 29
<211> LENGTH: 1542
<212> TYPE: DNA
<213> ORGANISM: Neisseria meningitidis

<400> SEQUENCE: 29

| | |
|---|---|
| atgaacaaaa tataccgcat catttggaat agtgccctca atgcctgggt cgccgtatcc | 60 |
| gagctcacac gcaaccacac caaacgcgcc tccgcaaccg tgaagaccgc cgtattggcg | 120 |
| acactgttgt ttgcaacggt tcaggcgaat gctaccgatg aaacaggcct gatcaatgtt | 180 |
| gaaactgaaa aattatcgtt tggcgcaaac ggcaagaaag tcaacatcat aagcgacacc | 240 |
| aaaggcttga attttgcgaa agaaacggct gggacgaacg gcgacaccac ggttcatctg | 300 |
| aacggtatcg gttcgacttt gaccgatatg ctgctgaata ccggagcgac cacaaacgta | 360 |
| accaacgaca acgttaccga tgacgagaaa aaacgtgcgg caagcgttaa agacgtatta | 420 |
| aacgcaggct ggaacattaa aggcgttaaa cccggtacaa cagcttccga taacgttgat | 480 |
| ttcgtccgca cttacgacac agtcgagttc ttgagcgcag atacgaaaac aacgactgtt | 540 |
| aatgtggaaa gcaaagacaa cggcaagaaa accgaagtta aaatcggtgc gaagacttct | 600 |
| gttattaaag aaaagacgg taagttggtt actggtaaag gcaaaggcga gaatggttct | 660 |
| tctacagacg aaggcgaagg cttagtgact gcaaagaag tgattgatgc agtaaacaag | 720 |
| gctggttgga gaatgaaaac aacaaccgct aatggtcaaa caggtcaagc tgacaagttt | 780 |

```
gaaaccgtta catcaggcac aaaagtaacc tttgctagtg gtaatggtac aactgcgact    840
gtaagtaaag atgatcaagg caacatcact gttaagtatg atgtaaatgt cggcgatgcc    900
ctaaacgtca atcagctgca aaacagcggt tggaatttgg attccaaagc ggttgcaggt    960
tcttcgggca aagtcatcag cggcaatgtt tcgccgagca agggaaagat ggatgaaacc   1020
gtcaacatta atgccggcaa caacatcgag attacccgca acggcaaaaa tatcgacatc   1080
gccacttcga tgaccccgca attttccagc gtttcgctcg gcgcggggc ggatgcgccc    1140 actttaagcg tggatgacga gggcgcgttg aatgtcggca gcaaggatgc caacaaaccc   1200
gtccgcatta ccaatgtcgc cccgggcgtt aaagagggg atgttacaaa cgtcgcgcaa    1260
cttaaaggtg tggcgcaaaa cttgaacaac cgcatcgaca atgtgaacgg caacgcgcgt   1320
gcgggcatcg cccaagcgat tgcaaccgca ggtctggttc aggcgtatct gcccggcaag   1380
agtatgatgg cgatcggcgg cggcacttat ctcggcgaag ccggttatgc catcggctac   1440
tcaagcattt ccgccggcgg aaattggatt atcaaaggca cggcttccgg caattcgcgc   1500
ggccatttcg gtgcttccgc atctgtcggt tatcagtggt aa                      1542
```

```
<210> SEQ ID NO 30
<211> LENGTH: 1224
<212> TYPE: DNA
<213> ORGANISM: Neisseria meningitidis

<400> SEQUENCE: 30
atgaacaaaa ataccgcat catttggaat agtgccctca atgcatgggt cgtcgtatcc      60
gagctcacac gcaaccacac caaacgcgcc tccgcaaccg tgaagaccgc cgtattggcg    120
actctgttgt ttgcaacggt tcaggcaagt gctaacaacg ttgatttcgt ccgcacttac    180
gacacagtcg agttcttgag cgcagatacg aaaacaacga ctgttaatgt ggaaagcaaa    240
gacaacggca agaaaaccga agttaaaatc ggtgcgaaga cttctgttat taagaaaaaa    300
gacggtaagt tggttactgg taagacaaaa ggcgagaatg gttcttctac agacgaaggc    360
gaaggcttag tgactgcaaa agaagtgatt gatgcagtaa acaaggctgg ttggagaatg    420
aaaacaacaa ccgctaatgg tcaaacaggt caagctgaca gtttgaaac cgttacatca     480 ggcacaaatg taacctttgc tagtggtaaa ggtacaactg cgactgtaag taaagatgat    540
caaggcaaca tcactgttat gtatgatgta aatgtcggcg atgccctaaa cgtcaatcag    600
ctgcaaaaca gcggttggaa tttggattcc aaagcggttg caggttcttc gggcaaagtc    660
atcagcggca atgtttcgcc gagcaaggga agatggatg aaaccgtcaa cattaatgcc     720
ggcaacaaca tcgagattac ccgcaacggt aaaaatatcg acatcgccac ttcgatgacc    780
ccgcagtttt ccagcgtttc gctcggcgcg gggcggatg cgcccacttt gagcgtggat    840
ggggacgcat tgaatgtcgg cagcaagaag acaacaaac ccgtccgcat taccaatgtc     900
gccccgggcg ttaaagaggg ggatgttaca acgtcgcac aacttaaagg cgtggcgcaa    960
aacttgaaca accgcatcga caatgtggac ggcaacgcgc gtgcgggcat cgcccaagcg   1020
attgcaaccg caggtctggt tcaggcgtat ttgcccggca agagtatgat ggcgatcggc   1080
ggcggcactt atcgcggcga agccggttac gccatcggct actccagtat ttccgacggc   1140
ggaaattgga ttatcaaagg cacggcttcc ggcaattcgc gcggccattt cggtgcttcc   1200
gcatctgtcg gttatcagtg gtaa                                          1224
```

```
<210> SEQ ID NO 31
<211> LENGTH: 1302
<212> TYPE: DNA
```

<213> ORGANISM: Neisseria meningitidis

<400> SEQUENCE: 31

```
atgaacaaaa tataccgcat catttggaat agtgccctca atgcatgggt cgtcgtatcc    60
gagctcacac gcaaccacac caaacgcgcc tccgcaaccg tgaagaccgc cgtattggcg   120
actctgttgt ttgcaacggt tcaggcaagt gctaaccgtg cggcaagcgt taaagacgta   180
ttaaacgctg gctggaacat taaaggcgtt aaacccggta caacagcttc cgataacgtt   240
gatttcgtcc gcacttacga cacagtcgag ttcttgagcg cagatacgaa acaacgact   300
gttaatgtgg aaagcaaaga caacggcaag aaaaccgaag ttaaaatcgg tgcgaagact   360
tctgttatta agaaaaaga cggtaagttg gttactggta agacaaagg cgagaatggt    420
tcttctacag acgaaggcga aggcttagtg actgcaaaag aagtgattga tgcagtaaac   480
aaggctggtt ggagaatgaa aacaacaacc gctaatggtc aaacaggtca agctgacaag   540
tttgaaaccg ttacatcagg cacaaatgta acctttgcta gtggtaaagg tacaactgcg   600
actgtaagta aagatgatca aggcaacatc actgttatgt atgatgtaaa tgtcggcgat   660
gccctaaacg tcaatcagct gcaaaacagc ggttggaatt tggattccaa agcggttgca   720
ggttcttcgg gcaaagtcat cagcggcaat gtttcgccga gcaagggaaa gatggatgaa   780
accgtcaaca ttaatgccgg caacaacatc gagattaccc gcaacggtaa aaatatcgac   840
atcgccactt cgatgacccc gcagttttcc agcgtttcgc tcggcgcggg ggcggatgcg   900
cccactttga gcgtggatgg ggacgcattg aatgtcggca gcaagaagga caacaaaccc   960
gtccgcatta ccaatgtcgc cccgggcgtt aaagaggggg atgttacaaa cgtcgcacaa  1020
cttaaaggcg tggcgcaaaa cttgaacaac cgcatcgaca atgtggacgg caacgcgcgt  1080
gcgggcatcg cccaagcgat tgcaaccgca ggtctggttc aggcgtattt gcccggcaag  1140
agtatgatgg cgatcggcgg cggcacttat cgcggcgaag ccggttacgc catcggctac  1200
tccagtattt ccgacggcgg aaattggatt atcaaaggca cggcttccgg caattcgcgc  1260
ggccatttcg gtgcttccgc atctgtcggt tatcagtggt aa                    1302
```

<210> SEQ ID NO 32
<211> LENGTH: 1509
<212> TYPE: DNA
<213> ORGANISM: Neisseria meningitidis

<400> SEQUENCE: 32

```
atgaacaaaa tataccgcat catttggaat agtgccctca atgcatgggt cgtcgtatcc    60
gagctcacac gcaaccacac caaacgcgcc tccgcaaccg tgaagaccgc cgtattggcg   120
actctgttgt ttgcaacggt tcaggcaagt gctaacaccc tcaaagccgg cgacaacctg   180
aaaatcaaac aattcaccta ctcgctgaaa aaagacctca cagatctgac cagtgttgga   240
actgaaaaat tatcgtttag cgcaaacggc aataaagtca acatcacaag cgacaccaaa   300
ggcttgaatt ttgcgaaaga aacggctggg acgaacggcg acaccacggt tcatctgaac   360
ggtattggtt cgactttgac cgatcgtgcg gcaagcgtta agacgtatt aaacgctggc   420
tggaacatta aaggcgttaa aaacgttgat ttcgtccgca cttacgacac agtcgagttc   480
ttgagcgcag atacgaaaac aacgactgtt aatgtggaaa gcaagacaa cggcaagaaa   540
accgaagtta aaatcggtgc gaagacttct gttattaaag aaaaagacgg taagttggtt   600
actggtaaag acaaaggcga gaatggttct tctacagacg aaggcgaagg cttagtgact   660
gcaaaagaag tgattgatgc agtaaacaag gctggttgga gaatgaaaac aacaaccgct   720
```

-continued

```
aatggtcaaa caggtcaagc tgacaagttt gaaaccgtta catcaggcac aaatgtaacc    780
tttgctagtg gtaaaggtac aactgcgact gtaagtaaag atgatcaagg caacatcact    840
gttatgtatg atgtaaatgt cggcgatgcc ctaaacgtca atcagctgca aaacagcggt    900
tggaatttgg attccaaagc ggttgcaggt tcttcgggca aagtcatcag cggcaatgtt    960
tcgccgagca agggaaagat ggatgaaacc gtcaacatta atgccggcaa caacatcgag   1020
attacccgca acggtaaaaa tatcgacatc gccacttcga tgaccccgca gttttccagc   1080
gtttcgctcg gcgcggggc ggatgcgccc actttgagcg tggatgggga cgcattgaat   1140
gtcggcagca agaaggacaa caaacccgtc cgcattacca atgtcgcccc gggcgttaaa   1200
gagggggatg ttacaaacgt cgcacaactt aaaggcgtgg cgcaaaactt gaacaaccgc   1260
atcgacaatg tggacggcaa cgcgcgtgcg ggcatcgccc aagcgattgc aaccgcaggt   1320
ctggttcagg cgtatttgcc cggcaagagt atgatggcga tcggcggcgg cacttatcgc   1380
ggcgaagccg gttacgccat cggctactcc agtatttccg acggcggaaa ttggattatc   1440
aaaggcacgg cttccggcaa ttcgcgcggc catttcggtg cttccgcatc tgtcggttat   1500
cagtggtaa                                                           1509
```

<210> SEQ ID NO 33
<211> LENGTH: 540
<212> TYPE: PRT
<213> ORGANISM: Neisseria meningitidis

<400> SEQUENCE: 33

```
Asn Asn Glu Glu Gln Glu Glu Tyr Leu Tyr Leu His Pro Val Gln Arg
1               5                   10                  15

Thr Val Ala Val Leu Ile Val Asn Ser Asp Lys Glu Gly Ala Gly Glu
            20                  25                  30

Lys Glu Lys Val Glu Glu Asn Ser Asp Trp Ala Val Tyr Phe Asn Glu
        35                  40                  45

Lys Gly Val Leu Thr Ala Arg Glu Ile Thr Leu Lys Ala Gly Asp Asn
    50                  55                  60

Leu Lys Ile Lys Gln Asn Gly Thr Asn Phe Thr Tyr Ser Leu Lys Lys
65                  70                  75                  80

Asp Leu Thr Asp Leu Thr Ser Val Gly Thr Glu Lys Leu Ser Phe Ser
                85                  90                  95

Ala His Gly Asn Lys Val Asn Ile Thr Ser Asp Thr Lys Gly Leu Asn
            100                 105                 110

Phe Ala Lys Glu Thr Ala Gly Thr Asn Gly Asp Thr Thr Val His Leu
        115                 120                 125

Asn Gly Ile Gly Ser Thr Leu Thr Asp Thr Leu Leu Asn Thr Gly Ala
    130                 135                 140

Thr Thr Asn Val Thr Asn Asp Asn Val Thr Asp Asp Glu Lys Lys Arg
145                 150                 155                 160

Ala Ala Ser Val Lys Asp Val Leu Asn Ala Gly Trp Asn Ile Lys Gly
                165                 170                 175

Val Lys Pro Gly Thr Thr Ala Ser Asp Asn Val Asp Phe Val Arg Thr
            180                 185                 190

Tyr Asp Thr Val Glu Phe Leu Ser Ala Asp Thr Lys Thr Thr Thr Val
        195                 200                 205

Asn Val Glu Ser Lys Asp Asn Gly Lys Lys Thr Glu Val Lys Ile Gly
    210                 215                 220

Ala Lys Thr Ser Val Ile Lys Glu Lys Asp Gly Lys Leu Val Thr Gly
225                 230                 235                 240
```

Lys Asp Lys Gly Glu Asn Gly Ser Ser Thr Asp Glu Gly Gly Leu
                245                 250                 255

Val Thr Ala Lys Glu Val Ile Asp Ala Val Asn Lys Ala Gly Trp Arg
            260                 265                 270

Met Lys Thr Thr Thr Ala Asn Gly Gln Thr Gly Gln Ala Asp Lys Phe
            275                 280                 285

Glu Thr Val Thr Ser Gly Thr Asn Val Thr Phe Ala Ser Gly Lys Gly
            290                 295                 300

Thr Thr Ala Thr Val Ser Lys Asp Asp Gln Gly Asn Ile Thr Val Met
305                 310                 315                 320

Tyr Asp Val Asn Val Gly Asp Ala Leu Asn Val Asn Gln Leu Gln Asn
                325                 330                 335

Ser Gly Trp Asn Leu Asp Ser Lys Ala Val Ala Gly Ser Ser Gly Lys
                340                 345                 350

Val Ile Ser Gly Asn Val Ser Pro Ser Lys Lys Met Asp Glu Thr
                355                 360                 365

Val Asn Ile Asn Ala Gly Asn Asn Ile Glu Ile Thr Arg Asn Gly Lys
                370                 375                 380

Asn Ile Asp Ile Ala Thr Ser Met Thr Pro Gln Phe Ser Ser Val Ser
385                 390                 395                 400

Leu Gly Ala Gly Ala Asp Ala Pro Thr Leu Ser Val Asp Gly Asp Ala
                405                 410                 415

Leu Asn Val Gly Ser Lys Lys Asp Asn Lys Pro Val Arg Ile Thr Asn
                420                 425                 430

Val Ala Pro Gly Val Lys Glu Gly Asp Val Thr Asn Val Ala Gln Leu
                435                 440                 445

Lys Gly Val Ala Gln Asn Leu Asn Asn Arg Ile Asp Asn Val Asp Gly
                450                 455                 460

Asn Ala Arg Ala Gly Ile Ala Gln Ala Ile Ala Thr Ala Gly Leu Val
465                 470                 475                 480

Gln Ala Tyr Leu Pro Gly Lys Ser Met Met Ala Ile Gly Gly Gly Thr
                485                 490                 495

Tyr Arg Gly Glu Ala Gly Tyr Ala Ile Gly Tyr Ser Ser Ile Ser Asp
                500                 505                 510

Gly Gly Asn Trp Ile Ile Lys Gly Thr Ala Ser Gly Asn Ser Arg Gly
                515                 520                 525

His Phe Gly Ala Ser Ala Ser Val Gly Tyr Gln Trp
                530                 535                 540

<210> SEQ ID NO 34
<211> LENGTH: 541
<212> TYPE: PRT
<213> ORGANISM: Neisseria meningitidis

<400> SEQUENCE: 34

Thr Asp Glu Asp Glu Glu Glu Leu Glu Ser Val Gln Arg Ser Val
1               5                   10                  15

Val Gly Ser Ile Gln Ala Ser Met Glu Gly Ser Val Glu Leu Glu Thr
            20                  25                  30

Ile Ser Leu Ser Met Thr Asn Asp Ser Lys Glu Phe Val Asp Pro Tyr
            35                  40                  45

Ile Val Val Thr Leu Lys Ala Gly Asp Asn Leu Lys Ile Lys Gln Asn
            50                  55                  60

Thr Asn Glu Asn Thr Asn Ala Ser Ser Phe Thr Tyr Ser Leu Lys Lys
65                  70                  75                  80

```
Asp Leu Thr Gly Leu Ile Asn Val Glu Thr Glu Lys Leu Ser Phe Gly
                85                  90                  95

Ala Asn Gly Lys Lys Val Asn Ile Ile Ser Asp Thr Lys Gly Leu Asn
            100                 105                 110

Phe Ala Lys Glu Thr Ala Gly Thr Asn Gly Asp Thr Thr Val His Leu
        115                 120                 125

Asn Gly Ile Gly Ser Thr Leu Thr Asp Met Leu Leu Asn Thr Gly Ala
    130                 135                 140

Thr Thr Asn Val Thr Asn Asp Asn Val Thr Asp Asp Glu Lys Lys Arg
145                 150                 155                 160

Ala Ala Ser Val Lys Asp Val Leu Asn Ala Gly Trp Asn Ile Lys Gly
                165                 170                 175

Val Lys Pro Gly Thr Thr Ala Ser Asp Asn Val Asp Phe Val Arg Thr
            180                 185                 190

Tyr Asp Thr Val Glu Phe Leu Ser Ala Asp Thr Lys Thr Thr Thr Val
        195                 200                 205

Asn Val Glu Ser Lys Asp Asn Gly Lys Lys Thr Glu Val Lys Ile Gly
    210                 215                 220

Ala Lys Thr Ser Val Ile Lys Glu Lys Asp Gly Lys Leu Val Thr Gly
225                 230                 235                 240

Lys Gly Lys Gly Glu Asn Gly Ser Ser Thr Asp Glu Gly Gly Leu
                245                 250                 255

Val Thr Ala Lys Glu Val Ile Asp Ala Val Asn Lys Ala Gly Trp Arg
        260                 265                 270

Met Lys Thr Thr Thr Ala Asn Gly Gln Thr Gly Gln Ala Asp Lys Phe
    275                 280                 285

Glu Thr Val Thr Ser Gly Thr Lys Val Thr Phe Ala Ser Gly Asn Gly
290                 295                 300

Thr Thr Ala Thr Val Ser Lys Asp Asp Gln Gly Asn Ile Thr Val Lys
305                 310                 315                 320

Tyr Asp Val Asn Val Gly Asp Ala Leu Asn Val Asn Gln Leu Gln Asn
                325                 330                 335

Ser Gly Trp Asn Leu Asp Ser Lys Ala Val Ala Gly Ser Ser Gly Lys
            340                 345                 350

Val Ile Ser Gly Asn Val Ser Pro Ser Lys Gly Lys Met Asp Glu Thr
        355                 360                 365

Val Asn Ile Asn Ala Gly Asn Asn Ile Glu Ile Thr Arg Asn Gly Lys
    370                 375                 380

Asn Ile Asp Ile Ala Thr Ser Met Thr Pro Gln Phe Ser Ser Val Ser
385                 390                 395                 400

Leu Gly Ala Gly Ala Asp Ala Pro Thr Leu Ser Val Asp Glu Gly
                405                 410                 415

Ala Leu Asn Val Gly Ser Lys Asp Ala Asn Lys Pro Val Arg Ile Thr
            420                 425                 430

Asn Val Ala Pro Gly Val Lys Glu Gly Asp Val Thr Asn Val Ala Gln
        435                 440                 445

Leu Lys Gly Val Ala Gln Asn Leu Asn Asn Arg Ile Asp Asn Val Asn
    450                 455                 460

Gly Asn Ala Arg Ala Gly Ile Ala Gln Ala Ile Ala Thr Ala Gly Leu
465                 470                 475                 480

Val Gln Ala Tyr Leu Pro Gly Lys Ser Met Met Ala Ile Gly Gly Gly
                485                 490                 495

Thr Tyr Leu Gly Glu Ala Gly Tyr Ala Ile Gly Tyr Ser Ser Ile Ser
```

```
                500             505             510
Ala Gly Gly Asn Trp Ile Ile Lys Gly Thr Ala Ser Gly Asn Ser Arg
        515                 520                 525

Gly His Phe Gly Ala Ser Ala Ser Val Gly Tyr Gln Trp
        530                 535             540

<210> SEQ ID NO 35
<211> LENGTH: 461
<212> TYPE: PRT
<213> ORGANISM: Neisseria meningitidis

<400> SEQUENCE: 35

Asn Asn Glu Thr Asp Leu Thr Ser Val Gly Thr Glu Lys Leu Ser Phe
1               5                   10                  15

Ser Ala Asn Gly Asn Lys Val Asn Ile Thr Ser Asp Thr Lys Gly Leu
            20                  25                  30

Asn Phe Ala Lys Glu Thr Ala Gly Thr Asn Gly Asp Thr Thr Val His
        35                  40                  45

Leu Asn Gly Ile Gly Ser Thr Leu Thr Asp Thr Leu Asn Thr Gly
    50                  55                  60

Ala Thr Thr Asn Val Thr Asn Asp Asn Val Thr Asp Asp Glu Lys Lys
65                  70                  75                  80

Arg Ala Ala Ser Val Lys Asp Val Leu Asn Ala Gly Trp Asn Ile Lys
                85                  90                  95

Gly Val Lys Pro Gly Thr Thr Ala Ser Asp Asn Val Asp Phe Val Arg
            100                 105                 110

Thr Tyr Asp Thr Val Glu Phe Leu Ser Ala Asp Thr Lys Thr Thr Thr
        115                 120                 125

Val Asn Val Glu Ser Lys Asp Asn Gly Lys Lys Thr Glu Val Lys Ile
    130                 135                 140

Gly Ala Lys Thr Ser Val Ile Lys Glu Lys Asp Gly Lys Leu Val Thr
145                 150                 155                 160

Gly Lys Asp Lys Gly Glu Asn Gly Ser Thr Asp Glu Gly Glu Gly
                165                 170                 175

Leu Val Thr Ala Lys Glu Val Ile Asp Ala Val Asn Lys Ala Gly Trp
            180                 185                 190

Arg Met Lys Thr Thr Ala Asn Gly Gln Thr Gly Gln Ala Asp Lys
        195                 200                 205

Phe Glu Thr Val Thr Ser Gly Thr Asn Val Thr Phe Ala Ser Gly Lys
    210                 215                 220

Gly Thr Thr Ala Thr Val Ser Lys Asp Asp Gln Gly Asn Ile Thr Val
225                 230                 235                 240

Met Tyr Asp Val Asn Val Gly Asp Ala Leu Asn Val Asn Gln Leu Gln
                245                 250                 255

Asn Ser Gly Trp Asn Leu Asp Ser Lys Ala Val Ala Gly Ser Ser Gly
            260                 265                 270

Lys Val Ile Ser Gly Asn Val Ser Pro Ser Lys Gly Lys Met Asp Glu
        275                 280                 285

Thr Val Asn Ile Asn Ala Gly Asn Asn Ile Glu Ile Thr Arg Asn Gly
    290                 295                 300

Lys Asn Ile Asp Ile Ala Thr Ser Met Thr Pro Gln Phe Ser Ser Val
305                 310                 315                 320

Ser Leu Gly Ala Gly Ala Asp Ala Pro Thr Leu Ser Val Asp Gly Asp
                325                 330                 335

Ala Leu Asn Val Gly Ser Lys Lys Asp Asn Lys Pro Val Arg Ile Thr
```

```
                   340                 345                 350
Asn Val Ala Pro Gly Val Lys Glu Gly Asp Val Thr Asn Val Ala Gln
            355                 360                 365

Leu Lys Gly Val Ala Gln Asn Leu Asn Asn Arg Ile Asp Asn Val Asp
        370                 375                 380

Gly Asn Ala Arg Ala Gly Ile Ala Gln Ala Ile Ala Thr Ala Gly Leu
385                 390                 395                 400

Val Gln Ala Tyr Leu Pro Gly Lys Ser Met Met Ala Ile Gly Gly Gly
                405                 410                 415

Thr Tyr Arg Gly Glu Ala Gly Tyr Ala Ile Gly Tyr Ser Ser Ile Ser
            420                 425                 430

Asp Gly Gly Asn Trp Ile Ile Lys Gly Thr Ala Ser Gly Asn Ser Arg
        435                 440                 445

Gly His Phe Gly Ala Ser Ala Ser Val Gly Tyr Gln Trp
    450                 455                 460

<210> SEQ ID NO 36
<211> LENGTH: 462
<212> TYPE: PRT
<213> ORGANISM: Neisseria meningitidis

<400> SEQUENCE: 36

Thr Asp Glu Thr Gly Leu Ile Asn Val Glu Thr Glu Lys Leu Ser Phe
1               5                   10                  15

Gly Ala Asn Gly Lys Lys Val Asn Ile Ile Ser Asp Thr Lys Gly Leu
            20                  25                  30

Asn Phe Ala Lys Glu Thr Ala Gly Thr Asn Gly Asp Thr Thr Val His
        35                  40                  45

Leu Asn Gly Ile Gly Ser Thr Leu Thr Asp Met Leu Leu Asn Thr Gly
    50                  55                  60

Ala Thr Thr Asn Val Thr Asn Asp Asn Val Thr Asp Glu Lys Lys
65                  70                  75                  80

Arg Ala Ala Ser Val Lys Asp Val Leu Asn Ala Gly Trp Asn Ile Lys
                85                  90                  95

Gly Val Lys Pro Gly Thr Thr Ala Ser Asp Asn Val Asp Phe Val Arg
            100                 105                 110

Thr Tyr Asp Thr Val Glu Phe Leu Ser Ala Asp Thr Lys Thr Thr Thr
        115                 120                 125

Val Asn Val Glu Ser Lys Asp Asn Gly Lys Lys Thr Glu Val Lys Ile
    130                 135                 140

Gly Ala Lys Thr Ser Val Ile Lys Glu Lys Asp Gly Lys Leu Val Thr
145                 150                 155                 160

Gly Lys Gly Lys Gly Glu Asn Gly Ser Ser Thr Asp Glu Gly Glu Gly
                165                 170                 175

Leu Val Thr Ala Lys Glu Val Ile Asp Ala Val Asn Lys Ala Gly Trp
            180                 185                 190

Arg Met Lys Thr Thr Thr Ala Asn Gly Gln Thr Gly Gln Ala Asp Lys
        195                 200                 205

Phe Glu Thr Val Thr Ser Gly Thr Lys Val Thr Phe Ala Ser Gly Asn
    210                 215                 220

Gly Thr Thr Ala Thr Val Ser Lys Asp Gln Gly Asn Ile Thr Val
225                 230                 235                 240

Lys Tyr Asp Val Asn Val Gly Asp Ala Leu Asn Val Asn Gln Leu Gln
                245                 250                 255

Asn Ser Gly Trp Asn Leu Asp Ser Lys Ala Val Ala Gly Ser Ser Gly
```

```
                    260                 265                 270
Lys Val Ile Ser Gly Asn Val Ser Pro Ser Lys Gly Lys Met Asp Glu
                275                 280                 285

Thr Val Asn Ile Asn Ala Gly Asn Asn Ile Glu Ile Thr Arg Asn Gly
                290                 295                 300

Lys Asn Ile Asp Ile Ala Thr Ser Met Thr Pro Gln Phe Ser Ser Val
305                 310                 315                 320

Ser Leu Gly Ala Gly Ala Asp Ala Pro Thr Leu Ser Val Asp Asp Glu
                325                 330                 335

Gly Ala Leu Asn Val Gly Ser Lys Asp Ala Asn Lys Pro Val Arg Ile
                340                 345                 350

Thr Asn Val Ala Pro Gly Val Lys Glu Gly Asp Val Thr Asn Val Ala
                355                 360                 365

Gln Leu Lys Gly Val Ala Gln Asn Leu Asn Asn Arg Ile Asp Asn Val
                370                 375                 380

Asn Gly Asn Ala Arg Ala Gly Ile Ala Gln Ala Ile Ala Thr Ala Gly
385                 390                 395                 400

Leu Val Gln Ala Tyr Leu Pro Gly Lys Ser Met Met Ala Ile Gly Gly
                405                 410                 415

Gly Thr Tyr Leu Gly Glu Ala Gly Tyr Ala Ile Gly Tyr Ser Ser Ile
                420                 425                 430

Ser Ala Gly Gly Asn Trp Ile Ile Lys Gly Thr Ala Ser Gly Asn Ser
                435                 440                 445

Arg Gly His Phe Gly Ala Ser Ala Ser Val Gly Tyr Gln Trp
                450                 455                 460

<210> SEQ ID NO 37
<211> LENGTH: 356
<212> TYPE: PRT
<213> ORGANISM: Neisseria meningitidis

<400> SEQUENCE: 37

Asn Asn Val Asp Phe Val Arg Thr Tyr Asp Thr Val Glu Phe Leu Ser
1               5                   10                  15

Ala Asp Thr Lys Thr Thr Thr Val Asn Val Glu Ser Lys Asp Asn Gly
                20                  25                  30

Lys Lys Thr Glu Val Lys Ile Gly Ala Lys Thr Ser Val Ile Lys Glu
                35                  40                  45

Lys Asp Gly Lys Leu Val Thr Gly Lys Asp Lys Gly Glu Asn Gly Ser
                50                  55                  60

Ser Thr Asp Glu Gly Glu Gly Leu Val Thr Ala Lys Glu Val Ile Asp
65                  70                  75                  80

Ala Val Asn Lys Ala Gly Trp Arg Met Lys Thr Thr Thr Ala Asn Gly
                85                  90                  95

Gln Thr Gly Gln Ala Asp Lys Phe Glu Thr Val Thr Ser Gly Thr Asn
                100                 105                 110

Val Thr Phe Ala Ser Gly Lys Gly Thr Thr Ala Thr Val Ser Lys Asp
                115                 120                 125

Asp Gln Gly Asn Ile Thr Val Met Tyr Asp Val Asn Val Gly Asp Ala
                130                 135                 140

Leu Asn Val Asn Gln Leu Gln Asn Ser Gly Trp Asn Leu Asp Ser Lys
145                 150                 155                 160

Ala Val Ala Gly Ser Ser Gly Lys Val Ile Ser Gly Asn Val Ser Pro
                165                 170                 175

Ser Lys Gly Lys Met Asp Glu Thr Val Asn Ile Asn Ala Gly Asn Asn
```

-continued

```
                180                 185                 190
Ile Glu Ile Thr Arg Asn Gly Lys Asn Ile Asp Ile Ala Thr Ser Met
            195                 200                 205

Thr Pro Gln Phe Ser Ser Val Ser Leu Gly Ala Gly Ala Asp Ala Pro
        210                 215                 220

Thr Leu Ser Val Asp Gly Asp Ala Leu Asn Val Gly Ser Lys Lys Asp
225                 230                 235                 240

Asn Lys Pro Val Arg Ile Thr Asn Val Ala Pro Gly Val Lys Glu Gly
                245                 250                 255

Asp Val Thr Asn Val Ala Gln Leu Lys Gly Val Ala Gln Asn Leu Asn
            260                 265                 270

Asn Arg Ile Asp Asn Val Asp Gly Asn Ala Arg Ala Gly Ile Ala Gln
        275                 280                 285

Ala Ile Ala Thr Ala Gly Leu Val Gln Ala Tyr Leu Pro Gly Lys Ser
    290                 295                 300

Met Met Ala Ile Gly Gly Gly Thr Tyr Arg Gly Glu Ala Gly Tyr Ala
305                 310                 315                 320

Ile Gly Tyr Ser Ser Ile Ser Asp Gly Gly Asn Trp Ile Ile Lys Gly
                325                 330                 335

Thr Ala Ser Gly Asn Ser Arg Gly His Phe Gly Ala Ser Ala Ser Val
            340                 345                 350

Gly Tyr Gln Trp
        355

<210> SEQ ID NO 38
<211> LENGTH: 382
<212> TYPE: PRT
<213> ORGANISM: Neisseria meningitidis

<400> SEQUENCE: 38

Asn Arg Ala Ala Ser Val Lys Asp Val Leu Asn Ala Gly Trp Asn Ile
1               5                   10                  15

Lys Gly Val Lys Pro Gly Thr Thr Ala Ser Asp Asn Val Asp Phe Val
            20                  25                  30

Arg Thr Tyr Asp Thr Val Glu Phe Leu Ser Ala Asp Thr Lys Thr Thr
        35                  40                  45

Thr Val Asn Val Glu Ser Lys Asp Asn Gly Lys Lys Thr Glu Val Lys
    50                  55                  60

Ile Gly Ala Lys Thr Ser Val Ile Lys Glu Lys Asp Gly Lys Leu Val
65                  70                  75                  80

Thr Gly Lys Asp Lys Gly Glu Asn Gly Ser Ser Thr Asp Glu Gly Glu
                85                  90                  95

Gly Leu Val Thr Ala Lys Glu Val Ile Asp Ala Val Asn Lys Ala Gly
            100                 105                 110

Trp Arg Met Lys Thr Thr Thr Ala Asn Gly Gln Thr Gly Gln Ala Asp
        115                 120                 125

Lys Phe Glu Thr Val Thr Ser Gly Thr Asn Val Thr Phe Ala Ser Gly
    130                 135                 140

Lys Gly Thr Thr Ala Thr Val Ser Lys Asp Asp Gln Gly Asn Ile Thr
145                 150                 155                 160

Val Met Tyr Asp Val Asn Val Gly Asp Ala Leu Asn Val Asn Gln Leu
                165                 170                 175

Gln Asn Ser Gly Trp Asn Leu Asp Ser Lys Ala Val Ala Gly Ser Ser
            180                 185                 190

Gly Lys Val Ile Ser Gly Asn Val Ser Pro Ser Lys Gly Lys Met Asp
```

```
                 195                 200                 205
Glu Thr Val Asn Ile Asn Ala Gly Asn Asn Ile Glu Ile Thr Arg Asn
210                 215                 220

Gly Lys Asn Ile Asp Ile Ala Thr Ser Met Thr Pro Gln Phe Ser Ser
225                 230                 235                 240

Val Ser Leu Gly Ala Gly Ala Asp Ala Pro Thr Leu Ser Val Asp Gly
                245                 250                 255

Asp Ala Leu Asn Val Gly Ser Lys Lys Asp Asn Lys Pro Val Arg Ile
                260                 265                 270

Thr Asn Val Ala Pro Gly Val Lys Glu Gly Asp Val Thr Asn Val Ala
                275                 280                 285

Gln Leu Lys Gly Val Ala Gln Asn Leu Asn Asn Arg Ile Asp Asn Val
                290                 295                 300

Asp Gly Asn Ala Arg Ala Gly Ile Ala Gln Ala Ile Ala Thr Ala Gly
305                 310                 315                 320

Leu Val Gln Ala Tyr Leu Pro Gly Lys Ser Met Met Ala Ile Gly Gly
                325                 330                 335

Gly Thr Tyr Arg Gly Glu Ala Gly Tyr Ala Ile Gly Tyr Ser Ser Ile
                340                 345                 350

Ser Asp Gly Gly Asn Trp Ile Ile Lys Gly Thr Ala Ser Gly Asn Ser
                355                 360                 365

Arg Gly His Phe Gly Ala Ser Ala Ser Val Gly Tyr Gln Trp
                370                 375                 380

<210> SEQ ID NO 39
<211> LENGTH: 201
<212> TYPE: PRT
<213> ORGANISM: Neisseria meningitidis

<400> SEQUENCE: 39

Ser Ala Asn Thr Leu Lys Ala Gly Asp Asn Leu Lys Ile Lys Gln Phe
1               5                   10                  15

Thr Tyr Ser Leu Lys Lys Asp Leu Thr Asp Leu Thr Ser Val Gly Thr
                20                  25                  30

Glu Lys Leu Ser Phe Ser Ala Asn Gly Asn Lys Val Asn Ile Thr Ser
                35                  40                  45

Asp Thr Lys Gly Leu Asn Phe Ala Lys Glu Thr Ala Gly Thr Asn Gly
50                  55                  60

Asp Thr Thr Val His Leu Asn Gly Ile Gly Ser Thr Leu Thr Asp Arg
65                  70                  75                  80

Ala Ala Ser Val Lys Asp Val Leu Asn Ala Gly Trp Asn Ile Lys Gly
                85                  90                  95

Val Lys Asn Val Asp Phe Val Arg Thr Tyr Asp Thr Val Glu Phe Leu
                100                 105                 110

Ser Ala Asp Thr Lys Thr Thr Thr Val Asn Val Glu Ser Lys Asp Asn
                115                 120                 125

Gly Lys Lys Thr Glu Val Lys Ile Gly Ala Lys Thr Ser Val Ile Lys
                130                 135                 140

Glu Lys Asp Gly Lys Leu Val Thr Gly Lys Asp Lys Gly Glu Asn Gly
145                 150                 155                 160

Ser Ser Thr Asp Glu Gly Glu Gly Leu Val Thr Ala Lys Glu Val Ile
                165                 170                 175

Asp Ala Val Asn Lys Ala Gly Trp Arg Met Lys Thr Thr Thr Ala Asn
                180                 185                 190

Gly Gln Thr Gly Gln Ala Asp Lys Phe
```

```
<210> SEQ ID NO 40
<211> LENGTH: 51
<212> TYPE: DNA
<213> ORGANISM: Neisseria meningitidis

<400> SEQUENCE: 40
caattaacgg ccgaataaaa ggaagccgat atgaacaaaa tataccgcat c        51

<210> SEQ ID NO 41
<211> LENGTH: 31
<212> TYPE: DNA
<213> ORGANISM: Neisseria meningitidis

<400> SEQUENCE: 41
tggaatccat ggaatcgcca cccttcccctt c                              31

<210> SEQ ID NO 42
<211> LENGTH: 30
<212> TYPE: DNA
<213> ORGANISM: Neisseria meningitidis

<400> SEQUENCE: 42
ggtcagatct gtttcattgt tagcacttgc                                 30

<210> SEQ ID NO 43
<211> LENGTH: 30
<212> TYPE: DNA
<213> ORGANISM: Neisseria meningitidis

<400> SEQUENCE: 43
gatcaggcct gtatcttcat cggtagcatt                                 30

<210> SEQ ID NO 44
<211> LENGTH: 39
<212> TYPE: DNA
<213> ORGANISM: Neisseria meningitidis

<400> SEQUENCE: 44
gacgaaatca acgttcttag cacttgcctg aaccgttgc                       39

<210> SEQ ID NO 45
<211> LENGTH: 24
<212> TYPE: DNA
<213> ORGANISM: Neisseria meningitidis

<400> SEQUENCE: 45
aacgttgatt tcgtccgcac ttac                                       24

<210> SEQ ID NO 46
<211> LENGTH: 39
<212> TYPE: DNA
<213> ORGANISM: Neisseria meningitidis

<400> SEQUENCE: 46
aacgcttgcc gcacgcttag cacttgcctg caacgttgc                       39

<210> SEQ ID NO 47
<211> LENGTH: 24
<212> TYPE: DNA
<213> ORGANISM: Neisseria meningitidis

<400> SEQUENCE: 47
```

```
cgtgcggcaa gcgttaaaga cgta                                              24

<210> SEQ ID NO 48
<211> LENGTH: 72
<212> TYPE: DNA
<213> ORGANISM: Neisseria meningitidis

<400> SEQUENCE: 48
cagcgagtag gtgaattgtt tgattttcag gttgtcgccg gctttgaggg tgttagcact       60
tgcctgaacc gt                                                           72

<210> SEQ ID NO 49
<211> LENGTH: 24
<212> TYPE: DNA
<213> ORGANISM: Neisseria meningitidis

<400> SEQUENCE: 49
ttcacctact cgctgaaaaa agac                                              24

<210> SEQ ID NO 50
<211> LENGTH: 57
<212> TYPE: DNA
<213> ORGANISM: Neisseria meningitidis

<400> SEQUENCE: 50
gccagcgttt aatacgtctt taacgcttgc cgcacgatcg gtcaaagtcg aaccaat         57

<210> SEQ ID NO 51
<211> LENGTH: 57
<212> TYPE: DNA
<213> ORGANISM: Neisseria meningitidis

<400> SEQUENCE: 51
gtattaaacg ctggctggaa cattaaaggc gttaaaaacg ttgatttcgt ccgcact          57

<210> SEQ ID NO 52
<211> LENGTH: 11
<212> TYPE: PRT
<213> ORGANISM: Neisseria meningitidis
<220> FEATURE:
<221> NAME/KEY: misc_feature
<223> OTHER INFORMATION: "X" is any amino acid or absent amino acid

<400> SEQUENCE: 52

Xaa Xaa Glu Thr Asp Leu Thr Ser Val Gly Thr
1               5                   10
```

MODIFIED SURFACE ANTIGEN

CROSS-REFERENCE TO RELATED APPLICATION

This application is entitled to priority, pursuant to 35 U.S.C. §119(e), to U.S. Provisional Application Ser. No. 60/177,917, filed Jan. 25, 2000.

FIELD OF THE INVENTION

THIS INVENTION relates to novel proteins that constitute modified forms of a *Neisseria meningitidis* surface antigen, to nucleic acids encoding such novel peptides and polypeptides, and to the use of these in diagnostics, in therapeutic and prophylactic vaccines and in the design and/or screening of medicaments. More particularly, by having deletions of non-conserved amino acids, the modified surface antigens of the invention may be useful in vaccines which effectively immunize against a broader spectrum of *N. meningitidis* strains than would be expected from a corresponding wild-type surface antigen.

BACKGROUND OF THE INVENTION

*Neisseria meningitidis* is a Gram-negative bacterium and the causative agent of meningococcal meningitis and septicemia. Its only known host is the human, and it may be carried asymptomatically by approximately 10% of the population (Caugant et al, 1994, Journal of Clinical Microbiology 32 323).

*N. meningitidis* may express a polysaccharide capsule, and this allows classification of the bacteria according to the nature of the capsule expressed. There are at least twelve serogroups of *N. meningitidis*: A, B, C, 29-E, H, I, K, L, W135, X, Y and Z, of which serogroups A, B, and C cause 90% of meningococcal disease (Poolman et al, 1995, Infectious Agents and Disease 4 13). Vaccines directed against serogroups A and C are available, but the serogroup B capsular polysaccharide is poorly immunogenic and does not induce protection in humans.

Other membrane and extracellular components are therefore being examined for their suitability for inclusion in vaccines. Examples include the outer membrane proteins of classes 1, 2 and 3 (porin; encoded by por genes), and classes 4 (Rmp) and 5 (Opacity proteins; encoded by opa and opc genes).

However, to date, none of these candidates is able to induce complete protection, particularly in children (Romero et al., 1994, Clinical Microbiology Review, 7 559; Poolman et al., 1995, supra).

To create an effective vaccine, it is necessary to identify components of *N. meningitidis* which are present in a majority of strains, and which are capable of inducing a protective immune response (for example, bactericidal antibodies).

In this regard, reference is made to International Publications WO 99/24578, WO99/36544, WO99/58683 and WO99/57280, each of which is incorporated herein by reference and describe a number of candidate proteins that may be useful in vaccines to immunize against *Neisseria meningitidis*.

In this regard, particular reference is made to International Publication WO99/31132 and Peak et al. 2000, FEMS Immunol. Med. Microbiol. 28 329, each of which is incorporated herein by reference and describe a novel surface antigen isolated from a number of different strains of *N. meningitidis*, which surface antigen, and allelic variants thereof, for the purposes of this specification will be referred to as NhhA.

SUMMARY OF THE INVENTION

The present inventors have discovered that the NhhA surface antigen has polypeptide regions which are variable between *N. meningitidis* strains, and other regions which are conserved between strains. The variable regions may be immunogenic and tend to elicit strain-specific immune responses, such that vaccines incorporating an NhhA antigen derived from a particular strain of *N. meningitidis* tend to preferentially immunize against that particular strain. As a result, the present inventors have sought to produce a modified NhhA polypeptide which elicts an immune response which is not as strain-specific as that elicited by wild-type NhhA. This modified NhhA antigen will be useful for the production of therapeutic and/or prophylactic vaccines against *N. meningitidis* as will be described hereinafter. By directing the immune response primarily against conserved epitopes, such vaccines should effectively immunize against a broader spectrum of *N. meningitidis* strains than would be expected following immunization with wild-type NhhA.

The present invention is therefore broadly directed to isolated proteins having conserved amino acids of NhhA polypeptides.

Proteins of the invention may therefore have one or more deletions of non-conserved amino acids compared to a corresponding wild-type NhhA polypeptide.

In a first aspect, the invention provides an isolated protein comprising twelve or more contiguous conserved amino acids sequences of an NhhA polypeptide, said isolated protein excluding wild-type NhhA polypeptides.

Suitably, the protein of the invention is capable of eliciting an immune response.

Preferably, the immune response is less strain-specific than that elicited by said corresponding wild-type NhhA polypeptide.

More preferably, said immune response provides protection against one or more strains of *N. meningitidis*, or even more preferably a plurality of strains of *N. meningitidis*

Wild-type NhhA polypeptide sequences are exemplified in FIG. 1 (SEQ ID NOS: 1 to 10).

A consensus amino acid sequence is also set forth in FIG. 1 (SEQ ID NO:11).

The isolated protein of the invention preferably comprises one or more constant regions of an NhhA polypeptide, herein designated C1, C2, C3, C4 and C5 regions in FIG. 1.

It will be appreciated that according to this aspect, suitably one or more non-conserved amino acids of a variable region of an NhhA polypeptide, designated as V1, V2, V3 or V4 regions in FIG. 1, are deleted with respect to a wild-type NhhA polypeptide.

Preferably, a V1 region, or at least a substantial portion thereof is deleted.

In particular embodiments, the isolated protein has an amino acid sequence as set forth in any one of FIGS. 5 to 9 (SEQ ID NOS: 23 to 27) which are examples of "modified NhhA polypeptides of the invention". In FIGS. 14A-14G (SEQ ID NOS: 33 to 39) further examples are provided of "mature" polypeptides predicted to result of removal of N-terminal signal sequences.

According to a second aspect, the invention provides an isolated nucleic acid encoding a polypeptide according to the first aspect.

Wild-type nhhA nucleic acid sequences are exemplified in FIG. 2 (SEQ ID NOS: 12 to 21).

A consensus nucleic acid sequence is also set forth in FIG. 2 (SEQ ID NO:22).

Preferably, the C1, C2, C3, C4 and C5 regions are encoded by respective nucleotide sequences as set forth in FIG. 2.

Preferably, the V1, V2, V3 and V4 regions are encoded by respective nucleotide sequences as set forth in FIG. 2.

In a particular embodiment, the isolated nucleic acid of the invention has a nucleotide sequence as set forth in any one of FIGS. 5 to 9 (SEQ ID NOS: 28 to 32), which are particular examples of "modified nhhA nucleic acids of the invention".

The invention according to the first and second aspects extends to homologs, fragments, variants and derivatives of the isolated proteins and nucleic acids of the invention.

Specifically excluded from the scope of the invention are wild-type NhhA polypeptides and nhhA nucleic acids.

In a third aspect, the invention resides in an expression construct comprising an expression vector and a nucleic acid according to the second aspect, wherein said sequence is operably lined to one or more regulatory nucleic acids in said expression vector.

In a fourth aspect, the invention provides a host cell containing an expression construct according to the third aspect.

In a fifth aspect of the invention, there is provided a method of producing a recombinant isolated protein according to the first aspect, said method comprising the steps of:
(1) culturing a host cell containing an expression vector according to the third aspect such that said polypeptide is expressed in said host cell; and
(ii) isolating said recombinant polypeptide.

In a sixth aspect, the invention provides an antibody or antibody fragment that binds to a protein of the invention, fragment, variant or derivative thereof.

In a seventh aspect, the invention provides a method of detecting N. meningitidis in a biological sample suspected of containing same, said method comprising the steps of:
(i) isolating the biological sample from an individual;
(ii) combining the above-mentioned antibody or antibody fragment with the biological sample; and
(iii) detecting specifically bound antibody or antibody fragment which indicates the presence of N. meningitidis.

In an eighth aspect, there is provided a method of detecting N. meningitidis bacteria in a biological sample suspected of containing said bacteria, said method comprising the steps of:
(i) isolating the biological sample from a patient;
(ii) detecting a nucleic acid sequence according to the second-mentioned aspect in said sample which indicates the presence of said bacteria.

In a ninth aspect, the invention provides a method for diagnosing infection of an individual by N. meningitidis, said method comprising the steps of:
(i) contacting a biological sample from an individual with a polypeptide, fragment, variant or derivative of the invention; and
(ii) determining the presence or absence of a complex between said polypeptide, fragment, variant or derivative and N. meningitidis-specific antibodies in said sample, wherein the presence of said complex is indicative of said infection.

Preferably, the individual is a mammal.

More preferably, the individual is a human.

In a tenth aspect, the invention also extends to the use of an isolated protein according to the first-mentioned aspect, the use of isolated nucleic acids according to the second aspect or the use of the antibody or antibody fragment mentioned above in a kit for detecting N. meningitidis bacteria in a biological sample.

In an eleventh aspect of the invention, there is provided a pharmaceutical composition comprising an isolated protein according to the first mentioned aspect.

Preferably, said pharmaceutical composition is a vaccine.

In a twelfth aspect, the invention provides a method of preventing infection of a patient by N. meningitidis, comprising the step of administrating a pharmaceutically effective amount of the above-mentioned vaccine.

In a thirteenth aspect, the invention provides a method of identifying an immunogenic fragment of an isolated protein, variant or derivative according to the first mentioned aspect, comprising the steps of:
(i) producing a fragment of said polypeptide, variant or derivative;
(ii) administering said fragment to an individual; and
(iii) detecting an immune response in said individual, which response includes production of elements which specifically bind N. meningitidis and/or said polypeptide, variant or derivative, and/or a protective effect against N. meningitidis infection.

Preferably, the individual is a mammal.

More preferably, the individual is a human.

BRIEF DESCRIPTION OF THE FIGURES AND TABLES

Table 1: Identification of amino acids of the conserved regions (C1, C2, C3, C4 and C5) and variable regions (V1, V2, V3 and V4) of an NhhA polypeptide from each of ten (10) indicated strains of N. meningitidis. Relevant SEQ ID NOS are also indicated. Column 1=strain designation. SEQ ID NOS: 1-9 were previously described in copending application WO99/31132; the sequences of NhhA and nhhA of strain Z2491 were obtained from the database of the Wellcome Trust/Sanger Institute genomic sequencing project for N. meningitidis; column 2=amino acid numbering of C1 region; column 3=amino acid numbering of V1 region; column 4=amino acid numbering of C2 region; column 5=amino acid numbering of V2 region; column 6=amino acid numbering of C3 region, column 7=amino acid numbering of V2 region; column 8=amino acid numbering of C4 region; column 9=amino acid numbering of V4 region; column 10=amino acid numbering of C5 region. Note that the amino acid numbering of the consensus sequence (SEQ ID NO: 11) is also indicated.

Table 2: Table of amino acid substitutions.

FIG. 1 (comprising FIGS. 1A-1E): Amino acid sequence alignments of NhhA polypeptide amino acid sequences from ten (10) N. meningitidis strains (SEQ ID NOS: 1-10) together with consensus sequence (SEQ ID NO: 11). Strain names and polypeptide sequences used in this alignment correspond to the strain names and SEQ ID NOS in column 1 of Table 1. Amino acids are indicated by standard single letter abbreviations. Consensus amino acids are shown only where residues are completely conserved. Conserved regions (double underlined, labeled C1, C2, C3, C4, C5) and variable regions (single underlined, labeled V1, V2, V3, V4) are indicated under the consensus sequence.

FIG. 2 (comprising FIGS. 2A-2H): Nucleotide sequence alignment of nhhA nucleic acids from ten (10) N. meningitidis strains, which sequences encode the amino acid sequences of FIG. 1. Regions C1, C2, C3, C4, C5 and V1, V2, V3, V4 are as described in FIG. 1 and Table 1.

Figure 3B:
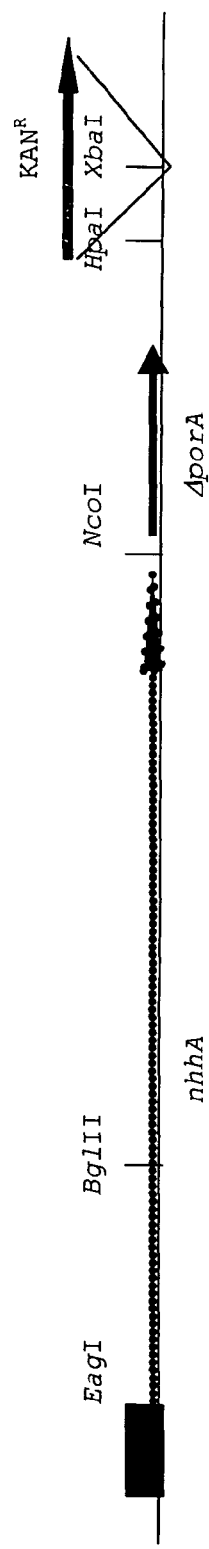

FIG. 3 (comprising FIGS. 3A and 3B): Plasmid map corresponding to pCO14K with a PCR amplification product encoding wild-type PMC21 NhhA operably linked to the porA promoter. (Not indicate the arrangement of the porA and kanR genes in pCO14K. Oligonucleotide primers HOMP5' and HOMP3'AN used to amplify the nhhA gene of strain PMC21 are shown. The nhhA gene is shown by dotted arrow, the porA promoter by a black box, and EagI and NcoI restriction sites used to replace porA with nhhA in as described in Example 2 are shown. FIG. 3B Arrangement of genes in pIP52(PMC21), as described in Example 2. The BglII site used to construct a mutant as described in Example 4 is shown.

Figure 4A:
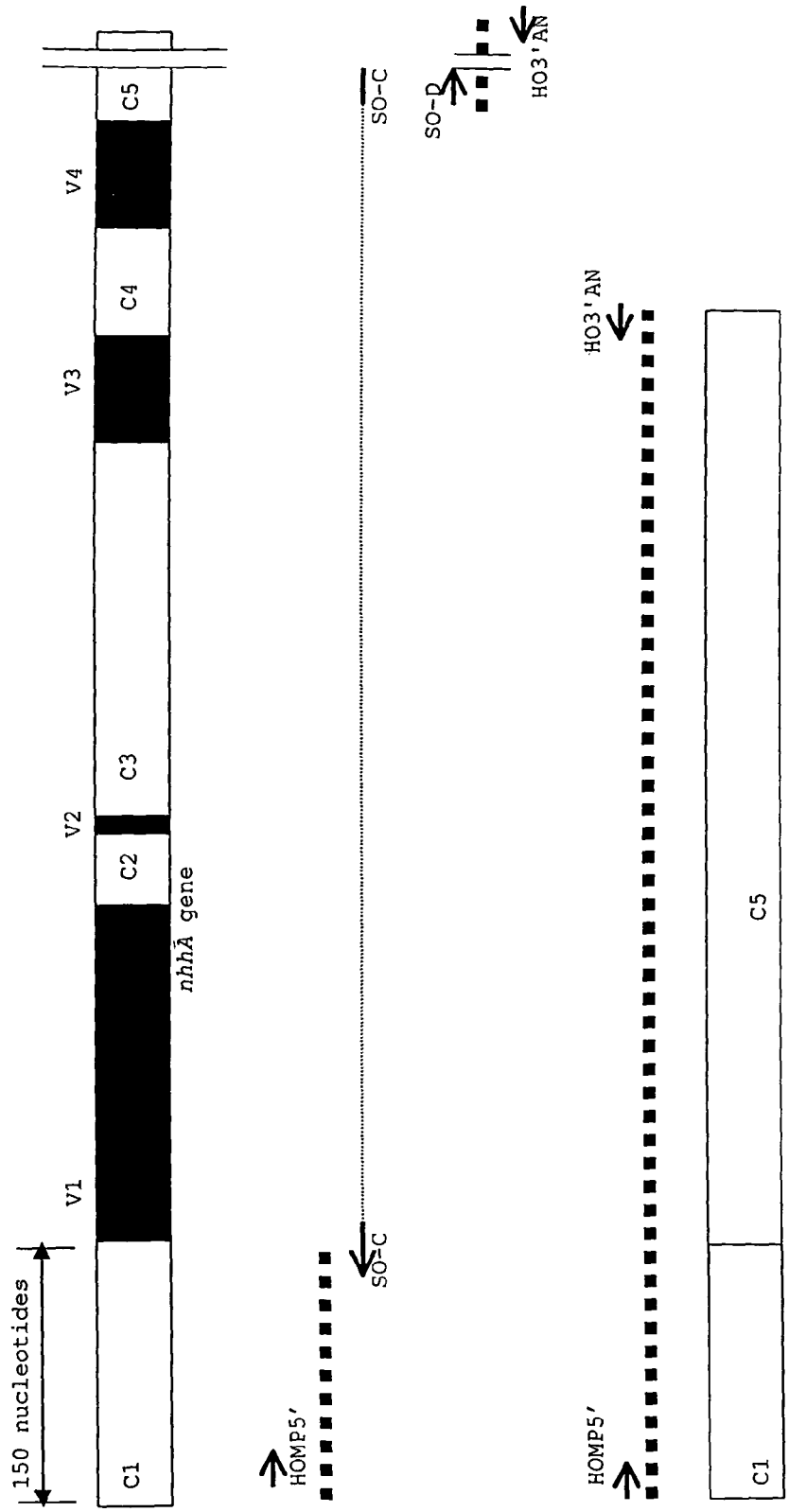
Figure 4B:
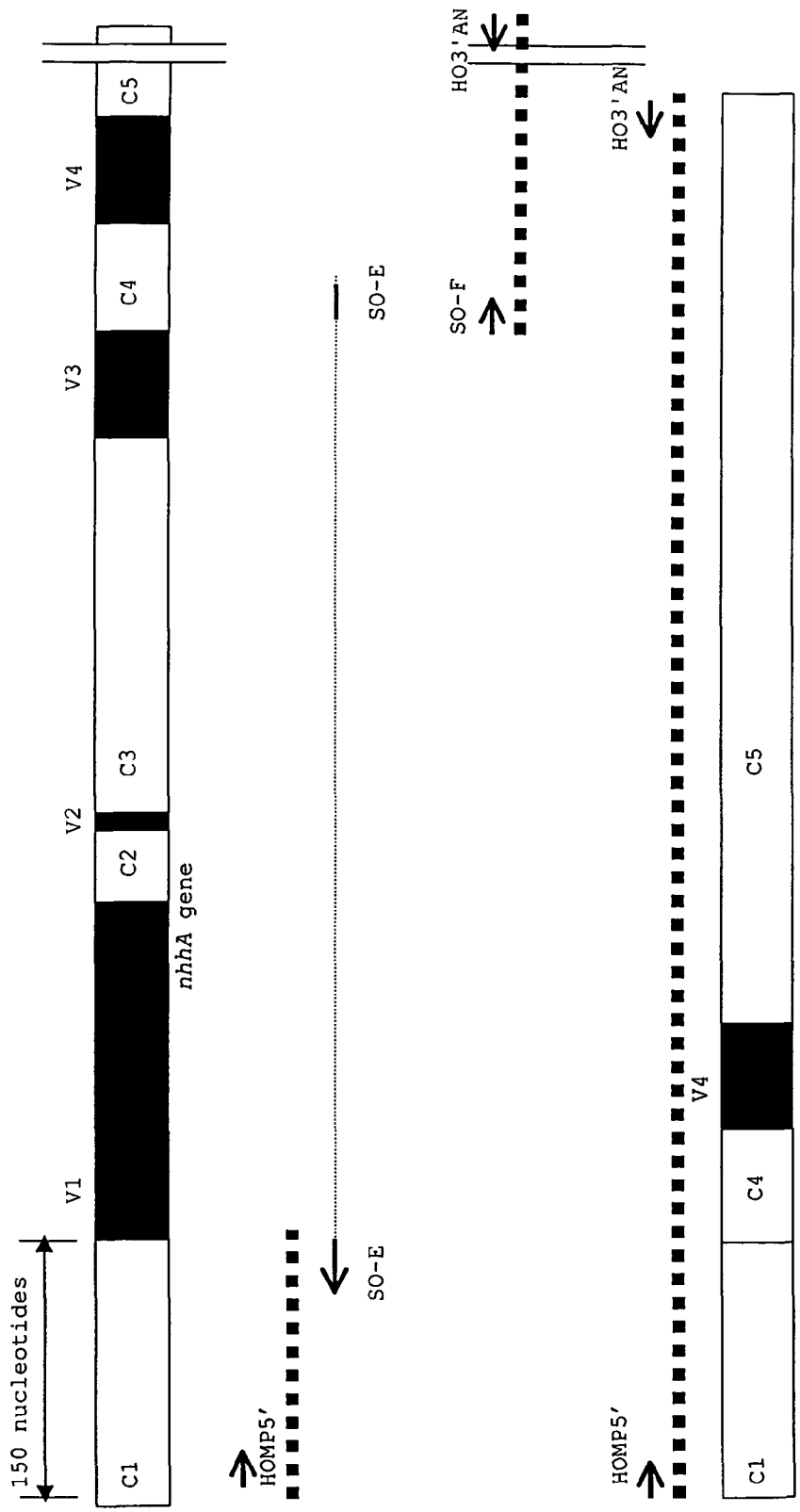
Figure 4C:
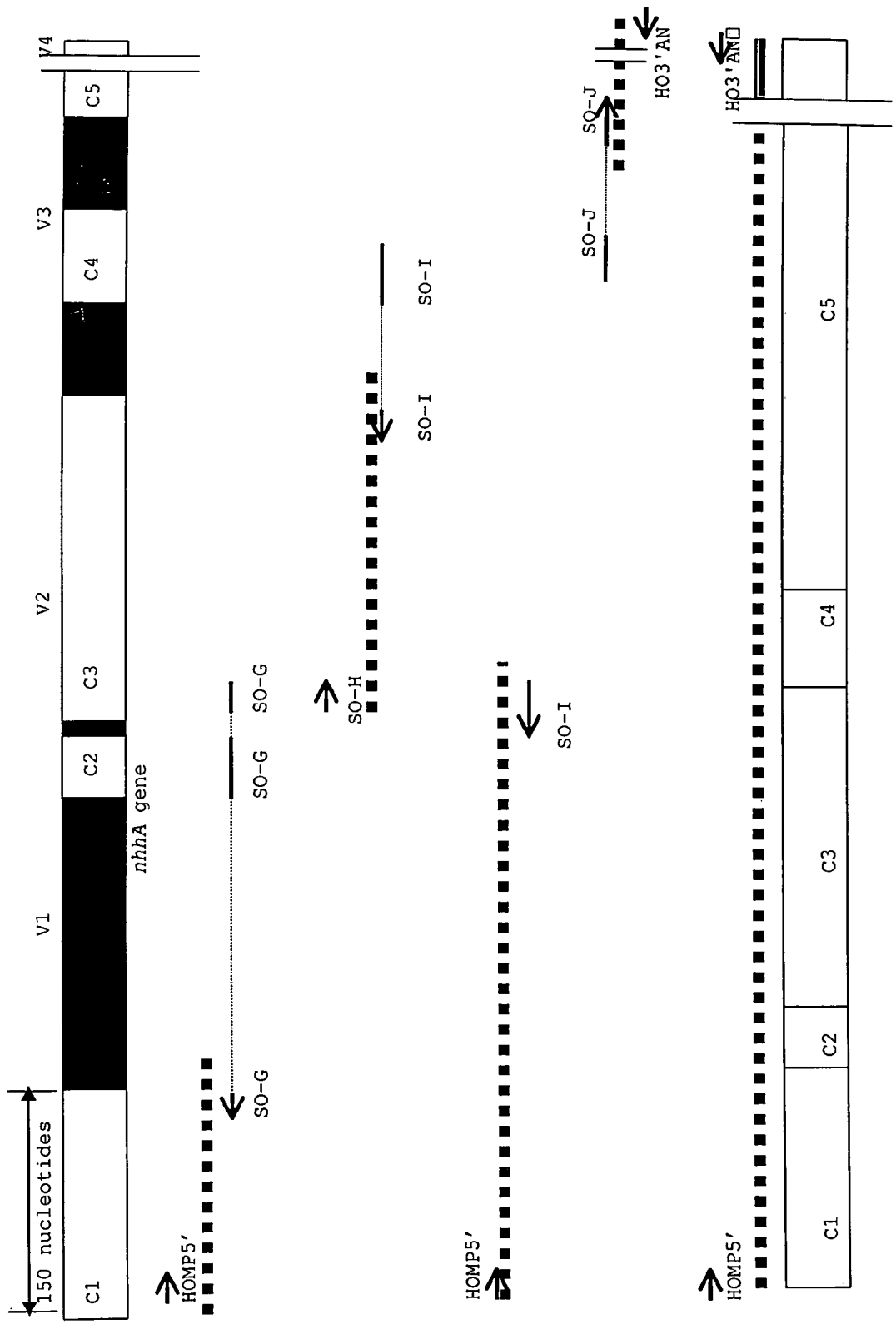

FIG. 4 (comprising FIGS. 4A-4C): Schematic representation of Splice Overlap Extension PCR strategy for deletion of specific regions of NhhA polypeptides. A schematic of the wild-type nhhA gene is shown at the top of FIGS. 4A-C, and the recombinant nhhA is shown at the bottom of these figures, with variable regions shown as black and constant regions by unfilled boxes. Arrows indicate approximate location of oligonucleotide primers. Vertical hatched lines indicate amplification products. Where oligonucleotide sequence is from discontinuous regions of an nhhA nucleic acid, this is shown by a dotted line between such discontinuous regions. Approximate scale indicated. Double vertical lines indicate that only a portion of the C5 region is shown. FIG. 4A: shows the strategy as described in Example 6. FIG. 4B: shows the strategy as described in Example 7. FIG. 4C: shows the strategy as described in Example 8.

FIG. 5 (comprising FIGS. 5A and 5B): FIG. 5A Amino acid sequence of PMC 21 NhhA deletion mutant polypeptide (SEQ ID NO:23) produced in Example 4; and FIG. 5B encoding nucleotide sequence (SEQ ID NO:28).

FIG. 6 (comprising FIGS. 6A and 6B): FIG. 6A Amino acid sequence of H41 NhhA deletion mutant polypeptide (SEQ ID NO:24) produced in Example 5; and FIG. 6B encoding nucleotide sequence (SEQ ID NO:29).

FIG. 7 (comprising FIGS. 7A and 7B): FIG. 7A Amino acid sequence of PMC21 NhhA deletion mutant polypeptide (SEQ ID NO:25) produced by splice overlap PCR in Example 6; and FIG. 7B encoding nucleotide sequence (SEQ ID NO:30).

FIG. 8 (comprising FIGS. 8A and 8B): FIG. 8A Amino acid sequence of PMC21 NhhA deletion mutant polypeptide (SEQ ID NO:26) produced by splice overlap PCR in Example 7; and FIG. 8B encoding nucleotide sequence (SEQ ID NO:31).

FIG. 9 (comprising FIGS. 9A and 9B): FIG. 9A Amino acid sequence of PMC21 NhhA deletion mutant polypeptide (SEQ ID NO: 27) produced by splice overlap PCR in Example 8; and FIG. 9B encoding nucleotide sequence (SEQ ID NO:32).

FIG. 10 (comprising FIGS. 10A and 10B): Amino acid sequence alignments of wild type and NhhA deletion mutant polypeptide sequences. These polypeptides were produced as described in Example 2, Example 3, Example 4 and Example 5. Amino acids are indicated by the one letter abbreviation. Conserved regions labeled C1, C2, C3, C4 and C5 corresponding to those defined in Table 1 and FIG. 1 are indicated by double underlining of full length sequences from H41 and PMC21, and variable regions labeled V1, V2, V3, V4 corresponding to those defined in Table 1 and FIG. 1 are indicated by single underlining of full length sequences from H41 and PMC21.

Figure 11:
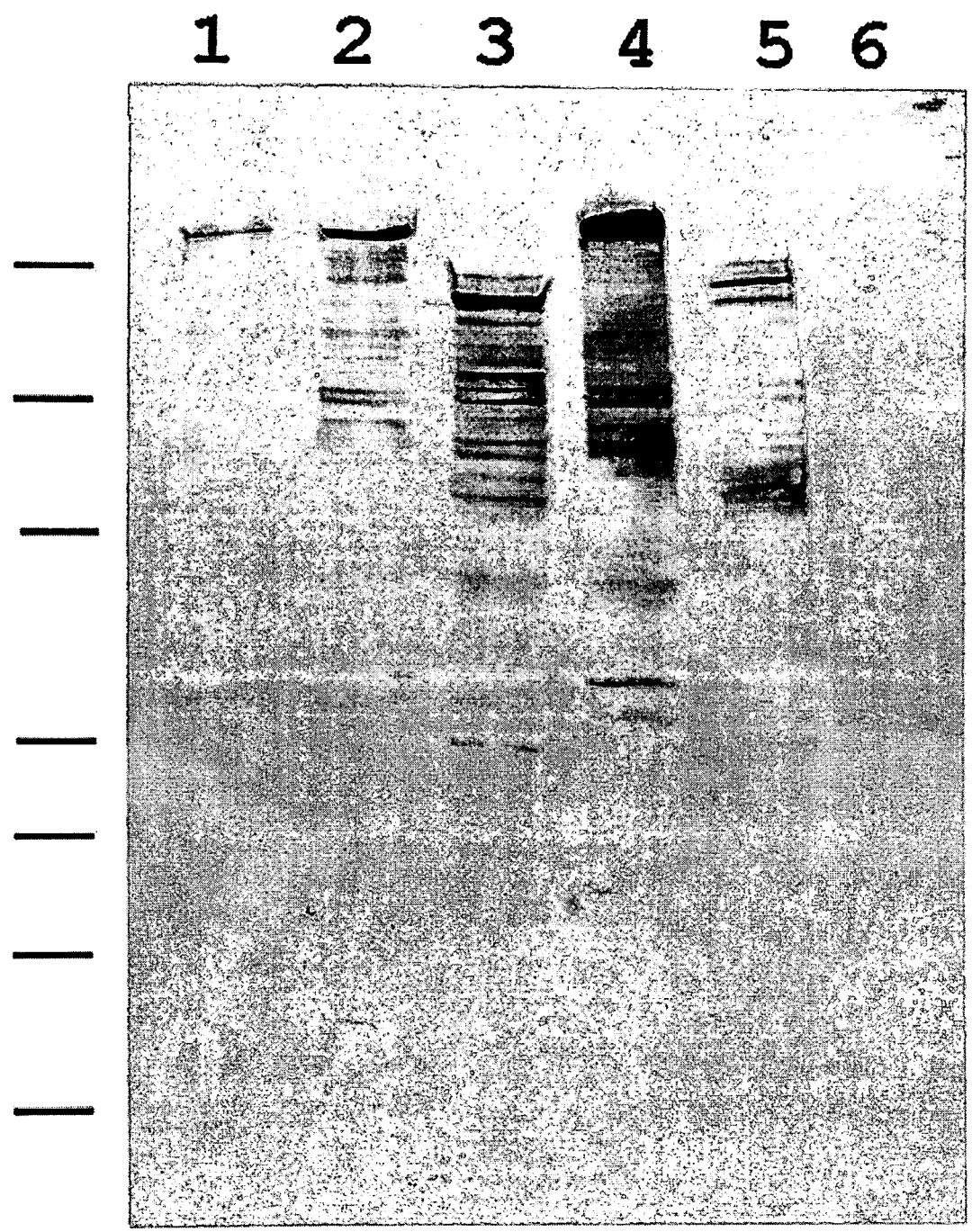

FIG. 11: Western immunoblot showing over expressed NhhA. 45 μg total cell protein was separated on 4-20% gradient SDS-PAGE before transfer to a nitrocellulose filter and western immunoblot as described in Example 9. Lane 1: Parental strain showing wild-type level of NhhA expression. Lane 2: Strain P6 (overexpresses PMC21 NhhA as described in Example 2). Lane 3: Strain PΔ6 (overexpresses the truncated PMC21 NhhA described in Example 4). Lane 4: Strain H14 (overexpresses H41 NhhA described in Example 3). Lane 5: Strain HΔ8 (overexpresses the truncated H41 NhhA described in Example 5). Lane 6: Strain 2A (NhhA expression abolished by mutation of nhhA gene as described in International Publication WO99/31132). Migration of standards is indicated: 185 kDa, 119 kDa, 85 kDa, 62 kDa, 51.2 kDa, 38.2 kDa, 22.4 kDa. Wild-type NhhA polypeptide is present as a high molecular weight immunoreactive band present in lane 1 but absent from lane 6.

Figure 12:
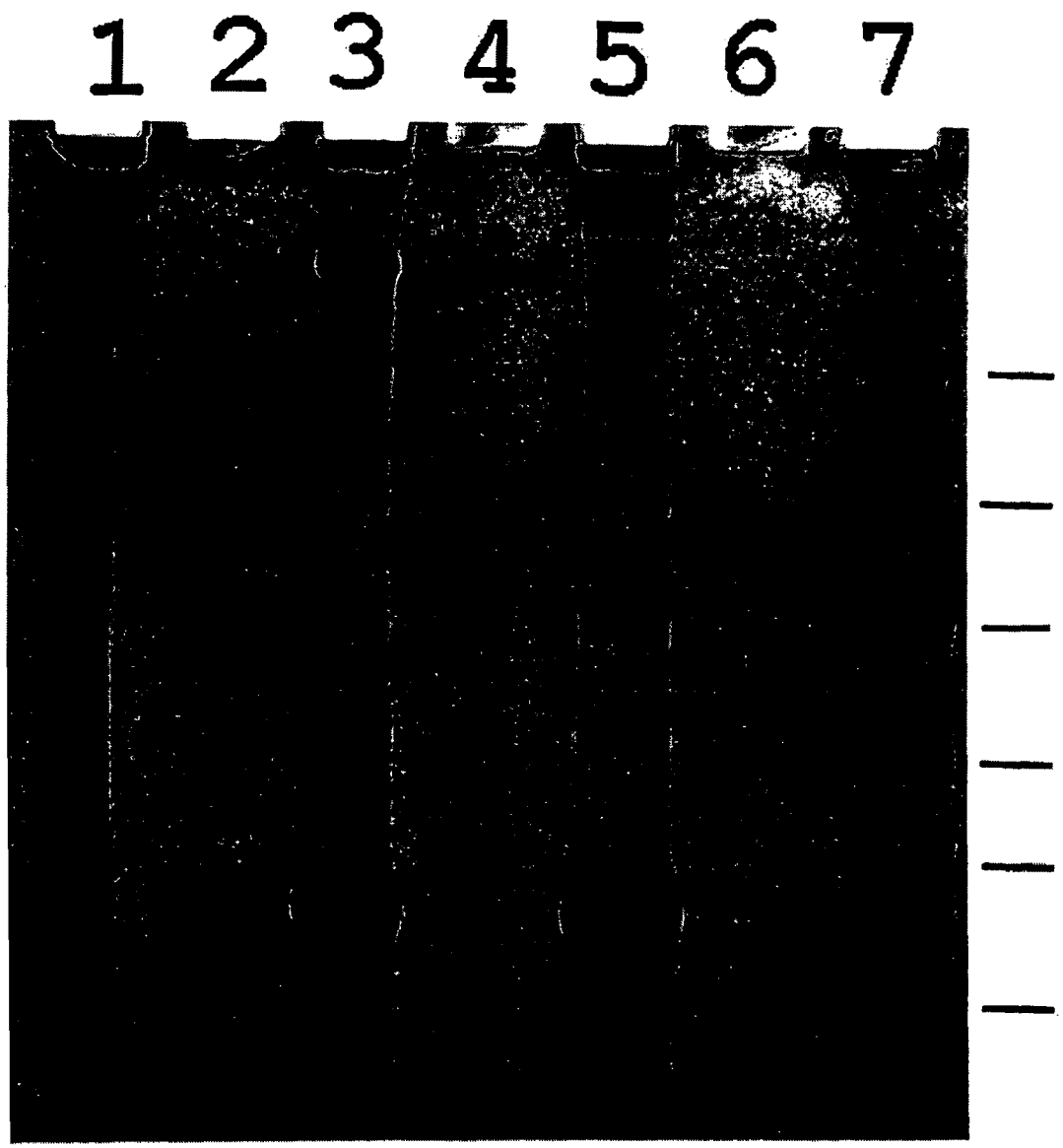

FIG. 12: Isolated NhhA deletion mutant polypeptides. NhhA polypeptides were isolated as described in Example 9 before separation on 4-20% SD-PAGE. The polyacrylamide gel was Coomassie stained. Lane 1: OMC preparation of Strain overexpressing the truncated PMC21 NhhA polypeptide described in Example 6. Lane 2: Purified truncated PMC21 NhhA polypeptide. Lane 3: OMC preparation of Strain over-expressing the truncated PMC21 NhhA polypeptide described in Example 4. Lane 4: Purified truncated PMC21 NhhA polypeptide. Lane 5: OMC preparation of a strain overexpressing PMC21 NhhA polypeptide described in Example 2. Lane 6: Purified PMC21 NhhA polypeptide. Lane 7: Molecular weight standards of 173 kDa, 111 kDa, 80 kDa, 61 kDa, 49 kDa, 36 kDa. Note that the reactive high molecular weight species in all lanes except 6 probably represents multimers of NhhA polypeptides. Other bands are probably less stable forms of NhhA or breakdown products. Note these are absent from lane 6.

Figure 13:
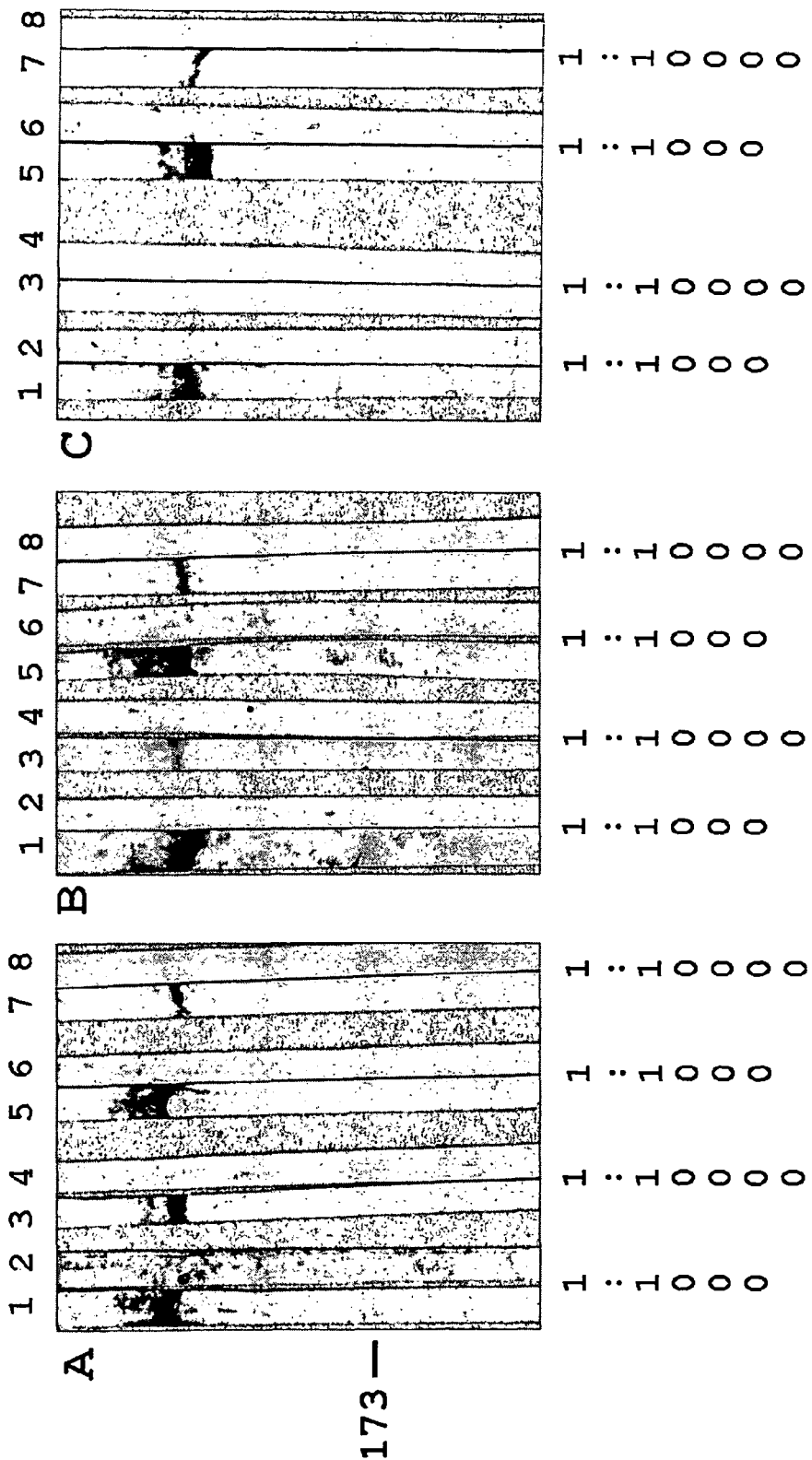

FIG. 13 (comprising FIGS. 13A-13C): Western Immunoblot using anti-NhhA protein mouse sera. In all of FIGS. 13A-13C, lanes 1, 3, 5, 7, contain OMC of Strain over expressing PMC21 NhhA polypeptide, and lanes 2, 4, 6, and 8 contain OMC of strain 2A which does not express NhhA. FIG. 13A: Lanes 1 and 2: mouse A inoculated with wild-type PMC21 NhhA at a 1:1000 dilution. Lanes 3 and 4: mouse A inoculated with wild-type PMC21 NhhA at a 1:10.000 dilution. Lanes 5 and 6, mouse B inoculated with wild-type PMC21 NhhA at a 1:1000 dilution. Lanes 7 and 8: mouse B inoculated with wild-type PMC21 NhhA at a 1:10.000 dilution. FIG. 13B: Lanes 1 & 2: mouse C inoculated with truncated PMC21 NhhA polypeptide (Example 4) at a 1:1000 dilution. Lanes 3 & 4: mouse C inoculated with truncated PMC21 NhhA polypeptide (Example 4) at a 1:10,000 dilution. Lanes 5 & 6: mouse D inoculated with truncated PMC21 NhhA (Example 4) at a 1:1000 dilution. Lanes 7 and 8: mouse D inoculated with truncated PMC21 NhhA (Example 4) at a 1:1000 dilution. FIG. 13C: Lanes 1 & 2: mouse E inoculated with truncated PMC21 NhhA (Example 6) at a 1:1000 dilution. Lanes 3 and 4: mouse E inoculated with truncated PMC21 NhhA (Example 6) at a 1:10,000 dilution. Lanes 5 & 6: mouse F inoculated with truncated PMC21 NhhA (Example 6) at a 1:1000 dilution. Lanes 7 & 8: mouse F inoculated with truncated PMC21 NhhA (Example 6) at a 1:1000 dilution.

FIG. 14 (comprising FIGS. 14A-14G): Predicted mature NhhA polypeptide deletion mutants. FIG. 14A: predicted mature protein described in Example 2 (SEQ ID NO:33); FIG. 14B: predicted mature protein described in Example 3 (SEQ ID NO:34); FIG. 14C: predicted mature protein described in Example 4 (SEQ ID NO:35); FIG. 14D: predicted mature protein described in Example 5 (SEQ ID NO:36); FIG. 14E: predicted mature protein described in Example 6 (SEQ ID NO:37); FIG. 14F: predicted mature protein described in Example 7 (SEQ ID NO:38); and FIG. 14G: predicted mature protein described in Example 8 (SEQ ID NO:39).

DETAILED DESCRIPTION OF THE INVENTION

Throughout this specification, unless the context requires otherwise, the words "comprise", "comprises" and "comprising" will be understood to imply the inclusion of a stated integer or group of integers but not the exclusion of any other integer or group of integers.

With regard to nomenclature, NhhA is used herein when reference is made to proteins of the invention, while nhhA is used herein when reference is made to nucleic acids of the invention. It will also be understood that NhhA/nhhA proteins and nucleic acids include the HiaNm/hianm proteins and nucleic acids referred to in WO99/31132, for example, without limitation thereto.

The present invention is predicated, at least in part, by the elucidation of conserved and less-conserved regions in the NhhA polypeptide in ten (10) strains of *N. meningitidis*. Corresponding regions are predicted to be conserved in other allelic variants of the exemplified NhhA polypeptides.

It will be appreciated that central to the present invention is the realization that by deleting non-conserved amino acids in a wild-type NhhA polypeptide to form a modified NhhA polypeptide of the invention, an immune response may be elicited upon immunization by said polypeptide of the invention which, by directing the immune response against conserved epitopes, will provide protection against one or more heterologous stains of *N. meningitidis*.

As used herein, "non-conserved" amino acids are amino acid residues present in a wild-type NhhA polypeptide from a first *N. meningitidis* strain, but which are not present in a wild-type NhhA polypeptide from one or more other strains.

Suitably, the polypeptides of the first aspect have at least a portion of one of the V1, V2, V3 or V4 regions deleted with respect to the corresponding wild-type sequence, and accordingly, may be collectively referred to as examples of "deletion mutants".

It will be appreciated that the present inventors have identified the V1, V2, V3 and V4 regions as being regions of wild-type NhhA polypeptides having relatively high frequencies of non-conserved amino acids compared to the relatively conserved C1-5 regions.

Of the V regions, the V1 (hypervariable) and V2 regions have the highest frequency of non-conserved amino acids, while V3 and V4 have relatively lower frequencies. However, the V1 region constitutes a more significant proportion of wild-type NhhA polypeptides than does the V2 region (in terms of total amino acids). Therefore, it is preferred that the isolated proteins according to the first-mentioned aspect have at least a substantial portion of the V1 region deleted.

It will also be realized by the skilled person that in constructing said deletion mutants, "shuffling" of regions between NhhA polypeptides of different *N. meningitidis* strains is possible. For example, an NhhA polypeptide of the invention may comprise a H41 C1 region together with a PMC21 C5 region.

Such "shuffling" is particularly well-suited to recombinant DNA methods.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native or recombinant form.

By "protein" is meant an amino acid polymer. The amino acids may be natural or non-natural amino acids as are well understood in the art.

A "peptides" is a protein having no more than fifty (50) amino acids.

A polypeptide is a protein having fifty (50) or more amino acids.

As used herein, the phrase "elicits an immune response" refers to the ability of an isolated polypeptide of the invention to produce an immune response in a mammal to which it is administered, wherein the response is directed to *N. meningitidis* and/or said polypeptide. Preferably, the immune response includes production of bactericidal antibodies. More preferably, the immune response is protective against *N. meningitidis* infection.

"Strain-specific" is used herein in the context of an immune response which is directed to, or at least predominantly directed to, an autologous *N. meningitidis* strain.

As used herein, "cross-reactive" means an ability of a polypeptide of the invention to elicit an immune response directed to one or more heterologous *N. meningitidis* strains.

As used herein, "cross-protective" means an ability of a polypeptide of the invention to elicit an immune response and thereby provide protection against infection by one or more heterologous *N. meningitidis* strains.

Therefore, in light of the foregoing, said polypeptide of the invention may be referred to herein as an "immunogen", or as being "immunogenic".

Although for the purposes of the present invention, said modified NhhA proteins have been exemplified by the amino acid sequences set forth in FIGS. 5 to 9 (SEQ ID NOS: 23-27) and FIG. 14, the present invention also contemplates fragments, derivatives and variants (such as allelic variants) of the exemplified proteins.

For example, amino acids can be deleted from any of the C1-5 sequences set forth in FIG. 1, while not all non-conserved amino acids in the V1-4 regions need be deleted in order to reduce strain-specific immunogenicity.

Therefore, isolated proteins of the invention may include fragments of the C1-5 and V1-4 regions.

Indeed, as will be described hereinafter in the Examples, it may be advantageous for the purposes of recombinant DNA-based production of polypeptides of the invention, to delete one or a few amino acids of a C1, C2, C3, C4 and/or C5 region or a V1, V2, V3 and/or V4 region in the interests of utilizing convenient restriction endonuclease sites and achieving high level expression of stable, immunogenic protein.

In one embodiment, a "fragment" includes an amino acid sequence that constitutes less than 100%, but at least 20%, preferably at least 50%, more preferably at least 80% or even more preferably at least 90% of said C1, C2, C3, C4 or C5 regions.

Fragments, for example, may be peptides comprising as few as twelve amino acids such as the C2 region (SEQ ID NO:11) or sequences of at least twenty contiguous amino acids, or more than one hundred contiguous amino acids corresponding to some or all of the C1, C2, C3, C4 and/or C5 regions described herein.

Other fragments exemplified herein are modified NhhA polypeptides of the invention which have undergone post-translational processing to form a mature polypeptide, such as shown in FIG. 14.

In another embodiment, a "fragment" is a small peptide, for example of at least 6, preferably at least 10 and more preferably at least 20 amino acids in length, which comprises one or more antigenic determinants or epitopes derived from modified NhhA proteins of the invention. Larger fragments comprising more NhhA one peptide are also contemplated, and may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a polypeptide of the invention with proteinases such as endoLys-C, endoArg-C, endoGlu-C and staphylococcins V8-protease. The digested fragments can be purified by, for example, high performance liquid chromatographic (HPLC) techniques.

As used herein, "variant" polypeptides are polypeptides of the invention in which one or more amino acids have been replaced by different amino acids. It is well understood in the art that some amino acids may be changed to others with broadly similar properties without changing the nature of the activity of the polypeptide (conservative substitutions). Exemplary conservative substitutions in the polypeptide may be made according to Table 2.

Substantial changes in function are made by selecting substitutions that are less conservative than those shown in Table 2. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

The term "variant" also includes NhhA polypeptides of the invention produced from allelic variants of the sequences exemplified in this specification.

NhhA polypeptide variants may fall within the scope of the term "polypeptide homologs".

Polypeptide homologs share at least 70%, preferably at least 80% and more preferably at least 90% sequence identity with the amino acid sequences of modified NhhA polypeptides of the invention as hereinbefore described.

As generally used herein, a "homolog" shares a definable nucleotide or amino acid sequence relationship with a nucleic acid or polypeptide of the invention as the case may be.

For example, such homologs are contemplated as having amino acid sequences that differ from those exemplified herein, but which are immunogenic and provide cross-protective immunity.

Specifically excluded from the scope of the term "homologs" are wild-type NhhA polypeptides and nhhA nucleic acids.

Included within the scope of homologs are "orthologs", which are functionally-related polypeptides and their encoding nucleic acids, isolated from bacterial species other than *N. meningitidis*.

Terms used herein to describe sequence relationships between respective nucleic acids and polypeptides include "comparison window", "sequence identity", "percentage of sequence identity" and "substantial identity". Because respective nucleic acids/polypeptides may each comprise (1) only one or more portions of a complete nucleic acid/polypeptide sequence that are shared by the nucleic acids/polypeptides, and (2) one or more portions which are divergent between the nucleic acids/polypeptides, sequence comparisons are typically performed by comparing sequences over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference.

A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

Thus, it is well within the capabilities of the skilled person to prepare polypeptide homologs of the invention, such as variants as hereinbefore defined, by recombinant DNA technology. For example, nucleic acids of the invention can be mutated using either random mutagenesis for example using transposon mutagenesis, or site-directed mutagenesis The resultant DNA fragments are then cloned into suitable expression hosts such as *E. coli* using conventional technology and clones that retain the desired activity are detected. Where the clones have been derived using random mutagenesis techniques, positive clones would have to be sequenced in order to detect the mutation.

As used herein, "derivative" polypeptides are polypeptides of the invention which have been altered, for example by conjugation or complexing with other chemical moieties or by post-translational modification techniques as would be understood in the art. Such derivatives include amino acid deletions and/or additions to NhhA polypeptides of the invention, or variants thereof, wherein said derivatives elicit an immune response.

"Additions" of amino acids may include fusion of the polypeptides or variants thereof with other polypeptides or proteins. In this regard, it will be appreciated that the polypeptides or variants of the invention may be incorporated into larger polypeptides, and such larger polypeptides may also be expected to be immunogenic. The polypeptides as described above may be fused to a further protein, for example, which is not derived from N. meningitidis. The other protein may, by way of example, assist in the purification of the protein. For instance a polyhistidine tag, or a maltose binding protein may be used. Alternatively, it may produce an immune response which is effective against N. meningitidis or it may produce an immune response against another pathogen. Other possible fusion proteins are those which produce an immunomodulatory response. Particular examples of such proteins include Protein A or glutathione S-transferase (GST). In addition, the polypeptide may be fused to an oligosaccharide based vaccine component where it acts as a carrier protein.

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$, and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

The invention also contemplates covalently modifying a polypeptide, fragment or variant of the invention with dinitrophenol, in order to render it immunogenic in humans Isolated proteins of the invention (inclusive of fragments, variants, derivatives and homologs) may be prepared by any suitable procedure known to those of skill in the art.

For example, the protein may be prepared as a recombinant polypeptide by a procedure including the steps of:
  (i) preparing an expression construct which comprises a modified nhhA nucleic acid of the invention, operably linked to one or more regulatory nucleotide sequences;
  (ii) transfecting or transforming a suitable host cell with the expression construct; and
  (iii) expressing the recombinant polypeptide in said host cell.

A number of Examples will be provided hereinafter which describe production of modified nhhA nucleic acids of the invention by PCR.

In one particular embodiment, PCR is splice overlap PCR, as will be described hereinafter, which method is based on that described in Ho et al., 1989, Gene 77 51, and by Horton et al., 1989, Gene 77 61, which are both incorporated herein by reference.

For the purposes of host cell expression, the recombinant nucleic acid is operably linked to one or more regulatory sequences in an expression vector.

An "expression vector" may be either a self-replicating extra-chromosomal vector such as a plasmid, or a vector that integrates into a host genome.

By "operably linked" is meant that said regulatory nucleotide sequence(s) is/are positioned relative to the recombinant nucleic acid of the invention to initiate, regulate or otherwise control transcription.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selectable marker genes are well known in the art and will vary with the host cell used.

In an embodiment, the expression vector is pCO14K, which has a porA promoter and kanamycin selection gene, as will be described in detail hereinafter. According to this embodiment, the host cell is a bacterium selected from the group consisting of *E. coli* and *N. meningitidis.*

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a nucleotide sequence according to the invention into the expression vector so that the translational reading frames of the fusion partner and the nucleotide sequence of the invention coincide.

Well known examples of fusion partners include, but are not limited to, glutathione-S-transferase (GST), Fc potion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

A preferred fusion partner is MBP, which is described hereinafter in Example 11.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_n$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, influenza virus haemagglutinin and FLAG tags.

As hereinbefore, polypeptides of the invention may be produced by culturing a host cell transformed with said expression construct comprising a nucleic acid encoding a polypeptide, or polypeptide homolog, of the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli* or *N. meningitidis*.

In a preferred embodiment, the host cell is *N. meningitidis* which has been modified so as to not express PorA, Opa, Opc or capsular polysaccharide and expresses a desired lipopolysaccharide phenotype.

Alternatively, the host cell may be an insect cell such as, for example, SF9 cells that may be utilized with a baculovirus expression system.

The recombinant protein may be conveniently prepared by a person skilled in the art using standard protocols as for example described in Sambrook, et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

Preferred methods of expression of recombinant modified NhhA proteins of the invention, and methods for detection of expressed protein, are provided hereinafter in the Examples.

Nucleotide Sequences

The invention provides an isolated nucleic acid that encodes a modified NhhA protein of the invention Preferably, said isolated nucleic acid has a nucleotide sequence that encodes one or more NhhA polypeptide constant (C) regions as described in FIGS. 1 and 2. The isolated nucleic acid may further encode one or more non-conserved (V region) amino acids such as also identified in FIGS. 1 and 2.

Particular embodiments of such isolated nucleic acids are provided in SEQ ID NOS: 28-32 and FIGS. 5-9.

The term "nucleic acid" as used herein designates single- or double-stranded mRNA, RNA, cRNA and DNA, said DNA inclusive of cDNA and genomic DNA.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

The present invention also contemplates homologs of nucleic acids of the invention as hereinbefore defined.

Such nucleic acid homologs exclude nucleic acids encoding full-length wild-type NhhA polypeptides.

For example, nucleic acid homologs encode peptides and polypeptides, structurally related to NhhA V and C regions of the invention, that may be useful for the purposes of providing cross-protective immunity to *N. meningitidis* by immunization.

In one embodiment, nucleic acid homologs encode polypeptide homologs of the invention, inclusive of variants, fragments and derivatives thereof.

In another embodiment, nucleic acid homologs share at least 60%, preferably at least 70%, more preferably at least 80%, and even more preferably at least 90% sequence identity with the nucleic acids of the invention.

In yet another embodiment, nucleic acid homologs hybridize to nucleic acids of the invention under at least low stringency conditions, preferably under at least medium stringency conditions and more preferably under high stringency conditions.

"Hybridize and Hybridization" is used herein to denote the pairing of at least partly complementary nucleotide sequences to produce a DNA-DNA, RNA-RNA or DNA-RNA hybrid. Hybrid sequences comprising complementary nucleotide sequences occur through base-pairing between complementary purines and pyrimidines as are well known in the art.

In this regard, it will be appreciated that modified purines (for example, inosine, methylinosine and methyladenosine) and modified pyrimidines (thiouridine and methylcytosine) may also engage in base pairing.

"Stringency" as used herein, refers to temperature and ionic strength conditions, and presence or absence of certain organic solvents and/or detergents during hybridisation. The higher the stringency, the higher will be the required level of complementarity between hybridizing nucleotide sequences.

"Stringent conditions" designates those conditions under which only nucleic acid having a high frequency of complementary bases will hybridize.

Reference herein to low stringency conditions includes and encompasses:
(i) from at least about 1% v/v to at least about 15% v/v formamide and from at least about 1 M to at least about 2 M salt for hybridisation at 42° C., and at least about 1 M to at least about 2 M salt for washing at 42° C.; and
(ii) 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature.

Medium stringency conditions include and encompass:
(i) from at least about 16% v/v to at least about 30% v/v formamide and from at least about 0.5 M to at least about 0.9 M salt for hybridisation at 42° C., and at least about 0.5 M to at least about 0.9 M salt for washing at 42° C.; and
(ii) 1% Bovine Serum Albumin (BSA), 1 mM EDTA, 0.5 M NaHPO$_4$ (pH 7.2), 7% SDS for hybridization at 65° C. and (a) 2×SSC, 0.1% SDS; or (b) 0.5% BSA, 1 mM EDTA, 40 mM NaHPO$_4$ (pH 7.2), 5% SDS for washing at 42° C.

High stringency conditions include and encompass:
(i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;
(ii) 1% BSA, 1 mM EDTA, 0.5 M NaHPO$_4$ (pH 7.2), 7% SDS for hybridization at 65° C., and (a) 0.1×SSC, 0.1% SDS; or (b) 0.5% BSA, 1 mM EDTA, 40 mM NaHPO$_4$ (pH 7.2), 1% SDS for washing at a temperature in excess of 65° C. for about one hour; and
(iii) 0.2×SSC, 0.1% SDS for washing at or above 68° C. for about 20 minutes.

In general, washing is carried out at $T_m=69.3+0.41$ (G+C) %−12° C. In general, the $T_m$ of a duplex DNA decreases by about 1° C. with every increase of 1% in the number of mismatched bases.

Notwithstanding the above, stringent conditions are well known in the art, such as described in Chapters 2.9 and 2.10 of. Ausubel et al., supra, which are herein incorporated be reference. A skilled addressee will also recognize that various factors can be manipulated to optimize the specificity of the hybridization. Optimization of the stringency of the final washes can serve to ensure a high degree of hybridization.

Typically, complementary nucleotide sequences are identified by blotting techniques that include a step whereby nucleotides are immobilized on a matrix (preferably a synthetic membrane such as nitrocellulose), a hybridization step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al., supra, at pages 2.9.1 through 2.9.20. According to such methods, Southern blotting involves separating DNA molecules according to size by gel electrophoresis, transferring the size-separated DNA to a synthetic membrane, and hybridizing the membrane bound DNA to a complementary nucleotide sequence.

In dot blotting and slot blotting, DNA samples are directly applied to a synthetic membrane prior to hybridization as above.

An alternative blotting step is used when identifying complementary nucleic acids in a cDNA or genomic DNA library, such as through the process of plaque or colony hybridization. Other typical examples of this procedure is described in Chapters 8-12 of Sambrook et al., supra which are herein incorporated by reference.

Typically, the following general procedure can be used to determine hybridization conditions. Nucleic acids are blotted/transferred to a synthetic membrane, as described above. A wild type nucleotide sequence of the invention is labeled as described above, and the ability of this labeled nucleic acid to hybridize with an immobilized nucleotide sequence analyzed.

A skilled addressee will recognize that a number of factors influence hybridization. The specific activity of radioactively labeled polynucleotide sequence should typically be greater than or equal to about $10^8$ dpm/µg to provide a detectable signal. A radiolabeled nucleotide sequence of specific activity $10^8$ to $10^9$ dpm/µg can detect approximately 0.5 pg of DNA. It is well known in the art that sufficient DNA must be immobilized on the membrane to permit detection. It is desirable to have excess immobilized DNA, usually 1-10 µg. Adding an inert polymer such as 10% (w/v) dextran sulfate (MW 500, 000) or polyethylene glycol 6000 during hybridization can also increase the sensitivity of hybridization (see Ausubel et al., supra at 2.10.10).

To achieve meaningful results from hybridization between a nucleic acid immobilized on a membrane and a labeled nucleic acid, a sufficient amount of the labeled nucleic acid must be hybridized to the immobilized nucleic acid following washing. Washing ensures that the labeled nucleic acid is hybridized only to the immobilized nucleic acid with a desired degree of complementarity to the labeled nucleic acid.

Methods for detecting labeled nucleic acids hybridized to an immobilized nucleic acid are well known to practitioners in the art. Such methods include autoradiography, chemiluminescent, fluorescent and colorimetric detection.

In another embodiment, nucleic acid homologs of the invention may be prepared according to the following procedure:
(i) obtaining a nucleic acid extract from a suitable host;
(ii) creating primers which are optionally degenerate wherein each comprises a portion of a nucleotide sequence of the invention; and
(iii) using said primers to amplify, via nucleic acid amplification techniques, one or more amplification products from said nucleic acid extract.

Suitably, the host is a bacterium.
Preferably, the host is of the genus *Neisseria*.
More preferably, the host is *N. meningitidis* or *N. lactamica*.

Primers useful according to nucleic acid sequence amplification methods include SEQ ID NOS:40-51 as described in detail hereinafter.

Suitable nucleic acid amplification techniques are well known to the skilled addressee, and include polymerase chain reaction (PCR) as for example described in Chapter 15 of Ausubel et al. supra, which is incorporated herein by reference; strand displacement amplification (SDA) as for example described in U.S. Pat. No. 5,422,252 which is incorporated herein by reference; rolling circle replication (RCR) as for example described in Liu et al., 1996, J. Am. Chem. Soc. 118 1587 and International application WO 92/01813 and Lizardi et al., (International Application WO 97/19193) which are incorporated herein by reference; nucleic acid sequence-based amplification (NASBA) as for example described by Sooknanan et al., 1994, Biotechniques 17 1077) which is incorporated herein by reference; and Q-β replicase amplification as for example described by Tyagi et al., 1996, Proc. Natl. Acad. Sci. USA 93 5395 which is incorporated herein by reference.

As used herein, an "amplification product" refers to a nucleic acid product generated by nucleic acid amplification techniques.

Antibodies

The invention also contemplates antibodies against the isolated proteins fragments, variants and derivatives of the invention. Antibodies of the invention may be polyclonal or monoclonal. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. *Antibodies: A Laboratory Manual*, Cold Spring Harbor, Cold Spring Harbor Laboratory, 1988, which are both herein incorporated by reference.

Generally, antibodies of the invention bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

In lieu of the polyclonal antisera obtained in the production species, monoclonal antibodies may be produced using the standard method as for example, described in an article by Köhler & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the polypeptides, fragments, variants or derivatives of the invention.

The invention also includes within its scope antibodies which comprise Fc or Fab fragments of the polyclonal or monoclonal antibodies referred to above. Alternatively, the antibodies may comprise single chain Fv antibodies (scFvs) against the peptides of the invention. Such scFvs may be prepared, for example, in accordance with the methods described respectively in U.S. Pat. No. 5,091,513, European Patent No 239,400 or the article by Winter & Milstein, 1991, Nature 349 293, which are incorporated herein by reference.

The antibodies of the invention may be used for affinity chromatography in isolating natural or recombinant *N. meningitidis* polypeptides. For example reference may be made to immunoaffinity chromatographic procedures described in Chapter 9.5 of Coligan et al., CURRENT PROTOCOLS IN IMMUNOLOGY, supra.

The antibodies may be used to:
(i) screen expression libraries to identify variant polypeptides of the invention;
(ii) identify immunoreactive fragments or immunoreactive epitopes; and/or
(iii) detect *N. meningitidis* infection;

as will be described hereinafter but without limitation to these particular uses.

Detection of *N. Meningitidis*

The presence or absence of *N. meningitidis* in an individual may be determined by isolating a biological sample from said individual, mixing an antibody or antibody fragment described above with the biological sample, and detecting specifically bound antibody or antibody fragment which indicates the presence of *N. meningitidis* in the sample.

The term "biological sample" as used herein refers to a sample that may be extracted, untreated, treated, diluted or concentrated from an individual, such as a patient. Suitably, the biological sample is selected from the group consisting of whole blood, serum, plasma, saliva, urine, sweat, ascitic fluid, peritoneal fluid, synovial fluid, amniotic fluid, cerebrospinal fluid, skin biopsy, and the like.

Any suitable technique for determining formation of the complex may be used. For example, an antibody or antibody fragment according to the invention having a label associated therewith may be utilized in immunoassays. Such immunoassays may include, but are not limited to, radioimmunoassays (RIAs), enzyme-linked immunosorbent assays (ELISAs) and immunochromatographic techniques (ICTs) which are well known those of skill in the art.

For example, reference may be made to Chapter 7 of Coligan et al., CURRENT PROTOCOLS IN IMMUNOLOGY, supra which discloses a variety of immunoassays that may be used in accordance with the present invention. Immunoassays may include competitive assays as understood in the art.

The label associated with the antibody or antibody fragment may include the following:
(A) direct attachment of the label to the antibody or antibody fragment;
(B) indirect attachment of the label to the antibody or antibody fragment; i.e., attachment of the label to another assay reagent which subsequently binds to the antibody or antibody fragment; and
(C) attachment to a subsequent reaction product of the antibody or antibody fragment.

The label may be selected from a group including a chromogen, a catalyst, an enzyme, a fluorophore, a chemiluminescent molecule, a lanthanide ion such as Europium ($Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels is disclosed in U.S. Pat. No. 4,366,241, U.S. Pat. No. 4,843,000, and U.S. Pat. No. 4,849,338, all of which are herein incorporated by reference. Enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution.

Suitably, the fluorophore is selected from a group including fluorescein isothiocyanate (FITC), tetramethylrhodamine isothiocyanate (TRITL) or R-Phycoerythrin (RPE).

The invention also extends to a method for detecting infection of patients by *N. meningitidis*, said method comprising the steps of contacting a biological sample from a patient with a polypeptide, fragment, variant or derivative of the invention, and determining the presence or absence of a complex between said polypeptide, fragment, variant or derivative and *N. meningitidis*-specific antibodies in said serum, wherein the presence of said complex is indicative of said infection.

In a preferred embodiment, detection of the above complex is effected by detectably modifying said polypeptide, fragment, variant or derivative with a suitable label as is well known in the art and using such modified compound in an immunoassay as for example described above.

In another aspect, the invention provides a method of detecting *N. meningitidis* bacteria in a biological sample suspected of containing said bacteria, said method comprising the steps of isolating the biological sample from a patient, detecting a nucleic acid sequence according to the invention in said sample which indicates the presence of said bacteria. Detection of the said nucleic acid sequence may be determined using any suitable technique. For example, a labeled nucleic acid according to the invention may be used as a probe in a Southern blot of a nucleic acid extract obtained from a patient as is well known in the art.

Alternatively, a labeled nucleic acid according to the invention may be utilized as a probe in a Northern blot of a RNA extract from the patient.

Preferably, a nucleic acid extract from the patient is utilized in concert with oligonucleotide primers corresponding to sense and antisense sequences of a nucleic acid sequence according to the invention, or flanking sequences thereof, in a nucleic acid amplification reaction such as PCR, or the ligase chain reaction (LCR) as for example described in International Application WO89/09385 which is incorporated by reference herein.

A variety of automated solid-phase detection techniques are also appropriate. For example, very large scale immobilized primer arrays (VLSIPS™) are used for the detection of nucleic acids as for example described by Fodor et al., 1991, Science 251 767 and Kazal et al., 1996, Nature Medicine 2 753. The above generic techniques are well known to persons skilled in the art.

Pharmaceutical Compositions

A further feature of the invention is the use of the polypeptide, fragment, variant or derivative of the invention ("immunogenic agents") as actives in a pharmaceutical composition for protecting patients against infection by *N. meningitidis*.

Suitably, the pharmaceutical composition comprises a pharmaceutically-acceptable carrier, diluent or excipient.

By "pharmaceutically-acceptable carrier, diluent or excipient" is meant a solid or liquid filler, diluent or encapsulating substance that may be safety used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is immunogenically-effective to protect patients from *N. meningitidis* infection. The dose administered to a patient, in the context of the present invention, should be sufficient to effect a beneficial response in a patient over time such as a reduction in the level of *N. meningitidis*, or to inhibit infection by *N. meningitidis*. The quantity of the immunogenic agent(s) to be administered may depend on the subject to be treated inclusive of the age, sex, weight and general health condition thereof. In this regard, precise amounts of the immunogenic agent(s) required to be administered will depend on the judgment of the practitioner.

In determining the effective amount of the immunogenic agent to be administered in the treatment or prophylaxis against *N. meningitidis*, the physician may evaluate circulating plasma levels, progression of disease, and the production of anti-*N. meningitidis* antibodies. In any event, suitable dosages of the immunogenic agents of the invention may be readily determined by those of skill in the art. Such dosages may be in the order of nanograms to milligrams of the immunogenic agents of the invention.

The above compositions may be used as therapeutic or prophylactic vaccines. Accordingly, the invention extends to the production of vaccines containing as actives one or more of the immunogenic agents of the invention. A variety of applicable procedures are contemplated for producing such vaccines. Exemplary procedures include, for example, those described in NEW GENERATION VACCINES (1997, Levine et al., Marcel Dekker, Inc. New York, Basel Hong Kong) which is incorporated herein by reference.

An immunogenic agent according to the invention can be mixed, conjugated or fused with other antigens, including B or T cell epitopes of other antigens. In addition, it can be conjugated to a carrier as described below.

When an haptenic peptide of the invention is used (i.e., a peptide which reacts with cognate antibodies, but cannot itself elicit an immune response), it can be conjugated with an immunogenic carrier. Useful carriers are well known in the art and include for example: thyroglobulin; albumins such as human serum albumin; toxins, toxoids or any mutant cross-reactive material (CRM) of the toxin from tetanus, diptheria, pertussis, *Pseudomonas, E. coli, Staphylococcus*, and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immnogenic protein may be used. For example, a haptenic peptide of the invention can be coupled to a T cell epitope of a bacterial toxin, toxoid or CRM. In this regard, reference may be made to U.S. Pat. No. 5,785,973 which is incorporated herein by reference.

In addition, a polypeptide, fragment, variant or derivative of the invention may act as a carrier protein in vaccine compositions directed against *Neisseria*, or against other bacteria or viruses.

The immunogenic agents of the invention may be administered as multivalent subunit vaccines in combination with antigens of *N. meningitidis*, or antigens of other organisms inclusive of the pathogenic bacteria *H. influenzae, M. catarrhalis, N. gonorrhoeae, E. coli, S. pneumoniae*, etc. Alternatively or additionally, they may be administered in concert with oligosaccharide or polysaccharide components of *N. meningitidis*.

The vaccines can also contain a pharmaceutically-acceptable carrier, diluent or excipient as hereinbefore defined.

The vaccines and immunogenic compositions may include an adjuvant as is well known in the art. Adjuvants contemplated by the present invention include, but are not limited to: surface active substances such as hexadecylamine, octadecylamine, octadecyl amino acid esters, lysolecithin, dimethyldioctadecylammonium bromide, N,N-dicoctadecyl-N',N'bis (2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (IS-COMS).

With regard to examples of adjuvants, reference is also made to International Publication WO99/36544 incorporated herein by reference.

Vaccination by DNA Delivery

Expression constructs comprising modified NhhA proteins of the invention may be administered to humans to prophylactically and/or therapeutically treat the host. In this regard, expression constructs may encode one or more modified NhhA peptides, polypeptides, fragments or derivatives of these, collectively referred to as "immunogenic agents".

Expression constructs also include gene therapy constructs, which employ specialized gene therapy vectors such as vaccinia, and viral vectors useful in gene therapy. The latter include adenovirus and adenovirus-associated viruses (AAV) such as described in Franceschi et al., 2000, J. Cell Biochem. 78 476, Braun-Falco et al., 1999, Gene Ther. 6 432, retroviral and lentiviral vectors such as described in Buchshacher et al., 2000, Blood 95 2499 and vectors derived from herpes simplex virus and cytomegalovirus. A general review of gene therapy vectors and delivery methods may be found in Robbins et al., 1998, Trends in Biotech. 16 35. An exemplary reference which describes a number of vectors potentially suitable for gene therapy using *Neisseria* proteins, and methods of delivery, is International Publication WO99/36544 incorporated herein by reference.

The immunogenic agents of the invention may be expressed by attenuated viral hosts. By "attenuated viral hosts" is meant viral vectors that are either naturally, or have been rendered, substantially avirulent. A virus may be rendered substantially avirulent by any suitable physical (e.g., heat treatment) or chemical means (e.g., formaldehyde treatment). By "substantially avirulent" is meant a virus whose infectivity has been destroyed. Ideally, the infectivity of the virus is destroyed without affecting the proteins that carry the immunogenicity of the virus. From the foregoing, it will be appreciated that attenuated viral hosts may comprise live viruses or inactivated viruses.

Attenuated viral hosts which may be useful in a vaccine according to the invention may comprise viral vectors inclusive of adenovirus, cytomegalovirus and preferably pox viruses such as vaccinia (see for example Paoletti and Panicali, U.S. Pat. No. 4,603,112 which is incorporated herein by reference) and attenuated *Salmonella* strains (see for example Stocker, U.S. Pat. No. 4,550,081 which is herein incorporated by reference). Live vaccines are particularly advantageous because they lead to a prolonged stimulus that can confer substantially long-lasting immunity. Another reference which describes a variety of viral vectors potentially suitable for immunization using *Neisseria* proteins, and methods of delivery, is International Publication WO99/36544 incorporated herein by reference.

Multivalent vaccines can be prepared from one or more microorganisms that express different epitopes of *N. meningitidis* (e.g., other surface proteins or epitopes of *N. meningitidis*). In addition, epitopes of other pathogenic microorganisms can be incorporated into the vaccine.

In a preferred embodiment, this will involve the construction of a recombinant vaccinia virus to express a nucleic acid sequence according to the invention. Upon introduction into a host, the recombinant vaccinia virus expresses the immunogenic agent, and thereby elicits a host CTL response. For example, reference may be made to U.S. Pat. No. 4,722,848, incorporated herein by reference, which describes vaccinia vectors and methods useful in immunization protocols.

A wide variety of other vectors useful for therapeutic administration or immunization with the immunogenic agents of the invention will be apparent to those skilled in the art from the present disclosure.

In a further embodiment, the nucleotide sequence may be used as a vaccine in the form of a "naked DNA" vaccine as is known in the art. For example, an expression vector of the invention may be introduced into a mammal, where it causes production of a polypeptide in vivo, against which the host mounts an immune response as for example described in Barry, M. et al., (1995, *Nature,* 377:632-635) which is hereby incorporated herein by reference.

Detection Kits

The present invention also provides kits for the detection of *N. meningitidis* in a biological sample. These will contain one or more particular agents described above depending upon the nature of the test method employed. In this regard, the kits may include one or more of a polypeptide, fragment, variant, derivative, antibody, antibody fragment or nucleic acid according to the invention. The kits may also optionally include appropriate reagents for detection of labels, positive and negative controls, washing solutions, dilution buffers and the like. For example, a nucleic acid-based detection kit may include (i) a nucleic acid according to the invention (which may be used as a positive control), (ii) an oligonucleotide primer according to the invention, and optionally a DNA polymerase, DNA ligase etc depending on the nucleic acid amplification technique employed.

Preparation of Immunoreactive Fragments

The invention also extends to a method of identifying an immunoreactive fragment of a polypeptide, variant or derivatives according to the invention. This method essentially comprises generating a fragment of the polypeptide, variant or derivative, administering the fragment to a mammal; and detecting an immune response in the mammal. Such response will include production of elements which specifically bind *N. meningitidis* and/or said polypeptide, variant or derivative, and/or a protective effect against *N. meningitidis* infection.

Prior to testing a particular fragment for immunoreactivity in the above method, a variety of predictive methods may be used to deduce whether a particular fragment can be used to obtain an antibody that cross-reacts with the native antigen. These predictive methods may be based on amino-terminal or carboxy-terminal sequence as for example described in Chapter 11.14 of Ausubel et al., supra. Alternatively, these predictive methods may be based on predictions of hydrophilicity as for example described by Kyte & Doolittle 1982, J. Mol. Biol. 157 105 and Hopp & Woods, 1983, Mol. Immunol. 20 483) which are incorporated by reference herein, or predictions of secondary structure as for example described by Choo & Fasman, 1978, Ann. Rev. Biochem. 47 251), which is incorporated herein by reference.

In addition, "epitope mapping" uses monoclonal antibodies of the invention to identify cross-reactive epitopes by first testing their ability to provide cross-protection, followed by identifying the epitope recognized by said antibodies. An exemplary method is provided in Coligan et al., CURRENT PROTOCOLS IN IMMUNOLOGY, supra.

Generally, peptide fragments consisting of 10 to 15 residues provide optimal results. Peptides as small as 6 or as large as 20 residues have worked successfully. Such peptide fragments may then be chemically coupled to a carrier molecule such as keyhole limpet hemocyanin (KLH) or bovine serum albumin (BSA) as for example described in Sections 11.14 and 11.15 of Ausubel et al., supra).

It will also be appreciated that peptides may be synthetically circularized, as for example described in Hoogerhout et al., 1995, Infect, Immun. 63 3473, which is herein incorporated by reference.

The peptides may be used to immunize an animal as for example discussed above. Antibody titers against the native or parent polypeptide from which the peptide was selected may then be determined by, for example, radioimmunoassay or ELISA as for instance described in Sections 11.16 and 114 of Ausubel et al., supra.

Antibodies may then be purified from a relevant biological fluid of the animal by ammonium sulfate fractionation or by chromatography as is well known in the art. Exemplary protocols for antibody purification are given in Sections 10.11 and 11.13 of Ausubel et al., supra, which are herein incorporated by reference.

Immunoreactivity of the antibody against the native or parent polypeptide may be determined by any relevant procedure such as, for example, Western blot.

Functional Blockers

The wild-type NhhA/HiaNm polypeptides disclosed in WO99/31132 are believed to have adhesin properties. They in fact have some similarity to adhesins of *Haemophilus influenzae* which are surface antigens. Specifically they are approximately 67% homologous to the Hia protein of *H. influenzae* (Barenkamp & St. Geme III, 1996, Molecular Microbiology 19 1215), and 74% homologous to the Hsf protein of *H. influenzae* (St. Geme III, J. et al, 1996, Journal of Bacteriology 178 6281; and U.S. Pat. No. 5,646,259). For these comparisons, a gap weight of 3, and length weight of 0.01 was used using the GAP program (Deveraux, 1984, supra). Thus, interruption of the function of these polypeptides would be of significant therapeutic benefit since they would prevent *N. meningitidis* bacteria from adhering to and invading cells. Interruption of the function may be effected in several ways.

For example, moieties such as chemical reagents or polypeptides which block receptors on the cell surface which interact with a polypeptides of the invention may be administered. These compete with the infective organism for receptor sites. Such moieties may comprise for example polypeptides of the invention, in particular fragments, or functional equivalents of these as well as mimetics.

The term "mimetics" is used herein to refer to chemicals that are designed to resemble particular functional regions of the proteins or peptides. Anti-idiotypic antibodies raised against the above-described antibodies which block the binding of the bacteria to a cell surface may also be used. Alternatively, moieties which interact with the receptor binding sites in the polypeptides of the invention may effectively prevent infection of a cell by *N. meningitidis*. Such moieties may comprise blocking antibodies, peptides or other chemical reagents.

All such moieties, pharmaceutical compositions in which they are combined with pharmaceutically acceptable carriers and methods of treating patients suffering from *N. meningitidis* infection by administration of such moieties or compositions form a further aspect of the invention.

The polypeptides of the invention may be used in the screening of compounds for their use in the above methods. For example, polypeptides of the invention may be combined with a label and exposed to a cell culture in the presence of a reagent under test. The ability of reagent to inhibit the binding of the labeled polypeptide to the cell surface can then be observed. In such a screen, the labeled polypeptides may be used directly on an organism such as *E. coli*. Alternatively, *N. meningitidis* itself may be engineered to express a modified and detectable form of the polypeptide. The use of engineered *N. meningitidis* strains in this method is preferred as it is more likely that the tertiary structure of the protein will resemble more closely that expressed in wild-type bacteria.

In order that the invention may be readily understood and put into practical effect, particular preferred embodiments will now be described by way of the following non-limiting examples.

EXAMPLE 1

Identification of Constant and Variable Regions of NhhA Polypeptides

The present inventors have elucidated NhhA amino acid sequences which are conserved and/or non-conserved between ten (10) strains of *N. meningitidis*. The non-conserved regions are subdivided into four variable regions (V1, V2, V3 and V4) and the conserved regions are subdivided into C1, C2, C3, C4 and C5 (as shown in FIG. 1 and Table 1; SEQ ID NOS: 1-11). The corresponding nucleotide sequence comparison is shown in FIG. 2 (SEQ ID NOS: 12-22).

EXAMPLE 2

PMC21 NhhA Polypeptide Over-Expression

The NhhA protein encoded by the nhhA gene of *N. meningitidis* strain PMC21 was over expressed by making an expression construct wherein the nhhA gene is operably linked to a promoter.

The following oligonucleotide primers were used to amplify an *N. meningitidis* PMC21 strain nhhA nucleic acid open reading frame by PCR:

HOMP5': 5'-CAA TTA ACG GCC GAA TAA AAG GAA GCC GAT ATG AAC AAA ATA TAC CGC ATC-3' (SEQ ID NO 40); which contains an EagI restriction site (underlined) and the sequence encoding the first 7 (seven) amino acids of NhhA (bold type)

HOMP3'AN 5'-TGG AAT CCATGG AAT CGC CAC CCT TCC CTT C-3' (SEQ ID NO 41); which contains an NcoI restriction site (underlined) and the reverse complement of sequence 48-61 nucleotides past the end of the nhhA open reading frame of strain ¢3 (bold type)

The amplification product contained restriction sites which were subsequently digested with EagI and NcoI restriction endonucleases.

The plasmid used for subcloning was pCO14K, which plasmid contains a porA promoter upstream of the gene encoding the strongly expressed Class 1 outer membrane protein of *N. meningitidis* together with flanking sequence of *N. meningitidis* strain 2996 and a selectable kanamycin resistance gene as described by Rouppe van der Voort, et al., Infect Immun 1996 64 2745.

The digested amplification product was then ligated into EagI and NcoI restriction endonuclease-digested pCO14K. This ligation resulted in the replacement of the majority of the porA open reading frame with the nhhA amplification product (FIG. 3). This created a recombinant nucleic acid expression construct (open reading frame shown in SEQ ID NO 12) which encodes a polypeptide of 591 amino acids as shown in SEQ ID NO 1.

This places expression of the nhhA nucleic acid of the invention under the control of the strong porA promoter. Translation begins at the ATG codon beginning at position 31 of HOMP5'. In order to prevent formation of a fusion between the porA and nhhA, the HOMP5' sequence contains a TAA stop codon prior to the initiating ATG described above.

The resulting plasmid, pIP52(PMC21), was linearized by restriction digestion and used to transform *N. meningitidis* strain 7G2 using the method described by Janik et al, 1976, Journal of Clinical Microbiology 4 71. Transformants were selected by overnight incubation at 37° C. in 5% CO₂ on solid media containing 100 μg/ml kanamycin. Kanamycin resistant colonies were selected, subcultured overnight and screened for over-expression of NhhA polypeptide by separating total cell proteins electrophoretically on 10% SDS-PAGE followed by transfer to nitrocellulose membrane using a Semi-Dry Blotter (BioRad). The membrane was then incubated sequentially with rabbit anti-NhhA sera (as described in International Publication WO99/31132) and alkaline-phosphatase conjugated anti-Rabbit IgG (Sigma) before colorimetric detection with NBT/BCIP (Sigma). One clone was isolated which expressed NhhA polypeptide at a higher level compared with the parental strain (FIG. 11). Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14A; SEQ ID NO:33).

The plasmid construct pIP52(PMC21) may be transformed into any transformation-competent strain of *N. meningitidis*

EXAMPLE 3

H41 NhhA Polypeptide Over-Expression

The NhhA protein encoded by the nhhA gene of *N. meningitidis* strain H41 was over expressed using the same methods as described in Example 2. This created a recombinant nucleic acid expression construct (open reading frame shown in SEQ ID NO:13) which encodes a polypeptide of 591 amino acids as shown in SEQ ID NO:2. In this example the resulting plasmid pIP52(H41) was linearized, and transformed into *N. meningitidis* strain 7G2. Kanamycin resistant colonies were analysed and one was chosen which when examined by Western immunoblot, demonstrated overexpression of NhhA. (FIG. 11). Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14B; SEQ ID NO:34).

This strategy may be employed to create expression constructs containing the wild-type nhhA sequence of other *N. meningitidis* strains.

EXAMPLE 4

NhhA Deletion Mutant Construction Using Convenient Restriction Site

For ease of reference, the amino acid sequence of the NhhA polypeptide encoded by the nhhA nucleic acid of strain PMC21 is shown in SEQ ID NO 1. The present inventors created a deletion mutant version of wild-type PMC21 nhhA, in which the most variable region between strains was deleted. An amplification product encoding amino acids 1-54 of the wild-type PMC21 NhhA polypeptide was generated by PCR amplification from nhhA nucleic acid template using the following primers:

HOMP5': 5'-CAA TTA ACG GCC GAA TAA AAG GAA GCC GAT ATG AAC AAA ATA TAC CGC ATC-3' (SEQ ID NO 40); which is the same oligonucleotide used to create the overexpression construct pIP52.

NH3'BG: 5'-GGT CAG ATC TGT TTC ATT GTT AGC ACT TGC-3' (SEQ ID NO 42); which contains a BglII restriction site (underlined) and the reverse complement of sequence encoding amino acids 134, (double underlined) and 49-54 of wild-type PMC21 NhhA (bold type).

The resulting amplification product included an EagI and BglII restriction endonuclease sites. pIP52(PMC21) includes a single EagI site 20 bp upstream of the start of the nhhA open reading frame (ORF) and a single BglII site located within the ORF (see FIG. 3B). Therefore, pIP52(PMC21) and the amplification product were subjected to restriction endonuclease digestion with EagI and BglII, ligated and used to transform competent DH5α strain *E. coli* bacteria; this replaces the EagI/BglII fragment of pIP52(PMC21) with the PCR product. This created a recombinant nucleic acid expression construct (open reading frame shown in FIG. 5B; SEQ ID NO:28) which encodes a polypeptide of 512 amino acids as shown in FIG. 5A (SEQ ID NO:23). This amino acid sequence includes amino acids 1-54 and 134-592 of the wild-type sequence, and thereby deletes the majority of the V1 region, all of the V2 and C2 regions, and part of the C3 region of the wild-type PMC21 NhhA polypeptide.

This plasmid was linearised by restriction digestion and transformed in to *N. meningitidis* strain 7G2. Using methods as described in Example 1, one clone was isolated which overexpresses the truncated PMC21 NhhA (FIG. 11).

Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14C; SEQ ID NO:35). To confirm the presence of a cleavable signal sequence and to confirm the identity of the over expressed protein, outer membrane proteins were semi-purified by isolating the fraction that is insoluble in the detergent sarkosyl.

The isolated membrane proteins were separated electrophoretically before transfer to Nylon membrane. The position of the over expressed protein was revealed by Coomassie stain. This region of the membrane was excised and the protein was N-terminal sequenced. The first eleven amino acids of this protein were XXETDLTSVGT SEQ ID NO:52 which corresponds to amino acid residues 52 to 62 (inclusive) of the amino acid sequence predicted to be expressed by the over expression construct as defined in this example.

This is an example of a deletion using existing restriction sites within the polynucleotide sequence. This construct may be transformed into any transformation competent *N. meningitidis*.

EXAMPLE 5

NhhA Deletion Mutant Construction Using Convenient Restriction Site

An expression construct containing the wild-type nhhA sequence of H41 was made as described in Example 2. The resulting expression construct was named pIP52(H41). A deletion mutant was made, using the strategy outlined in this example. In this instance the oligonucleotide primers used were:

HOMP5': 5'-CAA TTA ACG GCC GAA TAA AAG GAA GCC GAT ATG AAC AAA ATA TAC CGC ATC-3' (SEQ ID NO:40); which is the same oligonucleotide used to create the overexpression construct pIP52

NH3'STU: 5'-GAT CAG GCC TGT ATC TTC ATC GGT AGC ATT-3' (SEQ ID NO 43); which contains a StuI restriction site (underlined) and the reverse complement of sequence encoding amino acids 134, (double underlined) and 49-54 of wild-type H41 NhhA (bold type).

The resulting amplification product contains single EagI and StuI restriction endonuclease sites. The expression construct pIP52(H41) contains these restriction sites. Therefore, pIP52(H41) and the amplification product were subjected to restriction endonuclease digestion with EagI and StuI, ligated and used to transform competent DH5α strain *E. coli* bacteria; this ligation replaces the EagI/StuI fragment of pIP52 (H41) with the PCR product. This created a recombinant nucleic acid expression construct (open reading frame shown in FIG. 6B and SEQ ID NO:29) which encodes a polypeptide of 513 amino acids as shown in FIG. 6A and SEQ ID NO:24. This amino acid sequence includes amino acids 1-54 and 134-593 of the wild-type sequence, and thereby deletes the majority of the V1 region, all of the V2 and C2 regions, and part of the C3 region of the wild-type H41 NhhA polypeptide.

This plasmid was linearised by restriction digestion and transformed in to *N. meningitidis* strain 7G2. Using methods as described in Example 1, one clone was isolated which overexpresses the truncated H41 NhhA (FIG. 11).

Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14D; SEQ ID NO:36).

This construct may be transformed into any competent *N. meningitidis.*

EXAMPLE 6

NhhA Deletion Mutant Construction Using Splice-Overlap PCR

In addition to using convenient restriction sites to delete variable regions from nucleotides encoding NhhA, mutants may also be constructed by use of "Splice Overlap Extension" PCR, as described by Ho et al., 1989, supra and by Horton, R. M., et al., 1989, supra. In this way, polynucleotides can be generated which encode constant regions, but have variable regions deleted (see FIG. 5A, 5B, 5C).

In this example, a construct was made containing the C1 and C5 regions, and all other regions deleted (see FIG. 5A).

The following oligonucleotide primers were used in PCR reactions to amplify DNA corresponding to region C1 (see FIG. 1) from chromosomal DNA of strain PMC21;

HOMP5': 5'-CAA TTA ACG GCC GAA TAA AAG GAA GCC GAT ATG AAC AAA ATA TAC CGC ATC-3' (SEQ ID NO:40); which is the same oligonucleotide used to create the over-expression construct pIP52 (PMC21)

SO-C: 5'-GACGAAATCAACGTTCTT AGC ACT TGC CTG AAC CGT TGC-3' (SEQ ID NO 44); which sequence is the reverse complement of sequence encoding amino acids 237-241 at the start of the C5 region (underlined) and amino acids 45-52 at the end of the C1 region (bold type) of wild-type NhhA of strain PMC21.

The amplification product of this reaction is HOMP5'/SO-C.

The following oligonucleotide primers were used in PCR reactions to amplify C5 from chromosomal DNA of strain PMC21:

SO-D: 5'-AACGTTGATTTCGTC CGC ACT TAC-3' (SEQ ID NO 45); which encodes amino acids 237-244 at the start of C5 (underlined indicates reverse complement of Primer SO-C), HO3'AN: 5'-TGG AAT CCA TGG AAT CGC CAC CCT TCC CTT C-3'(SEQ ID NO 41); which is the same primer used in the construction of pIP52.

The amplification product of this reaction is SO-D/HO3'AN.

The amplification products HOMP5'/SO-C and SO-D/HO3'AN were purified from an agarose gel following separation by electrophoresis, were mixed, and subjected to further amplification using primers HOMP5' and HO3'AN. The resulting amplification product encodes amino acids 1-52 and 337-591 of wild-type NhhA of PMC21. This amplification product was subjected to restriction digestion with EagI and NcoI, and cloned into pCO14K, as described in Example 1. This recombinant molecule contains regions C1 and C5, thus deleting regions V1 to 4 and C2 to 4. The nucleotide sequence of the open reading frame is shown in FIG. 7B and SEQ ID NO:30, and the predicted polypeptide sequence derived from this nucleotide sequence is shown in FIG. 7A and SEQ ID NO:25.

This plasmid was linearized by restriction digestion and transformed in to *N. meningitidis* strain 7G2. Using methods as described in Example 2, one clone was isolated which overexpresses the truncated PMC21 NhhA.

Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14E; SEQ ID NO:37).

This plasmid may be transformed into any transformation competent strain of *N. meningitidis*.

EXAMPLE 7

NhhA Deletion Mutant Construction Using Splice-Overlap PCR

It will be appreciated that a similar strategy can be used to create recombinant polynucleotides encoding various regions of NhhA. A construct can be made comprising regions C1, C4, V4 and C5 using the following strategy (see FIG. 5B):

The C1 region is amplified using oligonucleotide primers:

HOMP5': 5'-CAA TTA ACG GCC GAA TAA AAG GAA GCC GAT ATG AAC AAA ATA TAC CGC ATC-3' (SEQ ID NO:40);

SO-E: 5'-AACGCTTGCCGCACGCTT AGC ACT TGC CTG CAA CGT TGC-3' (SEQ ID NO 46); which encodes the reverse complement of amino acids 211-215 at the start of the C4 region (underlined) and at the end of the C1 region (bold type) of strain PMC21.

The amplification product of this reaction is HOMP5'/SO-E.

The following oligonucleotide primers are used in PCR reactions to amplify the region C4-V4-C5 from chromosomal DNA of strain PMC21:

SO-F: 5'-CGTGCGGCAAGCGTT AAA GAC GTA-3' (SEQ ID NO 47); which encodes amino acids 211-218 at the start of C4 (underlined indicates reverse complement of Primer SO-E),

HO3'AN: 5'-TGG AAT CCA TGG AAT CGC CAC CCT TCC CTT C-3 (SEQ ID NO:41).

The amplification product of this reaction is SO-F/HOMP3'

The amplification products HOMP5'/SO-E and SO-F/HO3'AN will be purified from agarose gel following separation by electrophoresis, and will be mixed, and subjected to further amplification using primers HOMP5' and HO3'AN. The resulting product encodes amino acids 1-52 and 211-591 of wild-type NhhA of PMC21. This amplification product will be subjected to restriction digestion with EagI and NcoI, and cloned into pCO14K. This recombinant molecule contains regions C1, C4, V4 and C5 thus deleting regions V1-3 and C2-3. The nucleotide sequence of the open reading frame is shown in FIG. 8B and SEQ ID NO:31, and the predicted polypeptide sequence derived from this nucleotide sequence is shown in FIG. 8A and SEQ ID NO:26. Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14F; SEQ ID NO:38).

This construct can be transformed into any transformation competent *N. meningitidis.*

EXAMPLE 8

NhhA Deletion Mutant Construction Using Splice-Overlap PCR

It will be appreciated that a similar strategy can be used to create recombinant polynucleotides encoding various regions of NhhA. A construct can be made comprising regions C1, C2, C3, C4, and C5 using the following strategy (see FIG. 5C):

C1 and C2 will be amplified using oligonucleotide primers:

HOMP5': 5'-CAA TTA ACG GCC GAA TAA AAG GAA GCC GAT ATG AAC AAA ATA TAC CGC ATC-3' (SEQ ID NO 40);

SO-G: 5'-CAGCGAGTAGGTGAATTGTTTGA TTTTCAGGTTGTCGCCGGCTTTGAGGGT GTT AGC ACT TGC CTG AAC CGT-3' (SEQ ID NO 48); which encodes the reverse complement of amino acids 125-129 at the start of the C3 region (underlined), aft of the C2 region (amino acids 109-120, bold and double underlined) and the end of the C1 region (amino acids 46-52, bold type) of strain PMC21.

The amplification product of this reaction is HOMP5'/SO-G.

The C3 and part of C4 regions will be amplified using the following oligonucleotide primers:

SO-H: 5'-TTCACCTACTCGCTG AAA AAA GAC-3' (SEQ ID NO 49); which encodes amino acids 125-132 at the start of C3 (underlined indicates reverse complement of Primer SO-G)

SO-I: 5'-GCC AGC GTT TAA TAC GTC TTT AAC GCT TGC CGC ACG ATCGGTCAAAGTCGAACCAAT-3' (SEQ ID NO 50); which encodes the reverse complement of amino acids 182-88 at the end of C3 (underlined) and amino acids 211-222 of C4 (bold type)

The amplification product of this reaction is SO-H/SO-I.

The amplification products HOMP5'/SO-G and SO-H/SO-I are purified from agarose gel following separation by electrophoresis, mixed and subjected to further amplification using primers HOMP5' and SO-I to yield a product encoding amino acids 1-52, 103-114, 125-188, and 211-222, i.e. regions C1, C2, C3 and part of C4. The amplification product of this reaction is HOMP5'/SO-I.

The C5 and part of C4 regions are amplified using the following oligonucleotide primers:

SO-J: 5' GTATTAAACGCTGGCTGGAACATTAAAGGCG TTAAA AAC GTT GAT TTC GTC CGC ACT-3' (SEQ ID NO 51); which encodes amino acids 218-229 of C4 (underlined), and amino acids 237-243 of C5 (bold type) of wild-type NhhA of strain PMC21. (Bold underlined type indicates reverse complement of SO-I)

HO3'AN: 5'-TGG AAT CCA TGG AAT CGC CAC CCT TCC CTT C-3' (SEQ ID NO:41).

The amplification product of this reaction is SO-J/HO3'AN.

The amplification products HOMP5'/SO-I and SO-J/HO3'AN will be purified from agarose gel following separation by electrophoresis, and will be mixed, and subjected to further amplification using primers HOMP5' and HO3'AN. The resulting product encodes amino acids 1-52, 103-114, 125-188, 211-229, and 237-591 of wild-type NhhA of strain PMC21. The resulting product will be subjected to restriction digestion with EagI and NcoI, and cloned into pCO14K. This recombinant molecule contains regions C1, C2, C3, C4 and C5, thus deleting regions V1, V2, V3, and V4. The nucleotide sequence of the open reading frame is shown in FIG. 9B and SEQ ID NO:32, and the predicted polypeptide sequence derived from this nucleotide sequence is shown in FIG. 9A and SEQ ID NO: 27. Analysis of the predicted amino acid sequence using the computer program SIGCLEAVE (part of the eGCG suite of programs available from the Australian National Genomic Information Service {ANGIS}) indicates that the first 51 amino acids will be cleaved to produce the mature polypeptide (FIG. 14G; SEQ ID NO:39).

This construct can be transformed into any transformation competent strain of *N. meningitidis.*

EXAMPLE 9

Purification of Over Expressed NhhA Polypeptides

Recombinant NhhA polypeptide as described in the previous Examples may be isolated by the following procedure. Bacteria are grown overnight (12-14 hours) at 37° C. in an atmosphere of 5% $CO_2$. (In this example, media was BHI agar supplemented with Leventhal's base. Other growth media are well known to those skilled in the art). Bacteria from ten 25 mL agar plates were collected and suspended in 25 mL 10 mM Tris adjusted to ph 8.0 with HCl. An equal volume of 10 mM Tris (pH 8.0) containing 2% sarkosyl was added and the mixture mixed gently for 1 hour at 4° C. This was centrifuged at 100,000×g for seventy minutes at 20° C. and the supernatant discarded. The pellet was resuspended in 25 mL 10 mM Tris (pH 8.0) containing 1% sarkosyl by passing through a 25 gauge needle. This was centrifuged at 100,000×g for seventy minutes at 20° C. and the supernatant discarded. The pellet was resuspended in 10 mL 10 mM Tris (pH 8.0) by passing through a 25 gauge needle. This fraction contains the sarkosyl insoluble components of the cell, and is enriched for outer membrane proteins. (An additional step may be incorporated to remove residual sarkosyl detergent, whereby the protein solution is dialysed for four cycles of 4-8 hours against 100-1000 volumes of, for example, 10 mM Tris.Cl pH 8.0 or PBS (phosphate buffered saline) at 4° C.

Having determined the concentration of protein in the suspension by absorbance at wavelength of 280 nm, or by using a BCA kit (Pierce), approximately 1 mL of solution containing 10 mg of protein in a solution containing 1% SDS (sodium lauryl sulphate), 2% β-mercaptoethanol was separated on 1.5 mm thick 6% SDS-PAGE in the BioRad mini-protean II apparatus. The high molecular weight NhhA was eluted from the gel using the BioRad "mini Whole gel Eluter". Approximately 10% of each eluted faction was checked by SDS-PAGE separation followed by Coomassie staining. Fractions containing NhhA essentially free of other proteins were pooled. This procedure was carried out to isolate over expressed mature NhhA as described in Example 2 (SEQ ID NO:1), over expressed BglII deletion mature NhhA as described in Example 4 (SEQ ID NO:23) and over expressed NhhA deletion mutant as described in Example 6 (SEQ ID NO:25). Isolated protein is shown in FIG. 12.

EXAMPLE 10

Immunogenicity of Purified NhhA Deletion Mutant Polypeptides

Mice were inoculated with purified wild-type NhhA polypeptides and deletion mutants as described in the previous Examples. In one group, each Balb/C mouse was inoculated subcutaneously with approximately 130 μg PMC21 NhhA with MPL+TDM™ adjuvant (obtained from Sigma-Aldrich) on day 0, 115 μg on day 14. In a second group, each mouse was inoculated with approximately 120 μg protein with MPL+TDM™ adjuvant (obtained from Sigma-Aldrich) at day 0 and 190 μg at day 14. In a third group, each mouse was inoculated with approximately 260 μg protein with MPL+TDM™ adjuvant (obtained from Sigma-Aldrich) at day 0 and 1240 μg at day 14. Blood samples were taken at day 21 and serum was extracted. These sera were tested for the presence of antibodies recognising full length PMC21 NhhA by Western immunoblot (FIG. 13). OMC preparations (5 mg) of P6 (overexpresses PMC21 NhhA) and Strain 2A (NhhA expression abolished) were separated by 6% SDS-PAGE using the BioRad Mini Protean II electrophoresis apparatus. The proteins were transferred to nitrocellulose electrophoretically, and the filter was cut into 3 mm strips then blocked in 5% skim milk in PBS. Mouse sera was diluted to 1:1000 and 1:10000 in 5% skim milk powder and icnubated with the nitrocellulose strips. Antibody binding was detected using alkaline-phosphatase conjugated anti-mouse IgG (Sigma) before colorimetric detection with NBT/BCIP (Sigma). As can be seen from FIG. 13, it is possible to elicit an immune response against the full length mature PMC21 NhhA polypeptide by inoculation with NhhA deletion mutants or with full length mature NhhA polypeptides.

EXAMPLE 11

Expression of Deletion Mutant Polypeptide in *E. Coli*

In addition to expression of the mutant polypeptides of the invention in *N. meningitidis*, they may also be expressed in *E. coli* bacteria. Any of the recombinant nhhA deletion mutants of Examples 4-8 may be used as template for PCR amplifcation. Oligonucleotide primers used may be as described in International Publication WO99/31132 (such as SEQ ID NO 24 and SEQ ID NO 25 of that document). The amplification product may be restriction digested with BamHI/HindIII enzymes and ligated with BamHI/HindIII restriction digested plasmid pMALC2 (New England BioLabs), and the resultant plasmid transformed into competent *E. coli* strain DH5α. The resulting strain can be induced to express high levels of recombinant protein using conditions recommended by the manufacturer of pMALC2. The resulting recombinant protein is a fusion of maltose binding protein and the deletion mutant NhhA polypeptide of the invention. This may be semi-purified by separation on SDS-PAGE followed by electroelution using the Mini-Gel Electro-eluter (BioRad) according to manufacturers instructions. The semi-purified fusion protein may then be dialysed against PBS, before digestion with the protease enzyme Factor Xa. to cleave the maltose binding protein moiety from the recombinant NhhA protein. The recombinant NhhA protein may be purifed by standard methods as for example described by R. K. Scopes, Protein Purification (Springer-Verlag, New York, N.Y. USA, 1993).

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

|  | C1 | V1 | C2 | V2 | C3 | V3 | C4 | V4 | C5 |
|---|---|---|---|---|---|---|---|---|---|
| Consensus SEQ ID NO: 11 | 1-50 | 51-108 | 109-120 | 121-134 | 135-198 | 199-220 | 221-239 | 240-248 | 249-604 |
| PMC21 SEQ ID NO: 1 | 1-50 | 51-108 | 109-120 | 121-124 | 125-188 | 189-210 | 211-229 | 230-236 | 237-591 |
| H41 SEQ ID NO: 2 | 1-50 | 51-102 | 103-114 | 115-124 | 125-188 | 189-210 | 211-229 | 230-236 | 237-591 |
| P20 SEQ ID NO: 3 | 1-50 | 51-105 | 106-117 | 118-121 | 122-185 | 186-205 | 206-224 | 225-234 | 235-589 |
| EG327 SEQ ID NO: 4 | 1-50 | 51-104 | 105-116 | 117-126 | 127-190 | 191-212 | 213-231 | 232-238 | 239-594 |
| EG329 SEQ ID NO: 5 | 1-50 | 51-108 | 109-120 | 121-124 | 125-188 | 189-210 | 211-229 | 230-236 | 237-591 |
| H38 SEQ ID NO: 6 | 1-50 | 51-105 | 106-117 | 118-131 | 132-195 | 196-217 | 218-236 | 237-243 | 244-599 |
| H15 SEQ ID NO: 7 | 1-50 | 51-104 | 105-116 | 117-130 | 131-194 | 195-216 | 217-235 | 236-242 | 243-598 |
| EZ10 SEQ. ID NO: 8 | 1-50 | 51-104 | 105-116 | 117-130 | 131-194 | 195-216 | 217-235 | 236-242 | 243-598 |
| EZ198 SEQ ID NO: 9 | 1-50 | 51-104 | 105-116 | 117-126 | 127-190 | 191-212 | 213-231 | 232-238 | 239-594 |
| Z2491 SEQ ID NO: 10 | 1-50 | 51-102 | 103-114 | 115-124 | 125-188 | 189-208 | 209-227 | 228-236 | 237-592 |

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |

TABLE 2-continued

| Original Residue | Exemplary Substitutions |
|---|---|
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

We claim:

1. An isolated protein having the amino acid sequence SEQ ID NO:23.

2. A mature, processed form of the isolated protein of claim 1, having the amino acid sequence SEQ ID NO:35.

3. An isolated protein comprising at least one deletion of a non-conserved amino acid in a variable region of SEQ ID NO:23 or SEQ ID NO:35, wherein the isolated protein is immunogenic.

4. An isolated protein variant of SEQ ID NO:23 or SEQ ID NO:35 comprising at least one conservative amino acid substitution in a variable region of SEQ ID NO:23 or SEQ ID NO:35, wherein the isolated protein variant is immunogenic.

5. An isolated protein having at least 90% sequence identity to SEQ ID NO:23 or SEQ ID NO:35, wherein one or more variable regions of a wild-type NhhA polypeptide are absent and wherein the isolated protein is immunogenic.

6. A pharmaceutical composition comprising the isolated protein of claim 1 and a pharmaceutically-acceptable carrier, diluent, or excipient.

7. A pharmaceutical composition comprising the isolated protein of claim 2 and a pharmaceutically-acceptable carrier, diluent, or excipient.

8. The pharmaceutical composition of claim 6 which is immunogenic.

9. The pharmaceutical composition of claim 7 which is immunogenic.

10. A pharmaceutical composition comprising the isolated protein variant of claim 4 and a pharmaceutically-acceptable carrier, diluent, or excipient.

11. The pharmaceutical composition of claim 10 which is immunogenic.

12. A pharmaceutical composition comprising the isolated protein of claim 3 and a pharmaceutically-acceptable carrier, diluent, or excipient.

13. The pharmaceutical composition of claim 12 which is immunogenic.

* * * * *